US010774116B2

(12) United States Patent
Barlow et al.

(10) Patent No.: US 10,774,116 B2
(45) Date of Patent: Sep. 15, 2020

(54) PROTEINS WITH DIAGNOSTIC AND THERAPEUTIC USES

(71) Applicant: THE UNIVERSITY COURT OF THE UNIVERSITY OF EDINBURGH, Edinburgh (GB)

(72) Inventors: Paul Barlow, Edinburgh (GB); Andrew Herbert, Edinburgh (GB); Elisavet Makou, Edinburgh (GB)

(73) Assignee: The University Court of the University of Edinburgh (GB)

( * ) Notice: Subject to any disclaimer, the term of this patent is extended or adjusted under 35 U.S.C. 154(b) by 0 days.

(21) Appl. No.: 16/028,740

(22) Filed: Jul. 6, 2018

(65) Prior Publication Data
US 2019/0100563 A1 Apr. 4, 2019

Related U.S. Application Data

(62) Division of application No. 15/029,399, filed as application No. PCT/GB2014/053072 on Oct. 13, 2014, now Pat. No. 10,035,827.

(30) Foreign Application Priority Data

Oct. 14, 2013 (GB) .................................. 1318170.6

(51) Int. Cl.
| | |
|---|---|
| *A61K 39/00* | (2006.01) |
| *A61K 39/02* | (2006.01) |
| *A61K 49/00* | (2006.01) |
| *C07K 14/315* | (2006.01) |
| *C07K 14/47* | (2006.01) |
| *A61K 9/48* | (2006.01) |
| *A61K 38/16* | (2006.01) |
| *A61L 27/34* | (2006.01) |
| *A61L 27/54* | (2006.01) |
| *A61L 29/08* | (2006.01) |
| *A61L 29/16* | (2006.01) |
| *A61L 31/10* | (2006.01) |
| *A61L 31/16* | (2006.01) |
| *A61K 38/00* | (2006.01) |

(52) U.S. Cl.
CPC ............ *C07K 14/3156* (2013.01); *A61K 9/48* (2013.01); *A61K 38/164* (2013.01); *A61L 27/34* (2013.01); *A61L 27/54* (2013.01); *A61L 29/085* (2013.01); *A61L 29/16* (2013.01); *A61L 31/10* (2013.01); *A61L 31/16* (2013.01); *C07K 14/472* (2013.01); *A61K 38/00* (2013.01); *G01N 2333/3156* (2013.01); *G01N 2333/4716* (2013.01)

(58) Field of Classification Search
CPC ................................ A61K 39/00; A61K 39/02
USPC .......... 424/184.1, 185.1, 234.1, 278.1, 282.1
See application file for complete search history.

(56) References Cited

U.S. PATENT DOCUMENTS

| | | | | |
|---|---|---|---|---|
| 7,049,419 | B2 * | 5/2006 | Briles ................ | C07K 14/3156 424/244.1 |
| 7,479,282 | B2 * | 1/2009 | Tuomanen ......... | C07K 14/3156 424/184.1 |

FOREIGN PATENT DOCUMENTS

| | | |
|---|---|---|
| CA | 2416657 A1 | 1/2002 |
| WO | WO1999053940 | 10/1999 |
| WO | WO2002008426 | 7/2001 |
| WO | 2012087925 A1 | 6/2012 |
| WO | WO2012072769 | 6/2012 |

OTHER PUBLICATIONS

Brooks-Walter, The pspC gene encodes a second pneumococcal surface protein homologous to the gene encoding the protection-eliciting PspA protein of *Streptococcus pneumoniae*, Dec. 22, 2017, p. 35, B-37, vol. 22, Microbial Pathogenesis.
Examination Report No. 2 for Australian Application No. 2014335925, dated Sep. 20, 2018, by IP Australia.
English translations of Exam Report for Japanese Application No. 2016-522745, dated Jul. 31, 2018, by the Japanese Patent Office.

* cited by examiner

*Primary Examiner* — Rodney P Swartz
(74) *Attorney, Agent, or Firm* — Dickinson Wright PLLC

(57) ABSTRACT

The present invention provides a recombinant protein capable of binding to complement factor H (CFH), and thereby inducing increased binding of C3d and C3b by bound CFH compared to unbound CFH.

Methods and medical devices for using utilising the same are also described.

2 Claims, 26 Drawing Sheets
Specification includes a Sequence Listing.

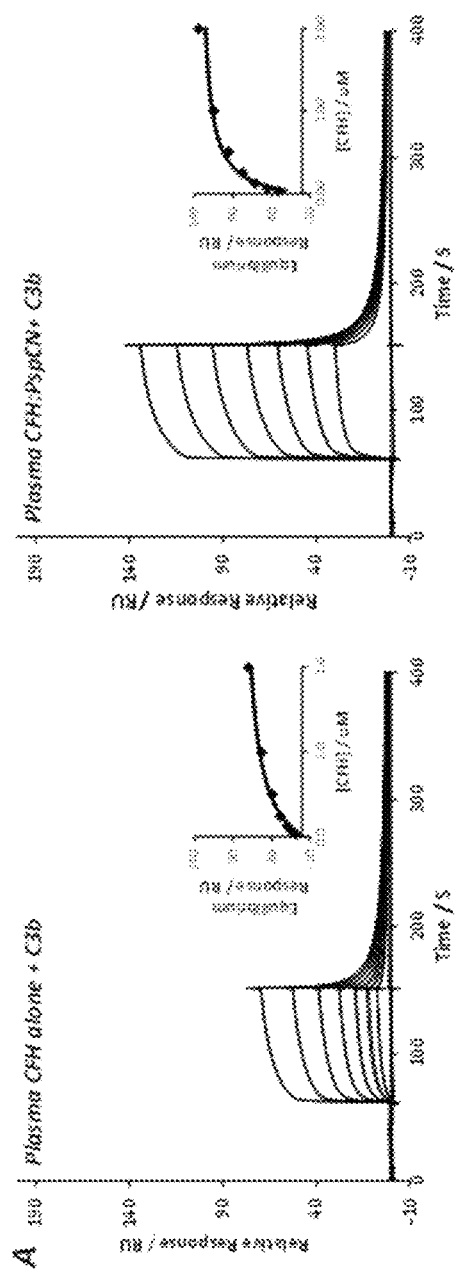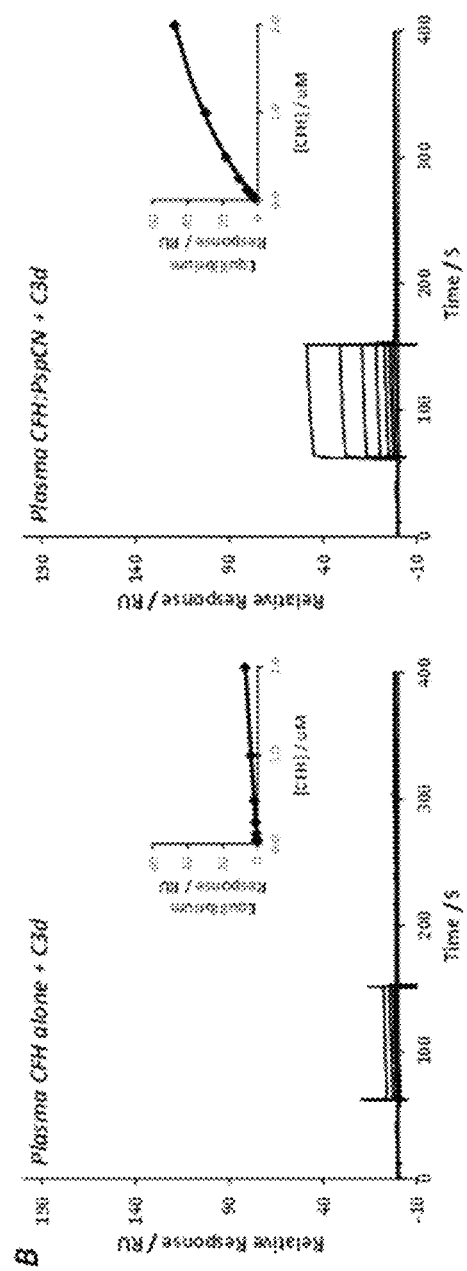
Fig 6A
Fig 6B

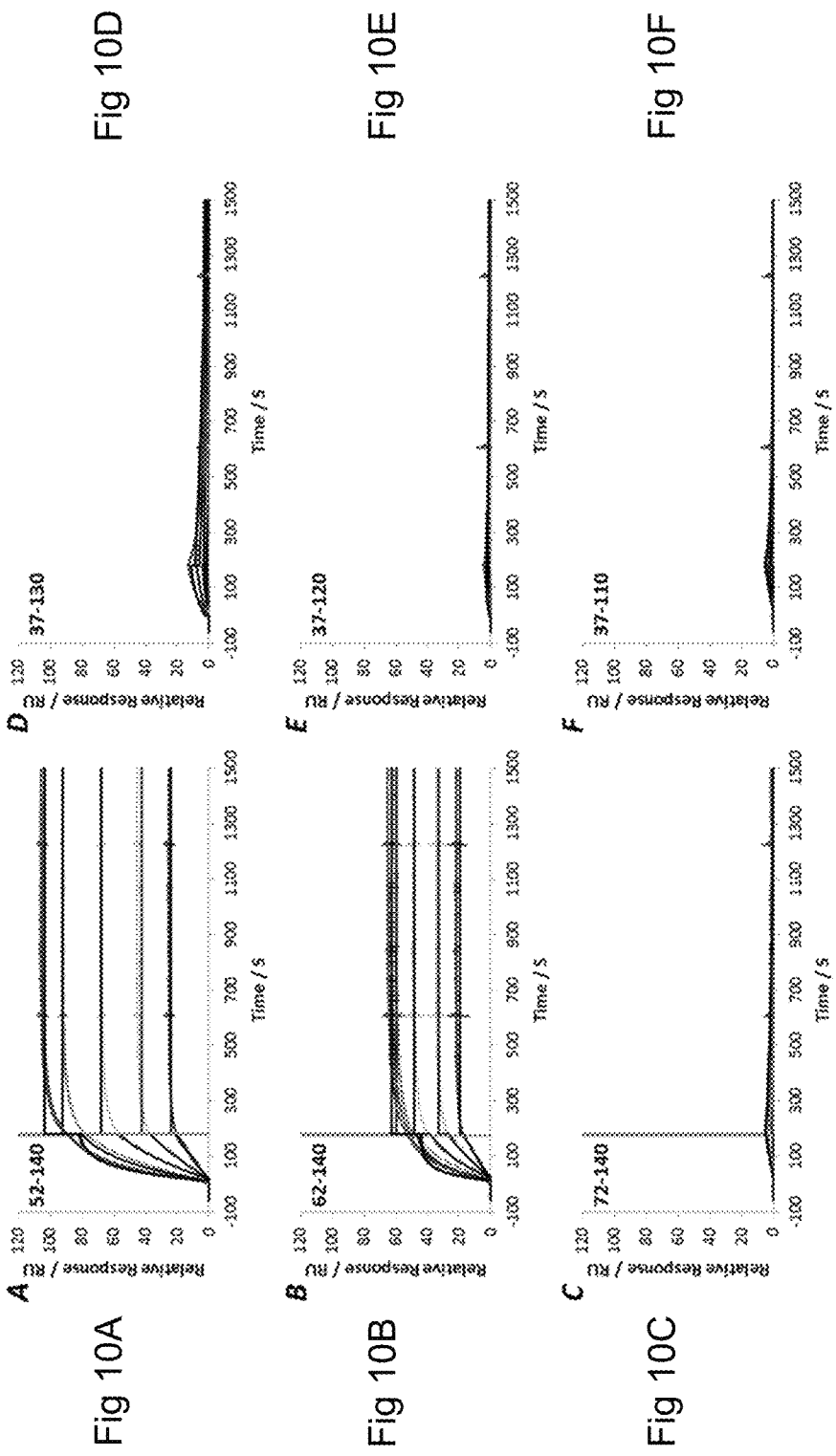

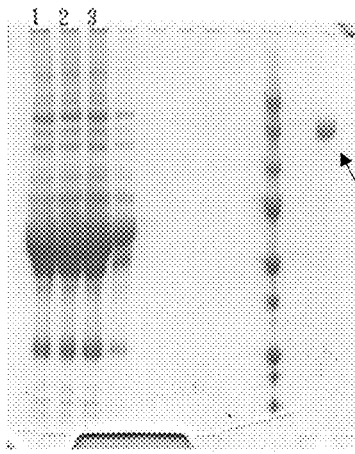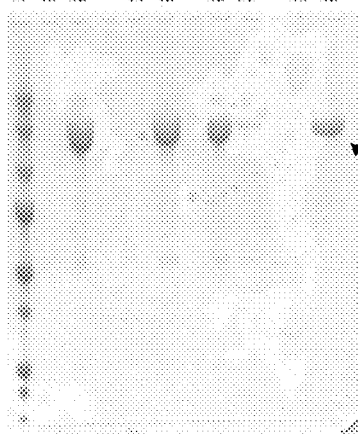
Fig 17

PROTEINS WITH DIAGNOSTIC AND THERAPEUTIC USES

The present application is a divisional of, and claims the benefit of priority from, U.S. patent application Ser. No. 15/029,399, filed 14 Apr. 2016, now U.S. Pat. No. 10,035,827, which is itself the 371 National Stage of International Application PCT/GB2014/053072, filed 14 Oct. 2014, and through which priority is claimed to UK Patent Application 1318170.6, filed 14 Oct. 2013, the disclosures of which applications are incorporated herein by reference in their entireties.

The present invention relates to proteins able to interact with complement factor H and modulate its activity. The invention also relates to methods of using such proteins in therapeutics, diagnostics and other applications.

BACKGROUND OF THE INVENTION

The complement system is a set of 40-50 proteins in the blood that provides a first line of defence against infection. An improperly regulated complement system can damage host or self-cells as well as bacterial ones. It can thus cause or exacerbate the symptoms of many diseases. There is consequently much interest in developing reagents that monitor or modulate the proteins of the complement system.

Human complement factor H (CFH) is a protein that acts selectively on self-surfaces in order to protect them from complement system-mediated damage. Yet many pathogens can exploit host CFH for their own purposes. Studying how CFH (consisting of 20 complement control protein (CCP) modules, also referred to as short consensus repeats (SCRs) or sushi domains) interacts with the relevant microbial proteins has provided clues as to how CFH can be captured and its activity modulated by polypeptides produced in the laboratory.

PspC is one of four designations for a pneumococcal surface protein whose gene is present in approximately 75% of all *Streptococcus pneumoniae* strains. Under the name SpsA, the protein has been shown to bind secretary immunoglobulin A (S. Hammerschmidt, S. R. Talay, P. Brandtzaeg, and G. S. Chhatwal, Mol. Microbiol. 25:1113-1124, 1997). Under the name CbpA, the protein has been shown to interact with human epithelial and endothelial cells (C. Rosenow at al., Mol. Microbiol. 25:819-829, 1997). The gene is paralogous to the PspA gene in *S. pneumoniae* and was thus called PspC (A. Brooks-Walter, R. C. Tart, D. E. Briles, and S. K. Hollingshead, Abstracts of the 97th General Meeting of the American Society for Microbiology 1997). Under the name HIC, the protein has been shown to interact with human factor H (Janulczyk R., Iannelli P., Sjoholm A. G., Pozzi G., Bjorck L. J. Biol. Chem. 275:37257-37263, 2000). A detailed description of PspC is provided in Brooks-Walter et al., "*The pspC Gene of Streptococcus pneumoniae Encodes a Polymorphic Protein, PspC, Which Elicits Cross-Reactive Antibodies to PspA and Provides Immunity to Pneumococcal Bacteremia*" Infect Immun. 1999 December; 67(12): 6533-6542. PMCID: PMC97064. In this paper sequence comparisons of five published and seven new alleles reveal that this gene has a mosaic structure, and modular domains have contributed to gene diversity during evolution. Two major clades exist: clade A alleles are larger and contain an extra module that is shared with many PspA alleles; clade B alleles are smaller and lack this PspA-like domain. All alleles have a proline-rich domain and a choline-binding repeat domain that show 0% divergence from similar domains in the PspA protein.

The present inventors produced a *Streptococcus pneumoniae* PspC truncation (PspCN) that binds CFH irreversibly (on the biological timescale) primarily via interactions with CCPs 8-10. PspCN-captured CFH adopts a conformation in which a chemical cross-linker can conjoin its CCP 5 and CCP 18, as well as its CCP 7 and CCP 20; it is of interest that CCPs 7 and 20 mediate self-surface recognition and are dual binding sites for numerous other CFH-interacting bacteria.

In experiments conducted using surface plasmon resonance, the PspCN:CFH complex was found to bind at least threefold better than CFH to immobilised C3b, the activated version of complement component C3. The PspCN:CFH complex bound many times better than CFH to the proteolytic C3b fragment, C3d. The PspCN:CFH complex dissociated the C3 convertase, C3b.Bb (the enzyme that cleaves C3 to C3a and C3b) up to tenfold more effectively than CFH. These observations were speculatively attributed to exposure upon complex formation of an occluded surface-interacting and C3d/C3b-binding site within CCPs 19-20 of CFH.

In support of this notion, it was found that CFH (D1119G)—which lacks a critical residue within the C3d/C3b:CCP 19 interface and is linked to the kidney disease atypical haemolytic uraemic syndrome—bound to C3b immobilised on a surface plasmon resonance chip, and decayed similarly immobilised C3b.Bb, just as effectively as CFH (wild-type): yet this mutant did not prevent complement-mediated haemolysis of sialic acid-bearing erythrocytes, implying that CCPs 19-20 are utilised for the regulatory action of CFH on self-surfaces even though they do not contribute to binding C3b on a surface plasmon resonance chip.

Importantly, PspCN:CFH (D1119G) bound many fold more weakly than PspCN:CFH (wild-type) to C3d and showed little enhancement, over CFH (D1119G) alone, of C3b.Bb-decay acceleration. Hence, it was hypothesised by the inventors that CFH "hides" regulatory sites to avoid bacterial exploitation but PspC exposes them. Similar FH conformational switches may operate on self-surfaces.

There is an unmet need for methods and compositions for selectively binding complement components, in particular CFH, to solid supports and for modulating complement activity.

The ability to modulate complement activity opens up opportunities, inter alia, for treating diseases associated with aberrant complement activity.

STATEMENTS OF THE INVENTION

According to a first aspect of the present invention there is provided a recombinant protein capable of binding to complement factor H (CFH), and thereby inducing increased binding of C3d and C3b by bound CFH compared to unbound CFH.

The recombinant protein may be capable of binding to CFH, and thereby inducing increased affinity for C3d and C3b by bound CFH compared to unbound CFH.

The proteins of the present invention are thus able to act, through their interaction with CFH, as inhibitors of C3b amplification in the alternative complement pathway.

Preferably said protein is capable of binding to wild type CFH to form a complex with a dissociation constant of $K_D$ of $1\times10^{-10}$ M or lower, more preferably with a $K_D$ of $1\times10^{-11}$ M or lower, yet more preferably with a $K_D$ of $1\times10^{-12}$ M or lower, and most preferably with a $K_D$ of $1\times10^{-13}$ M or lower.

Suitable assays to assess the capability of any protein to achieve this requirement are set out below.

Suitably the protein is derived from a bacterial protein. For example, the protein can be a fragment of a bacterial protein.

Pathogens that have been shown to recruit factor H include: *Aspergillus* spp.; *Borrelia burgdorferi*; *B. duttonii*; *B. recurrentis*; *Candida albicans*; *Francisella tularensis*; *Haemophilus influenzae*; *Neisseria meningitidis*; *Streptococcus pyogenes*; and *Streptococcus pneumoniae*.

Accordingly, proteins from said pathogens can be used to develop proteins according to the present invention.

In preferred embodiments of the invention the protein is derived from a bacterial virulence factor, e.g. it corresponds to a fragment or variant of a virulence factor.

In a preferred embodiment of the invention, proteins of the present invention are derived from a pneumococcal surface protein, especially pneumococcal surface protein C (PspC) from *Streptococcus pneumoniae*.

Various forms of PspC are known, e.g. variants derived from different strains of *S. pneumoniae*. Any of these variants can be used in the present invention. The PspCs derived from strains D39 and TIGR4 are particularly well-studied variants, and were the focus of the specific experimentation described below.

Accordingly, in a preferred embodiment of the present invention, the proteins of the present invention can be derived from PspC of strain D39 (NCTC no 7466) of *S. pneumoniae*. In another preferred embodiment of the present invention, the proteins of the present invention can be derived from CbpA of strain TIGR4 (NCTC no 7465). However, a PspC protein from any other strain could be used, provided it is capable of binding to and enhancing the complement regulatory activity of CFH.

The GenBank/EMBL accession numbers for the nucleotide sequence of PspC from various different strains are as follows: D39, AP068646; EF6796, U72655; DBL6A, AF068645; E134, AF068647; BG8090, AF068648; L81905, AF068649; and BG9163, AF068650.

Suitably the protein of the present invention comprises a fragment of PspC, wherein said fragment comprises a portion of the N-terminal region of PspC.

In one embodiment of the present invention, the protein of the present invention comprises a fragment of PspC comprising a portion of the first 250 amino acids of PspC, numbered from the N terminus, or a functional variant thereof. Preferably the protein of the present invention comprises no additional sequences from PspC. That is to say, the protein comprises a portion of the first 250 amino acids of PspC, and may contain other sequences in addition to this, but these sequences are preferably not PspC-derived sequences.

Suitably the protein comprises a fragment of PspC, or a variant thereof, which is from 70 to 150 amino acid residues in length, suitably from 80 to 130 amino acid residues in length, and typically from 90 to 120 amino acids in length.

Suitably the entire protein according to the present invention is from 70 to 150 amino acid residues in length, suitably from 80 to 130 amino acid residues, and optionally from 90 to 120 amino acid residues, but in many cases, e.g. fusion proteins, it can be larger.

In some embodiments the protein of the present invention is soluble in the physiological environment, e.g. in serum. In other cases, it could be insoluble or bound or adsorbed to a surface.

In a preferred embodiment, the protein of the present invention comprises the sequence:

```
                                          (SEQ ID NO 1)
ATENEGSTQAATSSNMAKTEHRKAAKQVVDEYIEKMLREIQLDRRKHTQN

VALNIKLSAIKTKYLRELNVLEEKSKDELPSEIKAKLDAAFEKFKKDTLK

PGEK,
``` or a functional variant or fragment thereof.

This specific sequence comprises amino acid residues 37-140 of PspC and is henceforth termed PspCN. The amino acid numbering is based upon the full-length sequence of PspC as set out in Genbank accession no AF068646.

PspCN represents a fragment of PspC, derived from the N-terminal region, which has the ability to bind extremely strongly to, and activate, CFH. In fact, it binds to CFH so strongly that it appears to be irreversible, to all intents and purposes.

In another preferred embodiment, the protein of the present invention comprises the sequence:

```
                                          (SEQ ID NO 2)
KQVVDEYIEKMLREIQLDRRKHTQNVALNIKLSAIKTKYLRELNVLEEK

SKDELPSEIKAKLDAAFEKFKKDTLKPGEK
``` or a functional variant or fragment thereof.

This specific sequence represents a further truncated form of PspC, compared to PspCN, which comprises amino acids 62-140 of PspC, and will be termed PspCN (62-140). It appears that PspCN (62-140) represents the minimum, or near minimum, fragment of PspC which is able to bind to CFH with high affinity.

In another preferred embodiment, the protein according to the present invention comprises the sequence:

```
                                          (SEQ ID NO 9)
ATENEGATQVPTSSNRANESQAEQGEQPKKLDSERDKARKEVEEYVKKIV

GESYAKSTKKRHTITVALVNELNNIKNEYLNKIVESTSESQLQILMMESR

SKVDEAVSKFEKDSSSSSSSDSSTKPEASDTAKPNKPTEPGEK
``` or a functional variant or fragment thereof.

It is possible that slightly smaller fragments of PspC may also be able to bind CFH with high affinity, but shortening of the N- or C-terminus of PspCN (62-14G) by 10 amino acids has been shown to be severely detrimental to CFH binding affinity.

Thus, in preferred embodiments of the present invention the protein comprises at least amino acid residues 68-136, and more preferably 65-138, yet more preferably 62-140 of PspC, of a functional variant thereof.

It is of course, possible that portions within PspCN (62-140) can be removed or replaced without adversely affecting functionality of the protein, and determining which regions could be removed or replaced is within the routine skills of the person skilled in the art. Proteins in which portions within amino acids 82-140 have been removed or replaced, but which remain functional, are within the scope of the present invention, as is discussed in more detail below.

A particularly interesting property of the proteins of the present invention is that they appear to be highly selective for CFH. For example, it appears that proteins according to the present invention are able to selectively bind CFH in preference to the related protein CFH-like protein 1 or other CFH-related proteins. This has implications in terms of therapeutic, diagnostic and other uses of the proteins.

The proteins of the present invention preferably bind to CFH primarily at a location within CCPs between 8 and 15, and preferably at a location within CCPs 8-10 of CFH.

Furthermore, the fragments described above can be part of a larger protein and retain its binding properties (e.g. as part of a fusion protein or a larger fragment of PspC).

It will thus be apparent to the skilled person that the invention is not restricted to the precise sequence of SEQ ID NO 1 or 2, and that variants or fragments thereof that retain the biological activities of PspCN, i.e. remain functional with respect to CFH binding and activation, also fall within the scope of the present invention.

In particular, variants or fragments that have a $K_D$ when completed with wild type CFH of 10 nM or lower, more preferably 1 nM or lower, more preferably 100 pM or lower, more preferably 10 pM or lower and most preferably 1 pM or lower are preferred embodiments of the present invention. Surprisingly, proteins such as PspCN and PspCN (62-140) have been measured to have a $K_D$ of as low as $5 \times 10^{-14}$ M and, thus, especially preferred proteins of the present invention have an affinity represented by a $K_D$ of $1 \times 10^{-13}$ M or lower. It needs hardly be said that a higher affinity corresponds to a lower $K_D$.

As used herein, the term "protein" can be used interchangeably with "peptide" or "polypeptide", and means at least two covalently attached alpha amino acid residues linked by a peptidyl bond. The term protein encompasses purified natural products, or chemical products, which may be produced partially or wholly using recombinant or synthetic techniques. The term protein may refer to a complex of more than one polypeptide, such as a dimer or other multimer, a fusion protein, a protein variant, or derivative thereof. The term also includes modified proteins, for example, a protein modified by glycosylate, acetylation, phosphorylation, pegylation, ubiquitination, and so forth. A protein may comprise amino acids not encoded by a nucleic acid codon.

It will be obvious that proteins having minor modifications in the sequence are equally useful, provided they are functional, and the invention thus also provides a protein comprising an amino acid sequence showing at least 50% similarity with the amino acid sequence as depicted in SEQ ID NO 1 or a functional fragment thereof. The invention preferably provides a protein comprising a polypeptide sequence which has at least 60%, or preferably at least 70%, more preferably 80%, more preferably, 90%, more preferably at least 99%, most preferably 100% similarity to the sequence in SEQ ID NO 1, or a functional fragment thereof.

The term "similarity" refers to a degree of similarity between proteins in view of differences in amino acids, but which different amino acids are functionally similar in view of almost equal size, lipophilicity, acidify, etc. is taken into account. A percentage similarity can be calculated by optimal alignment of the sequences using a similarity-scoring matrix such as the Blosum 62 matrix described in Henikoff S. and Henikoff J. G., P.N.A.S. USA 1992, 89: 10915-10919. Calculation of the percentage similarity and optimal alignment of two sequences using the Blosum 62 similarity matrix and the algorithm of Needleman and Wunsch (J. Mol. Biol. 1970, 48: 443-453) can be performed using the GAP program of the Genetics Computer Group (GCG, Madison, Wis., USA) using the default parameters of the program.

Exemplary parameters for amino acid comparisons in the present invention use the Blosum 62 matrix (Henikoff and Henikoff, supra) in association with the following settings for the GAP program:

Gap penalty: 8
Gap length penalty: 2
No penalty for end gaps.

Polymorphic forms of PspC are included in the present invention. Variants of the proteins that also form part of the present invention are natural or synthetic variants that may contain variations in the amino acid residue sequence due to deletions, substitutions, insertions, inversions or additions of one or more amino acid residues in said sequence or due to an alteration to a moiety chemically linked to a protein. For example, a protein variant may be an altered carbohydrate or PEG structure attached to a protein. The proteins of the invention may include at least one such protein modification.

Substitutional variants of proteins are those in which at least one amino acid residue in the amino acid sequence has been removed and a different amino acid residue inserted in its place. The proteins of the present invention can contain conservative or non-conservative substitutions.

The term "conservative substitution", relates to the substitution of one or more amino acid residues for amino acid residues having similar biochemical properties. Typically, conservative substitutions have little or no impact on the activity of a resulting protein. For example, a conservative substitution in a protein of the present invention may be an amino acid residue substitution that does not substantially affect the ability of the protein to bind to, and activate, CFH. Screening of variants of the proteins of the present invention can be used to identify which amino acid residues can tolerate an amino acid residue substitution. In one example, the relevant biological activity of a modified protein is not decreased by more than 25%, preferably not more than 20%, especially not more than 10%, compared with PspCN when one or more conservative amino acid residue substitutions are effected.

One or more conservative substitutions can be included in a protein of the present invention, in one example, 10 or fewer conservative substitutions are included in the protein. A protein of the invention may therefore include 1, 2, 3, 4, 5, 6, 7, 8, 9, 10 or more conservative substitutions. A polypeptide can be produced to contain one or more conservative substitutions by manipulating the nucleotide sequence that encodes that polypeptide using, for example, standard procedures such as site-directed mutagenesis, gene synthesis, or PGR. Alternatively, a polypeptide can be produced to contain one or more conservative substitutions by using peptide synthesis methods, for example as known in the art.

Examples of amino acid residues which may be substituted for an original amino acid residue in a protein and which are regarded as conservative substitutions include: Ser for Ala; Lys for Arg; Gln or His for Asn; Gln for Asp; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val. In one embodiment, the substitutions are among Ala, Val Leu and Ile; among Ser and Thr; among Asp and Glu; among Asn and Gln; among Lys and Arg; and/or among Phe and Tyr. Further information about conservative substitutions can be found in, among other locations, Ben-Basset et al., (J. Bacterial. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988), WO 00/67798 (Curd et al.) and in standard textbooks of genetics and molecular biology.

Other variants can be, for example, functional variants such salts, amides, esters, and specifically C-terminal esters, and N-acyl derivatives. Also included are peptides which are modified in vivo or in vitro, for example by glycosylation, amidation, carboxylation or phosphorylation.

Proteins according to the present invention can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified, for example to form a C1-C6 alkyl ester, or converted to an amide, for example of formula CONR1R2 wherein R1 and R2 are each independently H or C1-C6 alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to C1-C6 alkyl or dialkyl amino or further converted to an amide. Hydroxyl groups of the peptide side chains may be converted to alkoxy or ester groups, for example C1-C6 alkoxy or C1-C6 alkyl ester, using well-recognized techniques. Phenyl and phenolic rings of the peptide side chains may be substituted with one or more halogen atoms, such as F, Cl, Br or I, or with C1-C6 alkyl, C1-C6 alkoxy, carboxylic acids and esters thereof, or amides of such carboxylic acids. Methylene groups of the peptide side chains can be extended to homologous C2-C4 alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability.

Proteins comprising only a functional fragment of PspCN or a variant thereof also form part of the present invention. A functional fragment is a fragment that at least represents the part or parts of the protein, which are essential for the protein to be able to serve to bind and activate CFH, and can fulfil this function, for example, when used alone or in a multi-subunit form. Thus, such functional fragments may be polypeptides that are functional per se, or the fragments may be functional when linked to other polypeptides, e.g. to obtain chimeric proteins. Such functional fragments are understood to fall within the scope of the present invention. Whether a fragment is functional can be determined using the various bioassays herein described.

Fragments can be produced, inter alia, by enzymatic cleavage of precursor molecules, using restriction endonucleases for the DMA and proteases for the polypeptides. Other methods include chemical synthesis of the fragments or the production of peptide fragments encoded by DNA.

The protein of the present invention can be a fusion protein. Numerous means of linking two or more subunits together to form a fusion protein are well known to the skilled person. Such fusion proteins can comprise a linker or have no linker. Suitable linkers are well known in the art, and relevant information can be found, inter alia, in George R A and Heringa J. 'An analysis of protein domain linkers: their classification and role in protein folding'. Protein Eng, 2002 November; 15(11) 871-9.

The bioactivity of proteins according to the invention can be measured in vitro using a suitable bioassay. Suitable bioassays are described below in detail, and include using surface plasmon resonance (SPR) to measure binding of the protein to CFH and measuring the ability of protein-bound CFH to interact with other relevant complement components (e.g. binding to C3b or C3d, or inducing decay of C3b.Bb).

Typically the protein of the present invention is a recombinant protein. For example, the protein can be manufactured through expression in an appropriate cell line such as yeast or *E.coli*.

In a further aspect the present invention provides a composite comprising the protein of the present invention bound to CFH, wherein CFH is held in a conformation, or conformations, that is/are more active than the conformation or conformations adopted by CFH alone. Such a composite can be useful as a therapeutic to increase levels of CFH activity in a subject.

In a further aspect of the present invention, there is provided a nucleic acid encoding the protein of the present invention.

In another aspect, the present invention therefore provides a recombinant vector comprising a polynucleotide according to the invention. Suitable vectors include bacterial or yeast plasmids, cosmids, phagemids, fosmids, wide host-range plasmids and vectors derived from combinations of plasmid and phage or virus DNA. An origin of replication and/or a dominant selection marker can suitably be present in the vector.

The vectors according to the invention are suitable for transforming a host cell. Examples of suitable cloning vectors are plasmid vectors such as pBR322, the various pUC, pEMBL and Bluescript plasmids, or viral vectors.

When used for the expression of a gene encoding the proteins of the present invention, a vector according to the present invention typically comprises an expression control sequence operably linked to the nucleic acid sequence coding for the protein to control expression of the relevant polynucleotide. Such expression control sequences generally comprise a promoter sequence and additional sequences which regulate transcription and translation and/or enhance expression levels. Suitable expression control sequences are well known in the art and include eukaryotic, prokaryotic, or viral promoter or poly-A signal. Expression control and other sequences will, of course, vary depending on the host cell selected and can be constitutive or can be made inducible. Examples of useful promoters are the SV-40 promoter (Science 1983, 222: 524-527), the metallothionein promoter (Nature 1982, 296: 39-42), the heat shock promoter (Voellmy et al., P.N.A.S. USA 1985, 82: 4949-4953), the PRV gX promoter (Mettenleiter and Rauh, J. Virol. Methods 1990, 30: 55-66), the human CMV IE promoter (U.S. Pat. No. 5,168,062), the Rous Sarcoma virus LTR promoter (Gorman et al., P.N.A.S. USA 1982, 79: 6777-6781), or human elongation factor 1 alpha or ubiquitin promoter. Many other suitable control sequences are known in the art, and it would be routine for the skilled person to select suitable sequences for the expression system being used.

After the polynucleotide has been cloned into an appropriate vector, the construct may be transferred into a cell (e.g. animal cell, bacteria, or yeast) by means of an appropriate method, such as electroporation, $CaCl_2$ transfection or lipofectins. When a baculovirus expression system is used, the transfer vector containing the polynucleotide may be transfected together with a complete baculo genome.

These techniques are well known in the art and the manufacturers of molecular biological materials (such as Clontech, Stratagene, Promega, and/or Invitrogen) provide suitable reagents and instructions on how to use them. Furthermore, there are a number of standard reference text books providing further information on this, e.g. Rodriguez, R. L. and D. T. Denhardt, ed., "Vectors: A survey of molecular cloning vectors and their uses", Butterworths, 1988; Current protocols in Molecular Biology, eds.: F. M. Ausubel et al., Wiley N.Y., 1995; Molecular Cloning: a Laboratory Manual, supra; and DNA Cloning, Vol. 1-4, 2nd edition 1995, eds.: Glover and Hames, Oxford University Press).

In a further aspect the present invention also provides a cell capable of expressing a recombinant protein, characterised in that the cell comprises a polynucleotide according to the invention encoding the recombinant protein to be expressed. Suitably the cell is a host cell transformed with a polynucleotide or vector as described above. The polynucleotide or vector according to the invention can be stably integrated into the genomic material of the cell or can be part of an autonomously replicating vector. "Recombinant" in this context refers to a protein that is not expressed in the cell in nature.

Accordingly, the cell may be capable of producing a recombinant protein.

Host cells can be cultured in conventional nutrient media which can be modified, e.g. for appropriate selection, amplification or induction of transcription and thus expression of the recombinant protein.

The host cells can be prokaryotic or eukaryotic. Suitable prokaryotic cells include, for example, *E. coli*, *Corynebacterium* or *Pseudomonas fluorescens*. Suitable eukaryotic cells include, for example, *Pichia pastoris*, insect cells, HeLa, BHK, HEK-293T, CHO, or COS-7 cells.

Suitable culture conditions for various suitable cell types are well-known to the person skilled in the art.

In a further aspect the present invention provides a cell culture comprising cells according to the invention.

In a further aspect of the present invention there is provided a protein according to the present invention for use in the treatment or prevention of disease.

In a further aspect of the present invention there is provided a protein according to the present invention for use in the treatment or prevention of a disease (condition) or other medical complication associated with aberrant complement regulatory activity in a subject or where reducing complement activity is beneficial.

Proteins of the present invention are particularly useful in treating diseases in which complement is inappropriately active, e.g. is overactive.

Proteins of the present invention are particularly useful in treating disease in which the alternative complement pathway is inappropriately active.

Proteins of the present invention are particularly useful in treating disease in which CFH is unable to adequately modulate complement activation, e.g. because of lowered levels of CFH in plasma or mutation or a SNP within the gene (or its regulatory regions) that encodes CFH which reduces CFH production or regulatory activity, or because of changes in self surface markers as may occur e.g. with age or pathology, or because of competition with surface-binding by CFH from CFH-related proteins. Additionally, proteins of the present invention can be useful where the regulatory mechanisms of complement have been overrun for some other reason, e.g. where other complement regulators are deficient in some respect or when triggers of complement activation—that include both foreign matter and the products of host cell damage or death—are abundant. Such diseases are well known to those familiar with the field. As is known in the art, CFH regulates complement activation in fluid phase, and on self-cells and surfaces, by possessing both cofactor activity for the factor I-mediated C3b cleavage, and decay-accelerating activity against the alternative pathway C3-convertase, C3b.Bb.

Suitably the disease is one or more of:
Paroxysmal Nocturnal Hemoglobinuria (PNH),
Atypical Haemolytic Uremic Syndrome (aHUS),
Dense Deposit Disease (DDD);
Age-related Macular Degeneration (AMD);
Systemic Lupus Erythematosus (SLE);
Sepsis; and
Alzheimer's Disease.

Of particular interest from this group of diseases are PNH, aHUS, DDD and AMD, in which the proteins of the present invention are envisaged to be particularly useful.

Suitably the disease mentioned above is associated with a mutation in or affecting CFH. However, some of the diseases mentioned above (e.g. PNH) do not involve mutations or SNPs in CFH, and, for those disease that do involve mutations or SNPs in CFH, not all occurrences of the diseases mentioned above are caused (entirely or in part) by such mutations or SNPs in CFH. The proteins of the present invention are clearly well adapted for cases where CFH is directly involved. However, even in cases where a mutation or SNP in CFH is not present, the proteins of the present invention can still be useful in treating the condition.

The proteins of the present invention enhance the activity of CFH and, as such, can be used to augment the activity of CFH in conditions where inadequate activity of CFH contributes to the pathology of the condition.

In view of the advent of stratified/personalised medicine, in which diseases are profiled and appropriate therapies selected based upon the profile, the proteins of the present invention can be administered where a disease, for example one of the diseases mentioned above, involves aberrant CFH levels or activity or in which the alternative complement pathway is overactive. This allows treatment with the proteins of the present invention to be focussed on conditions where a positive effect is likely to occur.

According to a further aspect of the present invention there is provided a pharmaceutical preparation comprising the protein of the present invention or a nucleic acid encoding a protein of the present invention.

The pharmaceutical composition can suitably comprise a pharmaceutically acceptable carrier.

As used herein "pharmaceutically-acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. The carrier can be suitable for intravenous, subcutaneous, intraperitoneal or intramuscular administration. In another embodiment, the carrier is suitable for oral administration. Pharmaceutically-acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the fusion proteins of the invention, use thereof in the pharmaceutical compositions of the invention is contemplated. The composition, if desired, can also contain minor amounts of wetting or emulsifying agents, or pH buffering agents. Supplementary active compounds can also be incorporated into the compositions.

Ordinarily, the preparation of such pharmaceutical compositions entails combining the active agent with buffers, antioxidants such as ascorbic acid, low-molecular weight (less than about 10 residues) polypeptides, proteins, amino acids, carbohydrates including glucose, sucrose or dextrins, chelating agents such as EDTA, glutathione and other stabilizers and/or excipients. Neutral buffered saline or saline mixed with conspecific serum albumin are exemplary appropriate diluents for protein therapeutics.

In one preferred embodiment, the composition is formulated as a lyophilisate using appropriate excipient solutions (e.g., sucrose) as diluents.

The compositions can take the form of solutions, suspensions, emulsions, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc.

Various literature references are available to facilitate the selection of pharmaceutically acceptable carriers or excipients. See, e.g., Remington's Pharmaceutical Sciences and US Pharmacopeia: National Formulary, Mack Publishing Company, Easton, Pa. (1984); Hardman et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis et al. (Eds.) (1993) Pharmaceutical Dosage Forms: Parenteral Medications, Marcel Dekker, NY; Lieberman, et al. (Eds.) (1990) Pharmaceutical Dosage Forms: Tablets, Marcel Dekker, New York, N.Y.; Lieberman, et al. (Eds.) (1990) Pharmaceutical Dosage Forms: Disperse Systems, Marcel Dekker, NY; Weiner, Wang, E., Int. J. Pharm. 185:128-188 (1999) and Wang W. Int. J. Pharm. 203:1-60 (2000), and Kotkoskie (2000) Excipient Toxicity and Safety, Marcel Dekker, New York, N.Y.

Such compositions will contain a therapeutically effective amount of the protein of the present invention, preferably in purified form, together with a suitable amount of carrier so as to provide the form for proper administration to the patient. The formulation should suit the mode of administration.

In some embodiments the protein of the present invention is provided as a complex with CFH. Such a complex is particularly valuable where a subject to be treated has reduced ability to produce functioning CFH, and thus there may be inadequate CFH present in the subject for the protein to bind to and activate.

In a preferred embodiment, the composition is formulated, in accordance with routine procedures, as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade wafer or saline. Where the composition is administered by injection, an ampoule of stable water or saline for injection can be provided so that the ingredients may be mixed prior to administration.

The compositions of the invention can be formulated as neutral or salt forms. Pharmaceutically acceptable salts include those formed with free carboxyl groups such as those derived from hydrochloric, phosphoric, acetic, oxalic, tartaric acids, etc., those formed with free amine groups such as those derived from isopropylamine, triethylamine, 2-ethylamino ethanol, histidine, procaine, etc., and those derived from sodium, potassium, ammonium, calcium, and feme hydroxides, etc.

Various delivery systems are known and can be used to administer a protein of the invention, e.g., encapsulation in liposomes, micro-particles, and microcapsules: use of recombinant cells capable of expressing the protein of the present invention, use of receptor-mediated endocytosis (e.g., Wu and Wu, 1987, J. Biol. Chem. 262:4429-4432); construction of a therapeutic nucleic acid as part of a retroviral or other vector, etc.

In another embodiment, the pharmaceutical compositions of the invention can be delivered in a vesicle, in particular a liposome (Langer, 1990, Science 249:1527-1533; Treat et al., 1989, In: Liposomes in the Therapy of Infectious Disease and Cancer, Lopez-Berestein and Fidler, eds., Liss, New York, pp. 353-365; Lopez-Bernstein, ibid., pp. 317-327; see generally ibid.)

In yet another embodiment, the pharmaceutical compositions of the invention can be delivered via a controlled release system.

In a specific embodiment where the pharmaceutical compositions of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (U.S. Pat. No. 4,980,286), or by direct injection, or by use of micro-particle bombardment (e.g., a gene gun; Biolistic, Dupont), or by coating it with lipids, cell-surface receptors or transfecting agents, or by administering it in linkage to a homeobox-like peptide which is known to enter the nucleus (e.g., Joliot et al., 1991, Proc. Natl. Acad. Sci. USA 88:1864-868), etc. Alternatively, a nucleic acid can be introduced intracellularly and incorporated by homologous recombination within host cell DMA for expression.

The amount of the pharmaceutical compositions of the invention which will be effective in the treatment of a particular disorder or condition will depend on the nature of the disorder or condition, and can be determined by standard clinical techniques. Appropriate dosages can be determined in trials. In accordance with appropriate industry standards, preservatives may also be added, such as benzyl alcohol. The amount and frequency of administration will depend, of course, on such factors as the nature and severity of the indication being treated, the desired response, the condition of the patient, and so forth. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 1-500 micrograms of active compound per kilogram body weight. Effective doses may be extrapolated from dose-response curves derived from in vitro or animal model test systems.

The invention also provides a pharmaceutical pack or kit comprising one or more containers filled with one or more of the ingredients of the pharmaceutical compositions of the invention.

Optionally associated with such container(s) can be a notice in the form prescribed by a governmental agency regulating the manufacture, use or sale of pharmaceuticals or biological products, which notice reflects approval by the agency of manufacture, use or sale for human administration.

The invention provides methods of treatment or prevention of a disease in a subject by administration to a subject of an effective amount of a pharmaceutical composition of the present invention. In particular, the present invention provides the treatment or prevention of a disease associated with aberrant complement activity in a subject.

The subject is preferably an animal, preferably a mammal, and most preferably a human.

Suitably the disease is one or more of:
Paroxysmal Nocturnal Hemoglobinuria (PNH),
Atypical Haemolytic Uremic Syndrome (aHUS),
Dense Deposit Disease (DDD);
Age-related Macular Degeneration (AMD);
Systemic lupus Erythematosus (SLE);
Sepsis; and
Alzheimer's Disease.

Of particular interest from this group of diseases are PNH, aHUS, DDD and AMD, in which the proteins of the present invention are envisaged to be particularly useful.

The present invention contemplates the administration of the proteins of the invention in the form of a pharmaceutical composition comprising the protein of the invention and a pharmaceutically acceptable diluent or carrier to a subject (e.g., a mammal particularly a human) in need thereof. The present invention also provides a method for treating human disease with such compositions.

Methods of introduction include, but are not limited to intradermal, intramuscular, intraperitoneal, intravenous, subcutaneous, intranasal, epidural, and oral routes. The compounds may be administered by any convenient route, for example by infusion, by bolus injection, by absorption through epithelial or mucocutaneous linings (e.g., oral, rectal and intestinal mucosa, etc.), and may be administered together with other biologically active agents.

Administration can be systemic or local Pulmonary administration can be employed, e.g., by use of an inhaler or nebulizer, and formulation with an aerosolizing agent.

Typically, methods of the invention will comprise administering a pharmaceutical composition comprising a pharmaceutically effective amount of a protein of the invention or a composition comprising a nucleic acid capable of expressing a pharmaceutically effective amount of a protein of the present invention in vivo. The pharmaceutically effective amount employed may vary according to factors such as the disease state, age, sex, and weight of the individual.

A pharmaceutically effective amount of a protein of the invention may be from about 1 µg protein/1 kg body weight of subject to about 500 mg protein/1 kg body weight of subject, or from about 10 µg protein/1 kg body weight of subject to about 500 mg protein/1 kg body weight of subject, or from about 10 mg protein/1 kg body weight of subject to about 500 mg protein/1 kg body weight of subject, or from about 100 mg protein/1 kg body weight of subject to about 500 mg protein/1 kg body weight of subject, or from about 10 mg protein/1 kg body weight of subject to about 500 mg protein/1 kg body weight of subject, or from about 100 mg protein/1 kg body weight of subject to about 500 mg protein/1 kg body weight of subject, or from about 100 µg protein/1 kg body weight of subject to about 25 mg protein/1 kg body weight of subject, or from about 1 mg protein/1 kg body weight of subject to about 25 mg protein/1 kg body weight of subject, or from about 5 mg protein/1 kg body weight of subject to about 25 mg protein/1 kg body weight of subject, or from about 10 mg protein/1 kg body weight of subject to about 25 mg protein/1 kg body weight of subject, or from about 15 mg protein/1 kg body weight of subject to about 25 mg protein/1 kg body weight of subject, or from about 100 µg protein/1 kg body weight of subject to about 10 mg protein/1 kg body weight of subject, or from about 1 mg protein/1 kg body weight of subject to about 10 mg protein/1 kg body weight of subject, or from about 2.5 mg protein/1 kg body weight of subject to about 10 mg protein/1 kg body weight of subject, or from about 5 mg protein/1 kg body weight of subject to about 10 mg protein/1 kg body weight of subject, or from about 7.5 mg protein/1 kg body weight of subject to about 10 mg protein/1 kg body weight of subject.

In some embodiments, a pharmaceutically effective amount of a protein of the invention may be 0.5 mg protein/1 kg body weight or subject, 1 mg protein/1 kg body weight of subject, 2 mg protein/1 kg body weight of subject, 3 mg protein/1 kg body weight of subject, 4 mg protein/1 kg body weight of subject, 5 mg protein/1 kg body weight of subject, 8 mg protein/1 kg body weight of subject, 7 mg protein/1 kg body weight of subject, 8 mg protein/1 kg body weight of subject, 9 mg protein/1 kg body weight of subject, or 10 mg protein/1 kg body weight of subject.

A unit dosage form refers to physically discrete units suited as unitary dosages for the mammalian subjects to be treated; each unit containing a predetermined quantity of the protein of the invention calculated to produce the desired therapeutic effect in association with the required pharmaceutical carrier. A unit dosage form of a protein of the invention may be from about 1 mg to about 1000 mg, from about 25 mg to about 1000 mg, from about 50 mg to about 1000 mg, from about 100 mg to about 1000 mg, from about 250 mg to about 1000 mg, from about 500 mg to about 1000 mg, from about 100 mg to about 500 mg, from about 200 mg to about 500 mg, from about 300 to about 500 mg, or from about 400 mg to about 500 mg. A unit dose of a protein of the invention may be about 100 mg, 200 mg, 300 mg, 400 mg, 500 mg, 800 mg, or 700 mg.

Compositions of the invention may comprise proteins of the invention at a level of from about 0.1 wt % to about 20 wt %, from about 0.1 wt % to about 18 wt %, from about 0.1 wt % to about 16 wt %, from about 0.1 wt % to about 14 wt %, from about 0.1 wt % to about 12 wt %, from about 0.1 wt % to about 10 wt %, from about 0.1 wt % to about 8 wt %, from about 0.1 wt % to about 8 wt % from about 0.1 wt % to about 4 wt %, from about 0.1 wt % to about 2 wt %, from about 0.1 wt % to about 1 wt %, from about 0.1 wt % to about 0.9 wt %, from about 0.1 wt % to about 0.8 wt %, from about 0.1 wt % to about 0.7 wt %, from about 0.1 wt % to about 0.6 wt %, from about 0.1 wt % to about 0.5 wt %, from about 0.1 wt % to about 0.4 wt %, from about 0.1 wt % to about 0.3 wt %, or from about 0.1 wt % to about 0.2 wt % of the total weight of the composition.

Pharmaceutical compositions of the invention may comprise one or more proteins of the invention at a level of from about 1 wt % to about 20 wt %, from about 1 wt % to about 18 wt %, from about 1 wt % to about 16 wt %, from about 1 wt % to about 14 wt %, from about 1 wt % to about 12 wt %, from about 1 wt % to about 10 wt %, from about 1 wt % to about 9 wt %, from about 1 wt % to about 8 wt %, from about 1 wt % to about 7 wt %, from about 1 wt % to about 8 wt %, from about 1 wt % to about 5 wt %, from about 1 wt % to about 4 wt %, from about 1 wt % to about 3 wt %, or from about 1 wt % to about 2 wt % of the total weight of the composition. Pharmaceutical compositions of the invention may comprise one or more proteins of the invention at a level of about 0.1 wt %, about 0.2 wt %, about 0.3 wt %, about 0.4 wt %, about 0.5 wt %, about 0.6 wt %, about 0.7 wt %, about 0.8 wt %. about 0.9 wt %, about 1 wt %, about 2 wt %, about 3 wt %, about 4 about 5 wt %, about 6 wt %, about 7 wt %, about 8 wt %, or about 9 wt % based on the total weight of the composition.

Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Compositions of the invention may be formulated and administered by intravenous, intramuscular, or subcutaneous injection. In some embodiments, compositions of the invention may be administered subcutaneously or intramuscularly.

In some embodiments a dosage regimen may entail administering repeat doses, for example, administering a weekly dose. Treatment regimens may entail a weekly dose for one period of time (for example, for four weeks) followed by a less frequent "maintenance" dosage regimen (for example, one monthly or once bimonthly). Dosage regimens may be adjusted to achieve the desired therapeutic outcomes.

Suitably the method involves targeting the protein of the present invention to a specific site or tissue in the subject. Methods of targeting are well-known in the art, and often include providing a fusion protein which includes a targeting moiety or an otherwise linked targeting moiety. Typical targeting moieties are antibodies or ligands for receptors. For example, a fusion of PspCN with an antibody fragment to collagen IV would target PspCN to the glomerulus, which would be useful for treating aHUS.

In another aspect of the present invention there is provided a protein according to the present invention immobilised on a surface. The surface can be any suitable surface, and includes, for example, the surface of a bead, container, medical device, microcapsule, or a biological tissue.

By attaching the protein of the present invention to a surface, if permits the surface to bind to CFH. This can be useful in many different applications. For example, the bound CFH can be used to protect the surface the consequences of C3b amplification. Alternatively, the surface can be used to selectively bind CFH for diagnostic purposes, to extract or purify CFH from a mixture, or to bind CFH to identify molecules that interact and thus bind to the captured CFH.

Suitably the protein according to the present invention can be covalently attached to the surface. There are many suitable techniques available to the skilled person to achieve covalent linking. For example, the addition of a Cys residue towards either its N or C terminus would provide a convenient method of attachment to surfaces that come into contact with blood or serum. Various Cys-modified proteins of the present invention, which retain CFH binding and activating properties, are described below.

Alternatively, the protein can be linked though non-covalent means, e.g. passive adsorption, protein/protein interactions, ionic interactions, etc. For example, a surface can be coated with biotin/avidin and the protein of the present invention can be a fusion with the corresponding biotin/avidin molecule to enable if to bind to the surface.

Known methods for modifying the surface of a medical device to facilitate protein coating include physical modification, chemical modification, photochemical modification, and plasma treatment; see, for example, Vasita, Rajesh; Shanmugam i, K; Katt, D S (2008). "Improved biomaterials for tissue engineering applications: surface modification of polymers". *Current Topics in Medicinal Chemistry* 8 (4): 341-353, and Morra, M.; Cassinelli, C. (2006). "Biomaterials surface characterization and modification". *The International Journal of Artificial Organs* 29 (9): 824-833.

In a further aspect of the present invention there is provided a medical device, wherein the surface of the medical device is at least partially coated with a protein according to the present invention.

Suitably substantially all of the external surfaces of the device (i.e. those which will be in contact with body tissues and/or fluids) are coated with the protein The medical device can be essentially any medical device which is exposed to tissues of the body of a subject, e.g. microcapsules for stem cell delivery, stents, stent grafts, orthopaedic implants, catheters, guide wires, heart valve repair devices and extracorporeal circulatory devices.

The present invention is particularly appropriate to implantable medical devices, e.g. microcapsules, stents, vascular grafts, orthopaedic implants, pacemakers and the like, as well as extracorporeal circulatory devices such as equipment used in hemodialysis, plasmapheresis, extracorporeal membrane oxygenation and related procedures.

Adsorption of proteins to the surfaces of implantable medical devices exposed to blood and consequent complement activation is a common problem, and drives inflammatory reactions.

By coating at least a portion of the surface of such a medical device with proteins according to the present invention, complement activity/activations associated with such a surface would be expected to be reduced. The immobilised protein according to the present invention would recruit factor H from the blood/serum and decrease complement activation on or associated with the surface.

In another embodiment the device can be coated with a composite of the protein of the present invention bound to CFH.

In a related aspect of the present invention, there is provided a method of treating a medical device, the method comprising:

providing a medical device;

providing a protein according to the present invention; and binding said protein to at least a portion of the surface of the medical device.

Binding of the protein according to the present invention to the medical device can, of course, be carried out by any suitable technique, including those discussed above.

In a further aspect of the present invention, there is provided a method of detecting the presence or quantity of CFH in a sample, the method comprising:

providing a sample;

providing a protein according to the present invention;

contacting the sample with the protein of the present invention; and detecting binding of the protein to the CFH present in the sample.

Suitably the protein according to the present invention could be immobilised on a surface and used to adsorb CFH in a method analogous to a conventional "ELISA". The high affinity and selectivity of PspCN makes it an attractive agent for use in quantifying levels of CFH. Examples of a protein according to the present invention being used to quantify CFH levels in normal human serum are described below.

When combined with modifications of PspCN, e.g. covalent modifications, to facilitate labelling/detection (possibly through attachment of fluorescent tags via introduced cysteine residues or other means, or through fusion with an enzyme at the level of gene expression and protein production), this makes labelled PspCN an ideal choice for quantification of CFH levels.

The method may suitably be a diagnostic method, and thus can involve detecting the presence of CFH in a biological sample from a subject, e.g. a sample of blood or a fraction of blood such as plasma. For example, CFH and a PspCN-horse radish peroxidase fusion protein could be allowed to form a complex that is then captured by an antibody and quantified. Alternatively fluorescently labelled PspCN could be used in an assay in which the formation of a complex with CFH is monitored by thermophoresis or another suitable means.

In a further aspect of the invention, there is provided a method of detecting the presence or quantity of PspCN in a sample, the method comprising:
  providing a sample;
  providing CFH;
  contacting the sample with the CFH; and
  detecting binding of PspCN to the CFH present in the sample.

The method may be a method of detecting the presence of the PspCN on a surface. The surface may be the membrane of a bacteria. Therefore, the method may be a method of detecting the presence of bacteria *Streptococcus pyogenes* or *Streptococcus pneumonia*, for example.

In a further aspect of the present invention, there is provided a method of purifying or separating CFH from a sample, the method comprising:

- providing a protein according to the present invention immobilised on a surface;
- providing a sample;
- passing the sample over the surface; and
- recovering CFH bound to the surface; and/or
- recovering the sample that is devoid or depleted of CFH.

The surface can be, for example, the surface of a container, a conduit, a matrix (e.g. a porous or fibrous matrix), beads, gels, or any packing material used in chromatography.

In a further aspect of the present invention, there is provided a method of purifying or separating PspC, PspCN or a fusion protein containing PspCN from a sample, the method comprising:

- providing CFH, or a truncated construct of CFH immobilised on a surface;
- providing a sample;
- passing the sample over the surface; and
- recovering the PspC, PspCN or fusion protein containing PspCN bound to the surface; and/or
- recovering the sample that is devoid or depleted of PspC.

The surface can be, for example, the surface of a container, a conduit, a matrix (e.g. a porous or fibrous matrix), beads, gels, or any packing material used in chromatography.

In a further aspect of the present invention, there is provided a method of coating implantable microcapsules with proteins according to the invention comprising the steps:

- providing a suitable microcapsule; and
- immobilising proteins according to the current invention onto said microcapsule.

Accordingly, microcapsules so coated have a reduced likelihood of complement activation and subsequent rejection. Examples of such microcapsules include, but are not limited to, various alginate microcapsules designed for the encapsulation of cells such as pancreatic islet cells for subsequent implantation into patients with type I diabetes mellitus.

The method may further comprise the step of providing CFH or a functional variant thereof to be bound to the protein coating the microcapsule.

The following definitions are useful for understanding the proper scope of the present invention:

"Amino acid sequence", as used herein, refers to an oligopeptide, peptide, polypeptide, or protein sequence, and fragments or portions thereof, and to naturally occurring or synthetic molecules. "Amino acid sequence" and like terms, such as "polypeptide" or "protein" as recited herein are not meant to limit the amino acid sequence to the complete, native amino acid sequence associated with the recited protein molecule.

"Cell culture", as used herein, refers to a proliferating mass of cells that may be in either an undifferentiated or differentiated state.

"Fusion protein", as used herein, refers to a protein containing amino acid sequences from each of two distinct proteins; it is formed by the expression of a recombinant gene in which two coding sequences have been joined together such that their reading frames are in phase. Hybrid genes of this type may be constructed in vitro in order to label the product of a particular gene with a protein that can be more readily assayed (for example, a gene fused with lacZ in *E. coli* to obtain a fusion protein with β-galactosidase activity). Alternatively, a protein may be linked to a signal peptide to allow its secretion by the cell. Alternatively, a protein may be linked to a peptide to facilitate purification (e.g. a polyhistidine-tag). Alternatively, a protein may be linked to a peptide to improve expression in a host cell (e.g. fusions with SUMO proteins).

The term "isolated" means a biological component (such as a nucleic acid molecule or protein) that has been substantially separated or purified away from other biological components in the cell of the organism in which the component naturally occurs, i.e., other chromosomal and extra chromosomal DMA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids, proteins and peptides.

"Nucleic acid' or 'nucleic acid sequence", as used herein, refers to a polymer of nucleotides in which the 3' position of one nucleotide sugar is linked to the 5' position of the next by a phosphodiester bridge. In a linear nucleic acid strand, one end typically has a free 5' phosphate group, the other a free 3' hydroxyl group. Nucleic acid sequences may be used herein to refer to oligonucleotides, or polynucleotides, and fragments or portions thereof, and to DNA or RNA of genomic or synthetic origin that may be single- or double-stranded, and represent the sense or antisense strand.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are mentioned in this application, and which are open to public inspection, and the contents of all such papers and documents are incorporated herein by reference.

Embodiments of the present invention will now be described, by way of non-limiting example, with reference to the accompanying drawings.

BRIEF DESCRIPTION OF THE FIGURES

FIG. 2A: Plasma-purified CFH, FIG. 2B: recombinant CFH (D1119G) and FIG. 2C: recombinant CFH (wt) at concentrations shown, all bind to immobilized sPspCN (144 RUs on an NTA/Ni$^{2+}$ sensorchip) to form stable complexes that do not dissociate appreciably over 25 minutes. The sensorchip was stripped and reloaded between the individual measurements. Calculated K$_D$ values are presented in Table 1.

FIG. 3A: A comparison of binding curves obtained for 50 nM plasma-purified CFH, CFH 8-9. CFH 8-15, CFH 10-15 (near the baseline) and CFH 19-20 (near the baseline). FIG. 3B: An expanded segment of the sensorgram in (FIG. 3A) to reveal the very low responses obtained for CFH 19-20, and CFH 10-15. FIG. 3C: A concentration series of CFH 8-9 was flowed over immobilized PspCN to allow estimations (by the equilibrium method) of a K$_D$ value (see Table 1).

FIG. 4A: Free PspCN exhibits a spectrum indicative of an unfolded protein with little chemical shift dispersion. FIG. 4B: Addition of CFH 8-9 to the PspCN sample in A causes a dramatic change in the spectrum for PspCN when bound to CFH 8-9. This spectrum of the complex shows well-dispersed sharp peaks indicative of a compact folded protein. Numerous chemical shift perturbations are evident between the spectra of free CFH 8-9 (FIG. 4C) and PspCN bound CFH 8-9 (FIG. 4D). Both CFH 8-9 spectra show well-dispersed sharp peaks indicative of a compact folded protein, however the large changes between the spectra indicate that many CFH 8-9 amino acid residues are involved in the interaction with PspCN.

(FIG. 5A) Outcome of SDS-PAGE performed on CFH and CFH:PspCN with cross-linker, BS3, indicating bands (s1-s5) subjected to mass spectrometry. MWM=molecular weight markers as indicated (kD); Lanes 1 and 2: 0.5:1 BS3:CFH yields two bands (s1,s2) corresponding to cross-linked monomeric CFH as well as a ladder of cross-linked CFH dimers/oligomers: Lanes 3 and 4: 4:1 BS3:CFH showing depletion of monomeric CFH and increased representation of presumed CFH dimer (s3) and oligomers. Lanes 5 and 6: 4:1 ratio of BS3:(CFH+PspCN) yields a single band (s4) for monomeric CFH in complex with PspC, and higher bands corresponding to dimer (s5), trimer etc. of CFH complexed with an undetermined number of PspCN molecules. (FIG. 5B) Map of clustered cross-links in s1-s5. Arcs representing cross-links within CFH are colour-coded (according to key) to indicate (i) cross-links in CFH that became more rare or were no longer detectable upon PspCN binding; (ii) cross-links that become more common or newly detectable upon dimerisation and-or PspCN binding; (iii) cross-links that showed no changes in s1-s5; (iv) cross-links unique to dimers; (v) cross-links unique to CFH:PspCN complex.

FIGS. 6A-6B: Comparison of C3b and C3d binding by CFH alone and CFH:PspcN complex. Demonstration by SPR that (FIG. 6A) Plasma purified CFH has a lower affinity for immobilized C3b than the plasma purified CFH:PspCN complex. (FIG. 6B) Plasma-purified CFH has a very low affinity for C3d (which is equivalent to the TED of C3b), but when in complex with PspCN, binds well to C3d. Calculated affinity constants are summarised in Table 2.

(FIG. 8A) SDS-PAGE showing purify of PspCN, rCFH (D1119G), along with plasma-purified CFH (Complement Technologies) and rCFH) under reducing and non-reducing conditions. (FIG. 8B) rCFH (D1119G) is equally as good as CFH at accelerating decay of C3b.Bb; PspCN boosts the decay-accelerating activity of CFH substantially more than that of rCFH (D1119G).

FIGS. 8A-8B are graphs demonstrating paroxysmal nocternal haemoglobinurea (PNH) rescue using proteins of the present invention. Erythrocytes were treated with AET to make 'PNH-like' cells. PNH-like cells are susceptible to acidified serum lysis in a similar way to PNH erythrocytes.

FIGS. 10A-10F show sensorgrams showing the binding affinities of the fragments PspC (52-140) (FIG. 10A), PspC (62-140) (B FIG. 10B), PspC (72-140) (FIG. 10C), for PspC (37-130) (FIG. 10D), PspC (37-120) (B FIG. 10E), and PspC (37-110) (FIG. 10F).

FIG. 17 shows that highly purified CFH can be produced by using immobilised cysteine tagged PspCN in a one step method.

FIG. 20A: sensorgrams for immobilised TIGR4 residues 37-179. FIG. 20B: sensorgrams for immobilised TIGR4 residues 68-148. In each case the sensorgrams indicate a similar irreversible manner to that of the D39 strain and $K_D$s of $1\times10^{-16}$ M and $8\times10^{-16}$ M were calculated for TIGR4 residues 37-179 and 68-148 respectively and indicates a similar mechanism of binding.

FIG. 22A: Sensorgrams showing FH and FH:TIGR4 (residues 37-179) binding to coupled C3b;

FIG. 22B: Sensorgrams showing FH and FH:TIGR4 (residues 37-179) binding to coupled C3d;

FIG. 22C: Sensorgrams showing FH and FH:TIGR4 (residues 68-148) binding to coupled C3b and FIG. 22D: Sensorgrams showing FH and FH:TIGR4 (residues 68-148) binding to coupled C3d. It is clear that as is the case for PspCN from *S. pneumonia* strain D39, binding of uncompleted FH to C3d is negligible, whereas FH complexed with PspCN causes a significant increase in C3b affinity and a large increase in C3d affinity. $K_D$s for these interactions are listed in Table 3.

SPECIFIC DESCRIPTION OF EMBODIMENTS OF THE INVENTION

Figure 1:
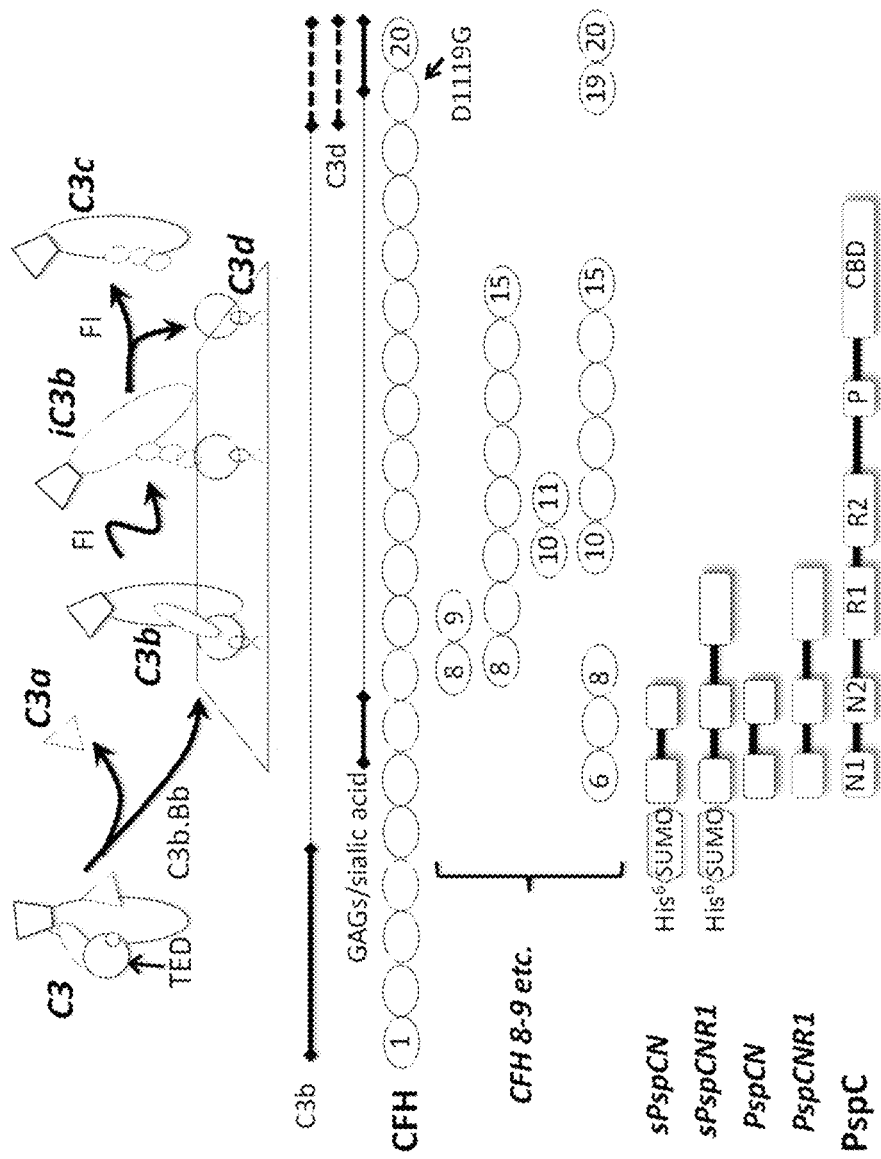
FIG. 1. Proteins and complexes investigated in this study. Top: C3 convertase, C3b.Bb (formed by CFD-catalysed proteolysis of the C3b:CFB proconvertase complex), cleaves C3 to C3b plus C3a; C3b attaches to surfaces via its thioester domain (TED). It may be degraded to iC3b plus C3f by complement factor I (CFI) in a reaction requiring CFH or other (membrane-associated) cofactors, then to C3c plus C3d(g). C3d(g) is degraded to C3d, which corresponds to the TED of C3b. Middle: Human CFH (20 CCPs shown as ovals) was purified from plasma while recombinant (r)CFH (and rCFH (D1119G)) were produced from *Pichia pastoris*, as were the various rCFH fragment shown. All *P. pastoris*-produced glycoproteins were treated with Endo H$_f$ prior to final purification. Binding sites on CFH for some ligands are indicated (dotted line implies they are occluded as discussed in text). Bottom: Recombinant (*Escherichia coli*-produced) sPspCN and sPspCNR1 are N-terminally hexaHis-tagged SUMO-fusions of polypeptides corresponding to residues 37-140 and 37-292 of PspC, respectively; the cleaved version is designated PspCN (R1 and R2 are repeats 1 and 2; CBD is the choline-binding domain).

The present inventors have discovered that proteins of the present invention have the ability to attach to the key regulator of the alternative pathway of complement activation, human complement factor H (CFH), in a manner that is effectively irreversible on the biological timescale (hours to days). Furthermore the PspCN-bound CFH has at least a three-fold higher affinity for its natural ligand C3b and has a very much greater affinity for C3d (an important degradation product of C3b).

The affinity between CFH and PspCN is so strong that it effectively permanently couples PspCN to Factor H. Presumably this explains the employment by *S. pneumoniae* of PspC to protect itself against complement-mediated destruction (see below). The ability of PspC to activate CFH makes it an even more effective means of self-protection.

Thus PspCN and other proteins according to the present invention represent an elegant way of capturing CFH in a highly bioactive form. If PspCN were immobilised it could be used for isolating CFH from complex mixtures such as serum.

This ability of PspCN to both bind CFH and also to enhance its affinity for its ligands, and hence its regulatory activity, also suggests its potential use as a therapeutic agent for conditions where the primary aetiology is underactivity of CFH. Such conditions include atypical haemolytic uremic syndrome (aHUS), dense deposit disease (DDD) and age-related macular degeneration (AMD).

Modifications to this sequence could be made to facilitate the attachment of labelling/detection tags or for covalent surface attachment.

Example 1—An "Active" Conformation of Human Factor H is Stabilized upon its Irreversible Capture by *Streptococcus Pneumoniae* Protein PspC Introduction The complement system is the name given to a set of 40-50 blood proteins in vertebrates that cooperate amongst themselves, and with other immune components, to recognize, tag and eliminate potentially dangerous materials such as foreign cells and the products of apoptosis and oxidative damage[1]. Strategies employed by bacteria to evade the complement system are potential targets for novel antibiotics and vaccines, while therapeutic modulation of the complement system is being actively explored in a wide range of clinical contexts[2].

Central to all the pathways that activate the complement system is a rare example of a positive-feedback loop in which the opsonin and pro-inflammatory protein molecule, C3b, is amplified through formation of the C3b.Bb complex that enzymatically cleaves molecules of C3 to form the anaphylatoxin C3a plus additional C3b (FIG. 1)[3]. Nascent C3h has a transient ability to covalently bind, via a thioester-containing domain (TED), to any local surface[4]. Thus both host (or 'self') and foreign (or 'non-self') surfaces are potentially at risk of becoming coated with C3b molecules.

Complement factor H[5-8], which is composed of 20 CCPs[9, 10], is an important soluble regulator of this key event since if competes with complement factor B (CFB, the precursor of Bb) for binding to C3b, accelerates irreversible dissociation (also known as decay) of the C3b.Bb complex, and is a cofactor for complement factor I (CFI)-catalysed cleavage of C3b to form iC3b that cannot bind to CFB but (like the further sequential surface-bound proteolytic degradation products, C3dg and C3d) continues to function as an opsonin. The final cleavage product, C3d, equaling to the TED of C3b (FIG. 1), remains chemically attached to the surface for the long term. Via ligation of complement receptor-type 2 on B-cells, the presence of iC3b or C3d(g) lowers the threshold for antibody production[11]. Thus CFH is critical for self versus non-self discrimination by the complement system since it prevents C3b amplification both in fluid phase and on self-surfaces and facilitates iC3b/C3d (g) production, yet if allows opsonisation, release of anaphylatoxins, and cell lysis to proceed elsewhere.

The importance of CFH for modulation of C3b amplification is underlined by the links between allelic variations in the CFH gene and the risk of a range of diseases associated with an improperly regulated complement system[12]. The common (one out of every three alleles) "haplotype 2" of CFH is responsible for an estimated 50% of the risk of age-related macular degeneration[13]; it includes the substitution of histidine for tyrosine at position 402 in CCP 7 that contributes to the recognition by CFH of self-surface specific molecular markers (such as GAG chains and sialic acid clusters)[14-17]. Mutations linked to the potentially fatal kidney disease, atypical haemolytic uraemic syndrome (aHUS) occur throughout CFH, but are clustered in CCPs 19 and 20[18] that likewise contribute to surface recognition but also contain a binding site for C3b and its degradation products[15]. The N-terminal four CCPs of CFH bind C3b (but not iC3b or C3d), are required for both cofactor and decay-acceleration activity[19], and harbour mutations and SNPs linked to age-related macular degeneration (AMD), aHUS and membranoproliferative glomulonephritis type II[20]. Potentially therapeutic proteins designed to incorporate CCPs 1-4[21], or both CCPs 1-4 and CCPs 19-20[22, 23], are at various stages of development.

As the chief soluble regulator of the complement system, CFH is inevitably susceptible to microbial hijack. It is not surprising that many bacterial surface proteins bind to plasma CFH[24, 25]. For example, the sub-capsular protein PspC from the nasopharyngeal commensal bacterium *Streptococcus pneumoniae* (also called SpsA, CbpA, and Hic) captures host-derived CFH on the capsid surface[26-28]. Invasion of the lower respiratory tract or blood by *S. pneumoniae* can cause pneumonia, meningitis and septicaemia. There is a growing and worrying recognition that vaccine-resistant strains may colonise the nasopharyngeal tract, taking the place of strains whose capsular serotypes are present in vaccines [Weinberger D M, Malley R, Lipsitch M. Serotype replacement in disease after pneumococcal vaccination. Lancet, 2011 Dec. 3; 378(9807):1962-73. doi:10. 1016/S0140-6736(10)62225-8]. It is thus of great interest that serotype invasiveness seems to be determined mainly by the ability to bind CFH. Differences in production levels, or allelic variation, of the PspC are likely responsible for these variations in CFH capture[29].

An intriguing aspect of CFH is that its regulatory properties are modulated according to C3b context. In the fluid-phase, CFH restricts C3b production to a level required for immune surveillance (via the transient ability of nascent C3b to bind covalently to any local surface) but—importantly—prevents runaway activation that would deplete plasma C3 and factor B[3, 30]. On the surfaces of healthy host tissue, CFH collaborates with membrane-bound regulators[31] to shut down C3b amplification almost entirely. On the other hand, moderate levels of C3b deposition and iC3b formation are facilitated by CFH in the case of senescent or damaged cells and cell debris, leading to non-inflammatory clearance[32-34]. Finally, CFH does not suppress C3b amplification on bacterial cells (lacking CFH-binding proteins or other counter-complement measures) thereby permitting a full-blown onslaught by the complement system on a microbial invader involving very rapid opsonisation, the release of pro-inflammatory C3a and C5a, and cytolysis.

Why does CFH activity vary according to the context of C3b (and C3b.Bb)? This seems unlikely to be merely a matter of selective enrichment of CFH concentrations at those surfaces requiring protection, since such a mechanism would leave CFH highly vulnerable to being exploited by microbes. The inventors set out to test whether an evolutionary arms race between host and pathogens could shed light on the little-understood relationship between the structure of CFH and its function as a self-surface specific regulator of C3b amplification. According to one hypothesis, the fact that only six or seven out of a total of 20 CCPs in the CFH molecule—located towards both its H and C termini—engage with ligands directly[15] is readily explained if most or all of the remaining 13 or 14 CCPs act to make CFH less susceptible to successful hijacking by bacterial proteins. Thus, according to this idea, mere enrichment at the bacterial surface (or the host surface) would be insufficient for effective bacterial (or host cell) protection. Instead, the full regulatory potential of CFH could only be revealed following a conformational rearrangement brought about via interaction with specific self-surface molecular signatures, or their mimics on bacterial surfaces. To test this hypothesis the inventors explored the interaction between CFH and PspC. This revealed that PspC binds extremely tightly to CFH and stabilizes a rearrangement of CCPs that reveals the previously occluded C3b/C3d-binding site located close to its C-terminus. The inventors suggest that other bacterial proteins, and indeed host-surface molecular markers, may also act to stabilize this "activated" form of CFH.

Materials and Methods

Preparation of Proteins

Human complement proteins—purified from pooled plasma—were obtained from Complement Technologies Inc. (Tyler, Tex.), stored according to the supplier's instructions, and freshly thawed before being diluted and used without further purification. A library of recombinant CFH module-truncation mutants ("fragments", see FIG. 1) had been prepared from *Pichia pastoris* and characterized as described previously[35] and stored at −80° C.

Full-length recombinant human CFH, with a wild-type sequence (CFH (wt)), was produced in recombinant *P. pastoris* grown in a fermenter and purified in an enzymatically deglycosylated form as described previously[35]. Expression-optimised DNA encoding the D1119G mutant of CFH (CFH (D1119G)) was synthesised by Geneart-LifeTech and sub-cloned into the *P. pastoris* expression vector pPICZαB. Production and purification of CFH (D1119G) was subsequently performed as described previously for CFH (wt).

Figure 14:
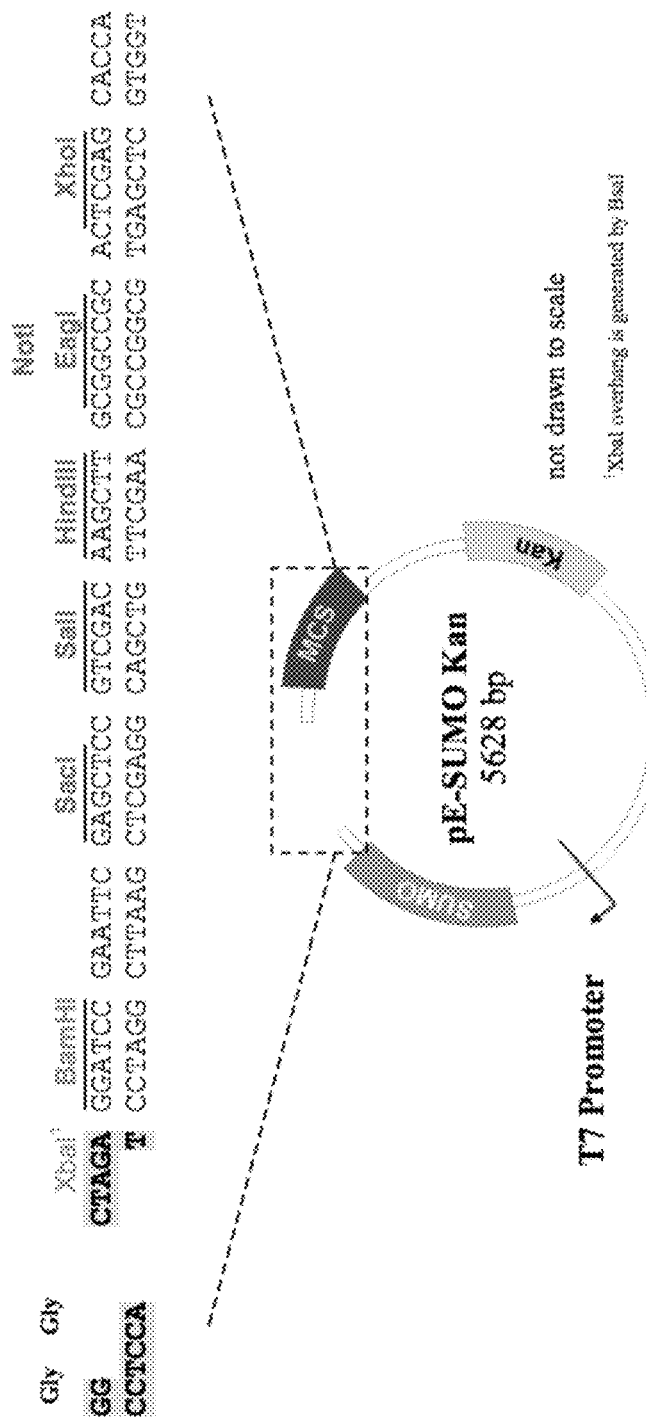
FIG. 14 shows a schematic of plasmid pE-SUMO Kan, which was used to express SUMO-fusion proteins according to the present invention (www.lifesensors.com).

A gene representing residues 37-140 of PspC (D39) was optimised for expression in *Escherichia coli* (see SEQ ID NO 4 below) and purchased from GeneArt-LifeTech. The resulting construct was then cloned into the pE-SumoPro-Kan *E. coli* expression vector (LifeSensors, Malvern, Pa., see FIG. 14) and expressed in BL21 (DE3) *E. coli* in lysogeny broth (LB). Protein production was induced overnight at 25° C. by the addition of 0.25 mM isopropyl β-D-1-thiogalactopyranoside (IPTG). The resultant hexaHis-SUMO-tagged protein was named "sPspCN" and was captured on a HisTrap immobilised $Ni^{2+}$-affinity column (GE Healthcare) and eluted with a linear gradient of 0-0.5 M imidazole. Samples of sPspCN were further purified by size-exclusion chromatography on a HiPrep Superdex 75 column (GE Healthcare) equilibrated with phosphate-buffered saline (PBS). A similar strategy was used to prepare a longer construct, embracing the adjacent R1 domain (see FIG. 1). (residues 37-292) called sPspCNR1.

For most experiments, the catalytic domain from the SUMO-specific protease, ULP1, was used to remove the hexaHis-SUMO tags from sPspCN (or sPspCNR1) (with no vector-derived residues), following which the tag was removed by a second $Ni^{2+}$-affinity chromatographic step. The cleaved material—PspCN (or PspCNR1)—was then purified further on a HiPrep Superdex 75 column in PBS as above. Proteins were judged to be homogeneous by SDS-PAGE and the integrity and identity of the proteins was confirmed by mass spectrometry (not shown).

SPR-Derived Measurement of CFH Binding to sPspCN

All surface plasmon resonance experiments were performed at 25° C. on a Biacore T200 instrument (GE Healthcare) using 10 mM HEPES, 150 mM NaCl, 0.05% v/v surfactant P20, pH 7.4 (HBS-P$^+$) supplemented with 50 M ethylenediaminetetra-acetic acid (EDTA). $Ni^{2+}$ (51 RU) and subsequently sPspCN (144) (via its N-terminal hexaHis-SUMO tag) were immobilised on a Biacore NTA sensorchip. Aliquots from a solution of full-length CFH (from plasma or from recombinant *P. pastoris*), or CFH fragments, were flowed over the chip at the concentrations shown for 180 s at 100 μl/min, followed by a dissociation phase of 1500 s. Due to irreversible binding by CFH, the sensor chip was regenerated between measurements by two 30 s injections of 350 mM EDTA in 1 M NaCl, followed by 30 s injections of 50 mM NaOH, then 0.5 (w/v) % sodium dodecylsulfate (SDS). Data were analysed using the Biacore evaluation software, the curves were fitted and kinetic parameters estimated on the basis of a 1:1 binding model.

The use of an NTA sensorchip to measure the affinity of CFH for sPspCN avoided the need for amine coupling with its associated potential for heterologous deposition of the protein and the danger of masking ligand-recognition sites. Moreover, it allowed for relatively straightforward regeneration of the SPR sensorchip surface between measurements. The disadvantages of this method were gradual leaching of the hexaHis-tagged analyte from the chip surface, and the potential for CFH and its fragments to bind directly to $Ni^{2+}$ (Nan R, Gor J, Lengyel I, Perkins S J. Uncontrolled zinc- and copper-induced oligomerisation of the human complement regulator factor H and its possible implications for function and disease. J Mol Biol. 2008 Dec. 31; 384(5):1341-52.). Indeed we observed (data not shown) weak binding of CFH to the loaded NTA sensorchip surface (no PspCN present) and light binding of CFH 6-8 to this surface. These difficulties were largely circumvented by background subtraction.

SPR Measurement of C3b, C3c and C3d Binding Affinities

Experiments were performed as above except C3b (272 RU); C3c (166 RU) and C3d (69 RU) were immobilized, using standard amine coupling, on three different flow cells of a Biacore C1 sensorchip (the fourth flow cell was used for background subtraction). Factor H (pre-incubated with or without a twofold molar excess of PspCN) was injected over the chip at the concentrations shown (90 s, 30 μl/min), followed by a dissociation phase of 400 s. The sensor chip was regenerated by 2×30 s injections of 1 M NaCl. Data were analysed using the Biacore evaluation software and equilibrium affinity parameters were calculated using a 1:1 binding affinity model.

Decay-Accelerating Assay

The decay acceleration activity of CFH or CFH:PspCN was measured in an SPR-based assay as described previously. In brief, 535 RU of C3b was immobilised on a Biacore CM5 sensorchip via standard amine coupling. Subsequently, C3 convertase (C3b.Bb) was assembled on the chip by a 120 s at 10 μl/min injection of CFB plus CFD (500 nM+50 nM respectively). Formation of C3b.Bb (to 145 RU) was observed (by SPR) followed by an initial dissociation phase (200 s) to allow monitoring of the rate of intrinsic C3 convertase decay (departure of Bb). After this, CFH or CFH:PspCN complex were injected (120 sat 10 μl/min) at the concentrations shown followed by a further dissociation phase. The chip was regenerated between cycles by a 30 s injection of 0.2 μM CFH, followed by two 30 s injections of 1 M NaCl.

Haemolytic Assay

Sheep and rabbit whole blood were purchased from TCS Biosciences (Buckingham, UK) and CFH-depleted serum was purchased from Complement Technology. The haemolysis assay was performed in 96-well plates, based on a method described by Pangburn[36], except HEPES was used in place of the more traditional veronal buffer[27]. Erythrocytes from 5 ml of whole blood were washed three times with 20 mM HEPES; 145 mM NaCl; 10 mM EDTA; 0.1% (w/v) gelatin (porcine skin, Fluka), pH 7.3 (Buffer H1), and a further three times with 20 mM HEPES; 145 mM NaCl; 100 μM EDTA; 0.1% (w/v) gelatin, pH 7.3 (Buffer H2). CFH-depleted serum was reconstituted with CFH construct to 2 μM and used at the final concentrations indicated. Erythrocytes were used at a concentration that gave a final $A_{412}$ of 1 (rabbit) or 1.2 (sheep) when lysed completely with water. Serum reconstituted with CFH was then combined on ice, to the final concentrations indicated, with erythrocytes and Buffer H2 to yield a final volume of 45 μl. Lysis was initiated by the addition of 5 μl of a solution of 50 mM $Mg^{2+}$, 50 mM ethylene glycol tetraacetic acid, pH 7.3. The reaction was incubated at 37° C. for 30 minutes whereupon it was quenched by the addition of 200 μl of Buffer H1. Unlysed cells were subsequently pelleted by centrifugation at 1500 g for 10 minutes at 4° C., then 100 μl of supernatant was removed and the $A_{412}$ recorded.

Heparin-Affinity Chromatography

Protein samples (~0.5 M) were applied to a 1-ml HiTrap Heparin chromatography column (GE Healthcare) in 20 mM potassium phosphate, pH 7.5, and eluted with a linear gradient of 1 M NaCl over 20 column volumes.

Nuclear Magnetic Resonance Spectroscopy

NMR spectra were acquired on an Avance II 800 MHz spectrometer (Bruker) equipped with a 5-mm TCI Cryo-Probe (Bruker). NMR data were processed using TopSpin 3.1 (Bruker) and analysed using the CCPNMR Analysis software suite [Vranken W F, Boucher W, Stevens T J, Fogh R H, Pajon A, Llinas M, Ulrich E L, Markley J L, Ionides J, Laue E D. The CCPN data model for NMR spectroscopy: development of a software pipeline. Proteins. 2005 Jun. 1; 59(4):687-96.] Samples of $^{15}$N-labeled FH 8-9 and $^{15}$N-labeled PspCN were used to optimize conditions by varying NaCl concentrations from 0-150 mM, pH from 4-6.5, and temperature from 15° C.-70° C. Subsequently, a sample of 40 μM $^{15}$N-labeled FH 8-9 in 20 mM potassium phosphate pH 6.2, was used to record a $^1$H, $^{15}$N HSQC spectrum at 310 K and then PspCN was added to a final concentration of 100 μM and the spectrum was re-recorded. In a separate experiment, a sample of 30 μM $^{15}$N-labeled PspCN in 20 mM potassium phosphate, pH 6.0, was used to record a $^1$H, $^{15}$N HSQC spectrum at 298 K and then FH 8-9 was added to a final concentration of 40 μM and the spectrum re-recorded.

Cross-Linking and Mass Spectrometry (MS)

Freshly thawed samples of either plasma-purified CFH (20 μg) or plasma-purified CFH plus PspCN (20 μg CFH, a 1:1.15 molar ratio to PspCN) were cross-linked with bis [sulfosuccinimidyl] suberate (BS3) using a 1:4 mass ratio of protein-to-BS3, and a final [CFH]=0.56 μg/μl in the reaction mixtures. The products of cross-linking were subjected to sodium dodecyl sulfate-polyacrylamide gel electrophoresis (SDS-PAGE) [(NuPAGE 4-12%, Bis-Tris gel with MOPS running buffer (Invitrogen)]. Gel bands were stained with Instant blue (Expedeon), and bands corresponding to five different cross-linking products (see FIG. 5A) were selected and cut from the polyacrylamide gel. These were subjected to in-gel tryptic digestion as described [Chen Z A, Jawhari A, Fischer L, Buchen C. Tahir S, Kamenski T, Rasmussen M, Lariviere L, Bukowski-Wills J C, Nilges M, Cramer P, Rappsilber J. Architecture of the RNA polymerase II-TFIIF complex revealed by cross-linking and mass spectrometry. EMBO J. 2010 Feb. 17; 29(4):717-26.]. For each sample, cross-linked peptides were fractionated using a SCX-StageTip [Ishihama Y, Rappsilber J, Mann M. Modular stop and go extraction tips with stacked disks for parallel and multidimensional Peptide fractionation in proteomics. J Proteome Res. 2008 April; 5(4):988-94.]; non-cross-linked peptides should elute primarily at low salt (60 mM ammonium acetate) while cross-linked peptides should be enriched in the high-salt fraction (500 mM ammonium acetate). The high-salt fractions were analyzed by liquid chromatography-MS/MS using a Q Exactive instrument (Thermo Fisher Scientific). Peptides were separated on an analytical column packed with C18 material (ReproSil-Pur C18-AQ 3 μm; Dr Maisch GmbH, Germany) into a PicoTip emitter (New Objective, Woburn, Mass.). A linear gradient was applied running from 1.6% (v/v) aqueous acetonitrile to 32% (v/v) acetonitrile in water over 109 minutes, followed by a rapid increase to 76% (v/v) acetonitrile. Mass spectrometry acquisitions were conducted in a data-dependent setup: following each MS1 scan, the ten most intense ions were isolated and fragmented by higher-energy C-trap dissociation. Both MS1 and MS2 spectra were recorded in the Orbi-trap analyzer with 70000 resolution for MS1 scans and 35000 for MS2 scans. "Dynamic exclusion" was set to 60 s and "repeat count" was 1.

Cross-linked peptides were identified using in-house written software. In total 50 linkages were identified from these five samples. Label-free quantitation was carried out at linkage level as follows. For each unique linkage, mass spectrometric chromatographic signal intensities of all corresponding cross-linked peptides were retrieved using Pinpoint software (Thermo Fisher Scientific) and summed. To ensure that a fair comparison across samples was achieved, the signal intensify of individual linkage pairs were normalized using the summed signal intensity of 23 cross-linkages and 29 non-cross-linked CFH peptides that were observed in all five samples. The intensity variation of a cross-linkage across the five samples was thereby reflected in its relative intensity within each sample, which was calculated as the logarithm to base 5 of the quotient of the observed intensity and the average intensity of this cross-link in five samples. Furthermore, using Cluster 3.0 [de Hoon M J, Imoto S, Nolan J, Miyano S. Open source clustering software. Bioinformatics, 2004 Jun. 12; 20(3):1453-4.], the 50 observed cross-links were clustered, based on their relative intensities in the five samples, in order to elucidate the correlation between their intensity variation and locations. These cross-links were not evenly distributed along the sequence of CFH and the bias in their locations afforded valuable insight into the conformation of full-length CFH and its conformational changes upon interaction with PspCN.

Results

The N-Terminal Region of PspCN Binds Irreversibly to CFH

Figure 2A:
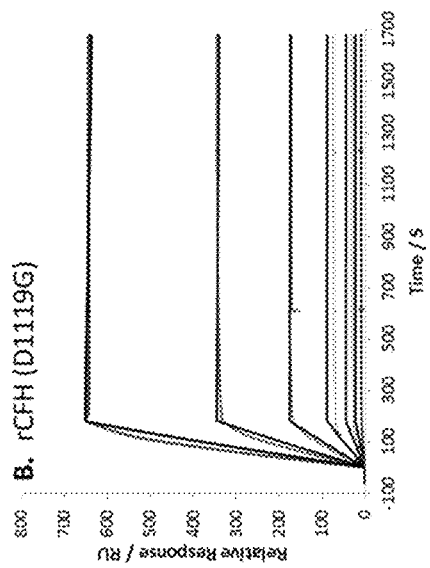
FIGS. 2A-2C. PspCN forms a stable complex with CFH.
Figure 2B:
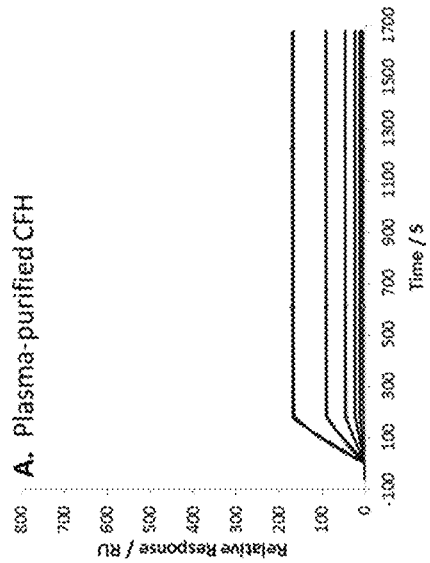
Figure 2C:
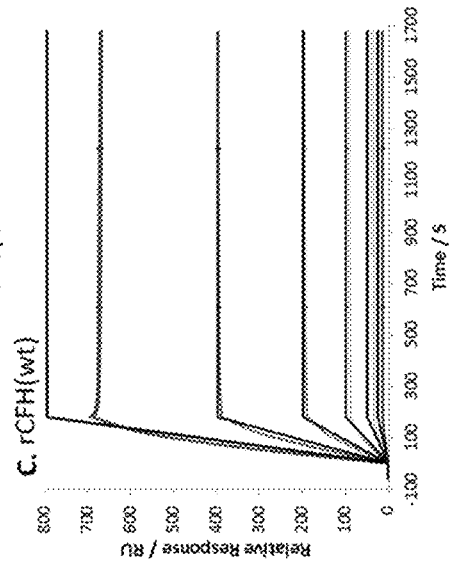

The N-terminal region of PspC from *S. pneumoniae* (strain D39) (FIG. 1) had previously been shown (Dave S, et al. Indian J Med Res. 2004 May; 119 Suppl:66-73, and Hammerschmidt S. et al. The host immune regulator factor H interacts via two contact sites with the PspC protein of *Streptococcus pneumoniae* and mediates adhesion to host epithelial cells. J Immunol. 2007 May 1; 178(9):5848-58) to contain the CFH-binding site but its precise boundaries remained ill defined. We produced in *E. coli* two H-terminally hexaHis-SUMO tagged proteins corresponding to PspC residues 37-140 (sPspCN) and 37-292 (sPspCNR1) (i.e. including the R1 domain, FIG. 1). Using SPR we found that neither the SUMO fusion partner (data not shown) nor the presence of the R1 domain (data not shown) significantly influenced binding to CFH or CFH fragments. SUMO itself did not bind to CFH (data not shown). We prepared concentration series and used SPR to measure the affinities of plasma-purified CFH and recombinant CFH (from *P. pastoris*)[35] for sPspCN immobilized on a carboxymethylated dextran-coated chip pre-immobilized with nitrilotriacetic acid (NTA) and loaded with Ni$^{2+}$ (FIGS. 2A-2C, Table 1). In both cases, binding was effectively irreversible with off-rates too slow to measure and sub-pM $K_D$s. The bound CFH could not be removed by high-salt washes; only by stripping the NTA chip with sequential treatments of EDTA, NaOH and SDS solutions could the sPspCN-coated surface be regenerated between measurements. Nonetheless, the regenerated sPspCN-coated surfaces were reproducible within two response units.

TABLE 1

| Construct | PspCN (D39 37-140) | | | PspCN (TIGR4 37-179) | | | PspCN (TIGR4 68-148) | | |
|---|---|---|---|---|---|---|---|---|---|
| | $k_a$ | $k_d$ | $K_D$ | $k_s$ | $k_e$ | $K_C$ | $k_a$ | $k_d$ | $K_D$ |
| Plasma CFH | 9.7e+6 | 4.4e−7 | 4.5e−14 | 1.0e+6 | 1.3e−10 | 1.4e−16 | 5.5e+5 | 4.3e−10 | 7.8e−16 |
| rCFH | 1.7e+11 | 8.8e−3 | 5.3e−14 | | | | | | |
| rCFH-D1119G | 4.1eE+6 | 4.7e−5 | 1.2e−11 | | | | | | |
| CF8-15 | 1.2e+5 | 1.5e−4 | 1.3e−9 | | | | | | |
| CFH 8-9 | — | — | 2.6e−8 | | | | | | |

TABLE 2

| | C3b | | | C3d | | |
|---|---|---|---|---|---|---|
| Construct | $K_D$/M | SE($K_D$) | Chi$^2$/RU$^2$ | $K_D$/M | SE($K_D$) | Chi$^2$/RU$^2$ |
| Plasma CFH | 4.9e−7 | 6.0e−8 | 9.1 | N/A | N/A | N/A |
| Plasma CFH: PspCN | 1.6e−7 | 1.8e−8 | 40.3 | 2.3e−6 | 1.6e−7 | 0.4 |
| rCFH | 5.8e−7 | 9.3e−8 | 29.8 | N/A | N/A | N/A |
| rCFH:PspCN | 1.6e−7 | 2.2e−8 | 81.4 | 2.1e−6 | 2.0e−7 | 4.2 |
| rCFH-D1119G | 5.4e−7 | 9.3e−8 | 9.4 | N/A | N/A | N/A |
| rCFH-D1119G: PspCN | 3.2e−7 | 4.2e−8 | 12.6 | N/A | N/A | N/A |

PspCN Binds to a Central Site in CFH

PspC was previously reported to bind to various sites of CFH including CCPs 8-11, 13-15 and 19-20 (Dave S, et al. 2004 Mayand Hammerschmidt S, et al., 2007); Duthy T G, et al. Infect Immun. 2002 October; 70(10):5604-11). We revisited this issue using sPspCN with relevant recombinant CFH fragments from our library[15] (FIG. 1). It emerged (not shown) that CFH 6-8 (i.e. the recombinant construct corresponding to CFH CCPs 6-8) bound more strongly to the Ni$^{2+}$ on the NTA chip than full-length CFH or any other tested fragment but this was not investigated further.

We found (FIGS. 3A-3C, Table 1) that CFH 8-15 binds to sPspCN very tightly ($K_D$=1-2 nM) and the sPspCN:CFH 8-15 complex dissociates very slowly although it is not as stable as the sPspCN CFH complex. On the other hand both CFH 10-11 (data not shown) and CFH 10-15 had negligible affinity for sPspCN, implying that CCPs 8 and 9 are crucial for binding.

Figures 3A, 3B, 3C:
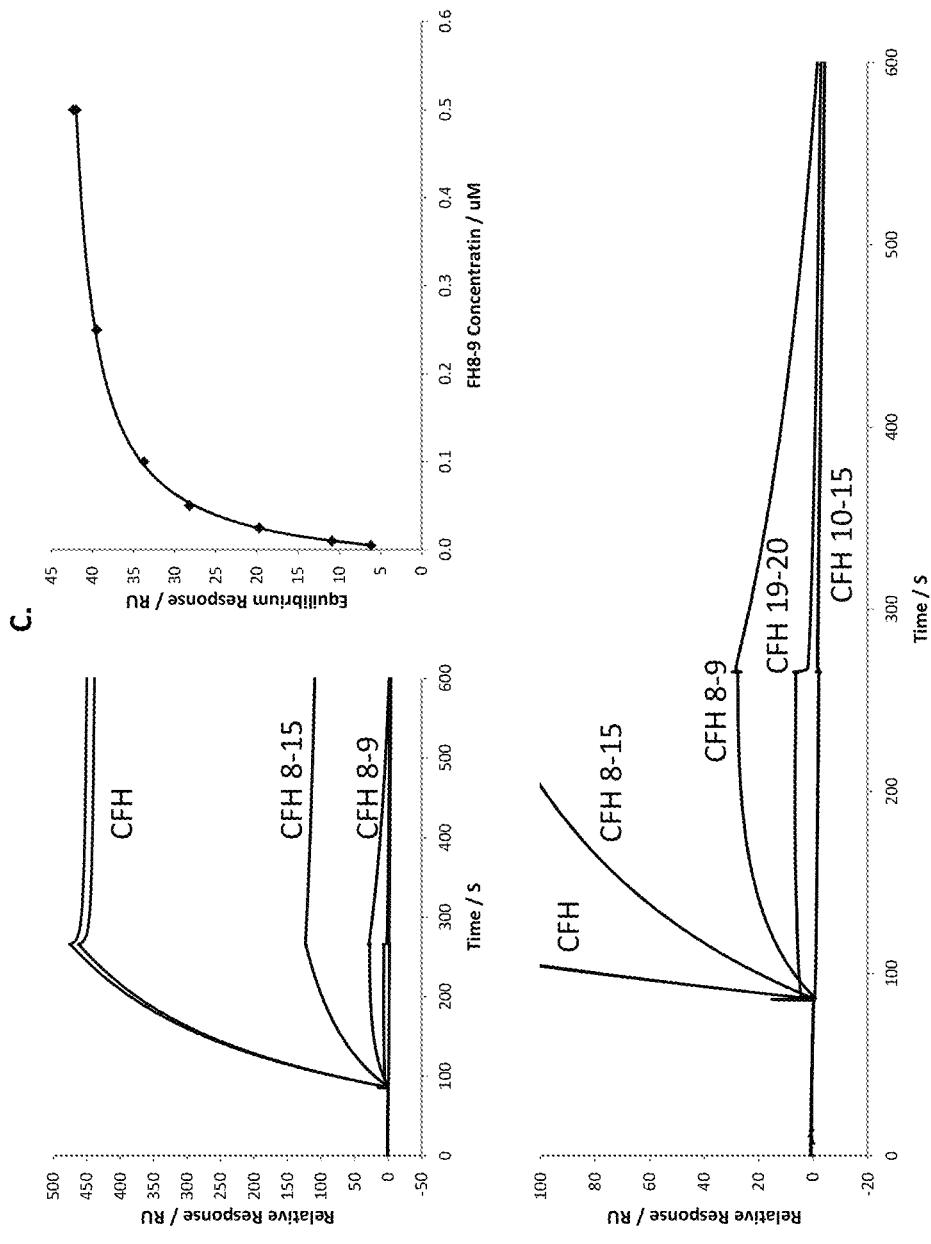
FIGS. 3A-3C, PspCN binds primarily to CCPs 8 and 9. The sensorchip bearing sPspCN was prepared as in FIGS. 2A-2C.

Indeed the double module CFH 8-9 also bound tightly ($K_D$=~26 nM) with a relatively slow off-rate. There was no evidence of sPspCN binding by CFH 6-8 (after allowing for its affinity for the Ni$^{2+}$-loaded NTA sensorchip surface, data not shown), while CFH 19-20 bound transiently and far more weakly then CFH 8-9 or CFH 8-15 (FIGS. 3A-3C).

Figures 4A, 4B, 4C, 4D:
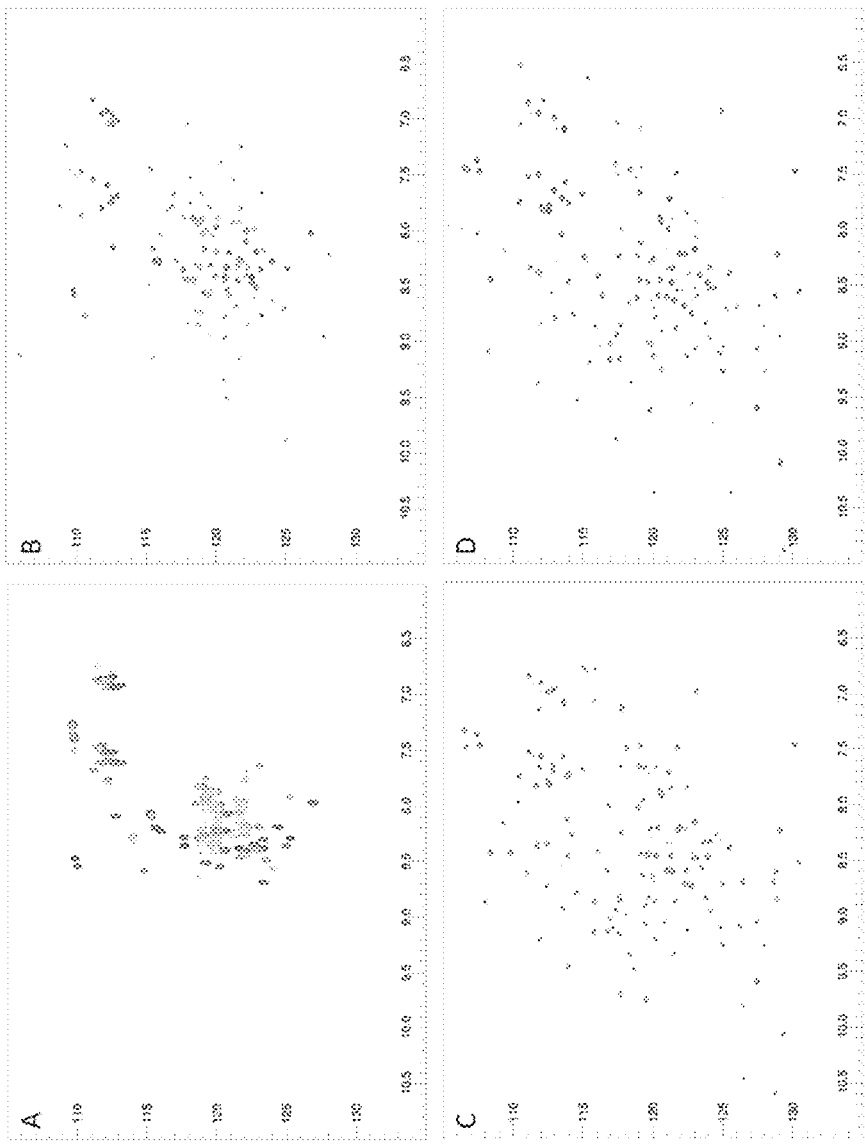
FIGS. 4A-4D. A large contact surface in complex of CFH 8-9 with PspCN is indicated by comparison of $^1$H, $^{15}$N HSQC (NMR) spectra.

That PspCN interacts tightly with CCPs 8-9 suggested burial of a substantial intermolecular interface upon complex formation. To investigate further, we recorded a $^1$H, $^{15}$N HSGC NMR spectrum of $^{15}$N CFH 8-9 with and without unlabeled PspCN. This revealed the expected very large number of $^1$H and $^{15}$N chemical-shift perturbations (FIG. 4A). Intriguingly, the $^1$H, $^{15}$N HSQC spectrum of isotopically labeled PspCN was not consistent with folded protein prior to addition of CFH 8-9. Molten globule-like characteristics of PspCN were confirmed by its propensity for B-anilino-1-naphthalenesulfonic acid binding (data not shown). Upon complex formation with FH 8-9 the bound PspCN yielded an $^1$H, $^{15}$N HSQC spectrum characterised by well-dispersed and resolved, relatively sharp, cross peaks. It seems that PspCN exists as a folded protein when in complex with CFH 8-9 (FIG. 4B).

Figures 5A, 5B:
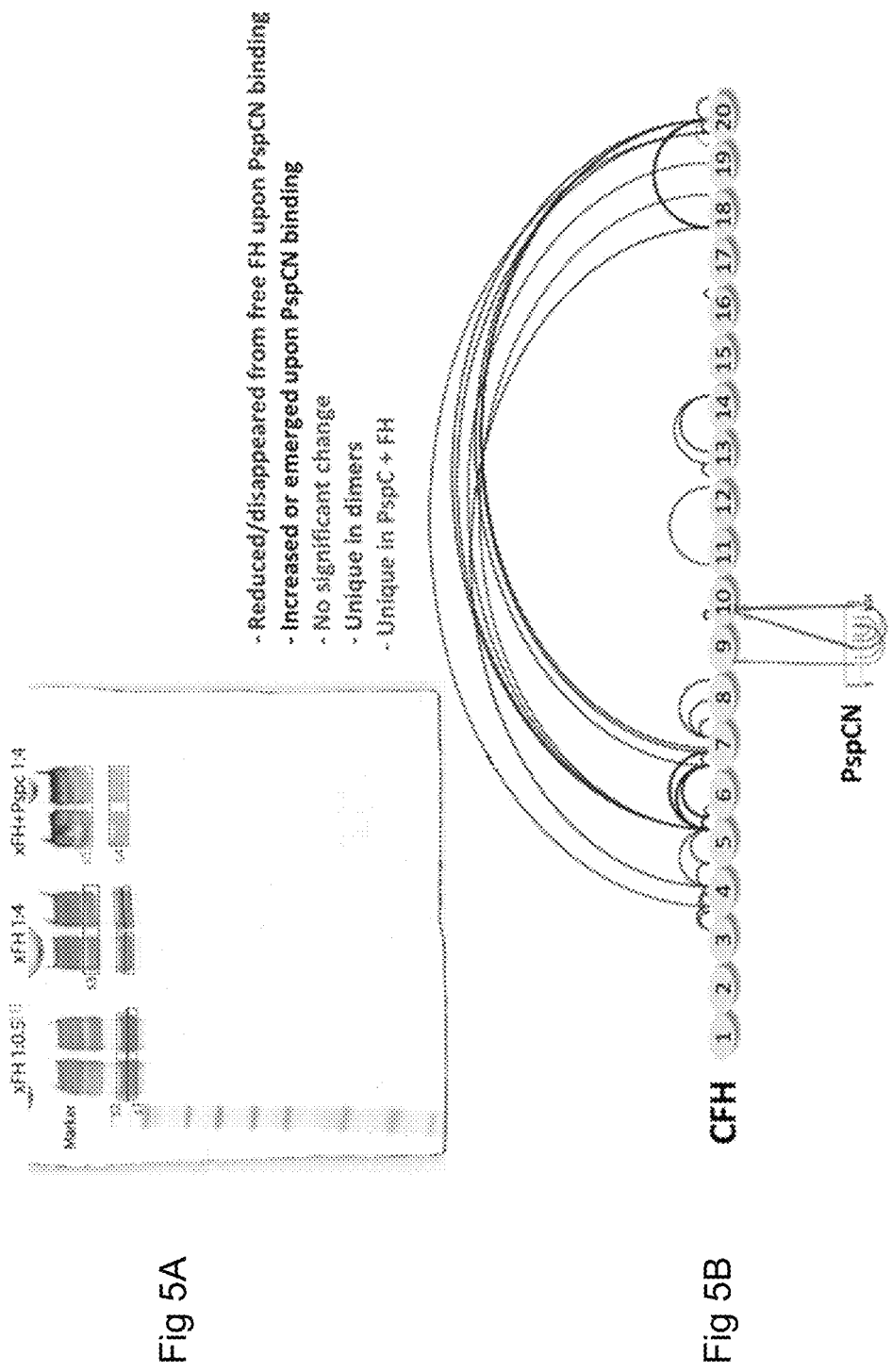
FIGS. 5A-5B. PspCN stabilizes new conformation of CFH.

To interrogate the structure of the complex formed by PspCN and full-length CFH we used a combination of chemical cross-linking and mass spectrometry (MS). To samples of plasma-purified CFH mixed with PspCN we added BS3, which is homobifunctional and forms cross-links between primary amines that are up to 11.4 Å apart. We then resolved cross-linked products by SDS-PAGE, excised the bands and subjected them to tryptic digestion. Then we applied MS/MS to identify pairs of cross-linked peptides. Within the cross-linked product that migrated on SDS-PAGE as though it had a molecular weight (MW) corresponding to a 1:1 PspCN:CFH complex (Band s4, FIG. 5A), five intermolecular cross-links were identified between peptides in PspCN and peptides in CFH; these were all located in CCPs 9 or 10 (FIG. 5B). This result is entirely consistent with our studies (above) using CFH fragments.

While these experiments do not exclude the direct participation of other CCPs, taken together they imply that CCPs 8, 9 and 10 are primarily responsible for interactions between CFH and PspCN. Although PspCN—commensurate with its small size (12 kDa)—may bind directly to just a few central CCPs (of ~7 kDa each), its remarkably light complex with CFH may be favoured by a cooperative spatial rearrangement of other CCPs, stabilized by new intramolecular intermodular interactions. To test this hypothesis we compared chemical cross-linking data within CFH before and after PspCN addition.

Analysis of CFH Architecture by Cross-Linking and Mass Spectrometry

In the absence of cross-linker, a solitary band was detected following SDS-PAGE of a plasma-purified CFH sample, as expected. After a 60-minute incubation of the same CFH sample (0.58 µg/µL) with 3.9 BS3, two SDS-PAGE bands appeared that were both candidates for monomeric CFH (FIG. 5A). The more slowly migrating bend contained more head-to-tail (e.g. CCP 20-to-CCP 4 and CCP 19-to-CCP 5) cross-links (FIG. 5B), reflecting capture of a bent-back conformation of CFH. The relative abundance of such a conformation in the original sample is unknown since it would accumulate over time even if it were relatively rare.

Upon addition of PspCN at a 1. 15:1 molar ratio to 0.56 µg/µL CFH, followed by incubation with 3.9 mM BS3, these two bands collapsed into one (FIG. 5B). This band contained both PspCN and CFH, as discussed above. Analysis revealed that cross-linking captured a different compact conformation of CFH compared to the one captured in the absence of PspCN. Importantly, following addition of PspCN, CCP 20-to-CCP 7 and CCP 18-to-CCP 5 cross-links were gained while CCP 20-to-CCP 4 and CCP 19-to-CCP 5 cross-links were no longer detected (FIG. 5B). In addition, a prominent new band appeared after incubation of CFH with PspCN and cross-linker, which migrated consistently with the MW of dimeric CFH. Cross-links unique to this presumed PspCN-induced CFH dimer included CCP 5-to-CCP 7 and CCP 18-to-CCP 20.

We surmised from these studies that binding of PspCN to central CFH facilitates adoption of a new stable conformation of CFH, helping to explain the negligible dissociation rate of the bimolecular complex. The PspCN-stabilized conformation of CFH may have nascent exposed self-association sites that would explain increased dimer capture by cross-linker. But analysis (in the absence of cross-linker) by size-exclusion chromatography-multiple angle light scattering (SEC-MALS) showed a predominantly 1:1 complex of plasma-purified CFH:PspCN and did not detect any CFH dimer before (loaded at 710 ug/ml) or after (loaded at 520 ug/ml) PspCN addition. Unexpectedly, a small quantity of dimeric PspCN had formed in the sample submitted for SEC-MALS before mixing with CFH, and there was a corresponding appearance of FH:PspCN$_2$ complex. But these species were present in small amounts and are almost certainly artefacts. More importantly, we hypothesized that there are newly exposed ligand-binding sites in the PspCN-stabilized conformation of CFH and we set out to test this hypothesis through functional assays.

New Binding Site for TED/C3d Exposed by PspCN Binding to CFH

Commercially sources plasma-purified human C3b, C3c and C3d were immobilized using standard amine coupling to different channels of the same C1 SPR chip (Biacore). Subsequently, having demonstrated that PspCN does not bind to C3b, C3c or C3d (data not shown), the affinities of CFH, or the CFH:PspCN complex, for C3b along with its various degradation products were measured in the same experiment (FIG. 6). A remarkably consistent affinity for immobilized C3b was obtained for recombinant and plasma-purified CFH that matches well with literature $K_D$ values of 0.5-0.6 mM (Table 1). Interestingly, the CFH:PspCN complex bound consistently three-fold better to C3b, with a $K_D$=0.15-0.2 mM. Virtually identical results were obtained for PspCNR1 (data not shown).

We found that CFH (alone) did not bind well to C3c or C3d on the SPR chip (FIGS. 6A-6B). This agrees well with other recent reports[22, 23, 38]. On the other hand, it has been established that the recombinant fragment CFH 19-20 binds equally well (and using the same amino acid residues) to both C3d and C3b with a $K_D$ of ~2 μM[15, 39]. Clearly, the C3b/C3d-binding site located in CCPs 19-20 is not fully accessible within intact CFH in this SPR-based assay. It is striking, therefore, that CFH:PspCN bound some two orders-of-magnitude better to C3d than did CFH alone (FIGS. 6A-6B, Table 2). The $K_D$ (2 μM) for this interaction was comparable with that of FH 19-20 binding to C3d or C3b. This result is consistent with our hypothesis that PspCN binding brings about a conformational rearrangement of CFH that exposes new ligand-binding sites.

Functional Assays of CFH:PspCN

Figure 7:
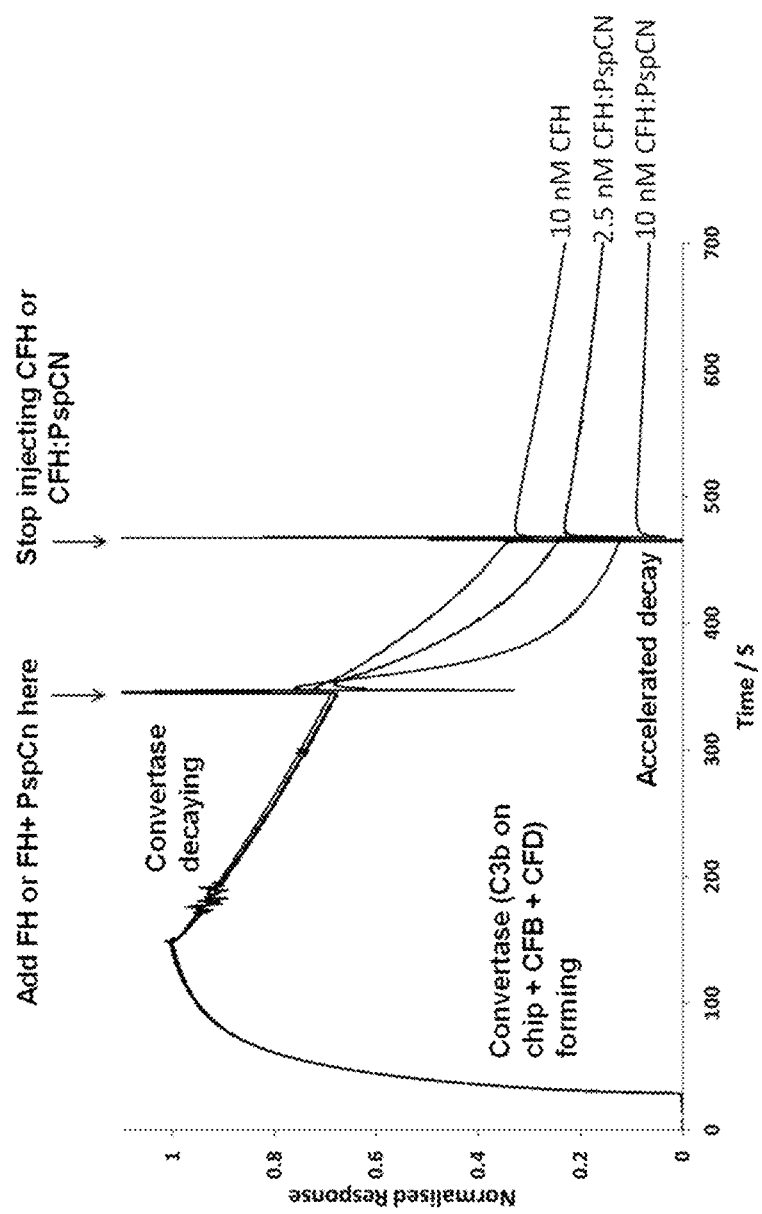
FIG. 7: PspCN boosts the decay acceleration activity of CFH. 2.5 nM CFH:PspCN is a better decay accelerator than 10 nM CFH, of C3b.Bb, formed by flowing C3, CFB and CFD over a CM5 chip loaded with a small quantity of C3b (see text).

Given that PspCN has evolved the capability to bind very tightly to CFH and modify its conformation, the question arises, what effect does PspCN binding have on the functional properties of CFH as an inhibitor of C3b amplification. We tested its effect on decay-accelerating activity by assembling the convertase on an SPR chip and watching it dissociate into its components before and after added CFH (or CFH:PspCN) (FIG. 7). It is evident that 10 nM CFH has a clear accelerating influence on decay (as expected) but this is exceeded about two-fold by a mixture of 2.5 nM CFH and 2.5 nM PspCN.

PspCN Reveals Cryptic Effects of Disease-Linked Mutation in CFH

Figure 8A:
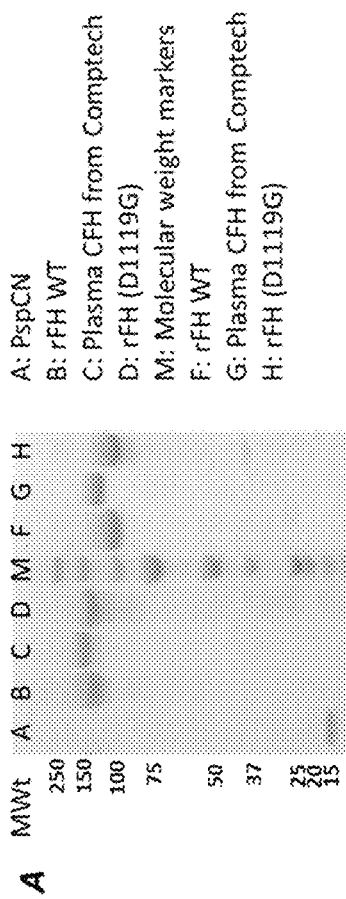
FIGS. 8A-8B: Properties of CFH (DH119G).

We produced in *P. pastoris* the mutant CFH (D1119G) (FIG. 8A). This aHUS-linked mutation within CCP 19 has not previously been fully characterized in the context of purified full-length CFH. On the other hand in the context of the C-terminal fragment, CFH 19-20, D1119G was reported to cause near-total loss of C3d and C3b binding[39]. Moreover, within the CFH 19-20:C3d complex D1119 occupies a key position in the intermolecular interface[39]. Interestingly, we found that CFH (D1119G) binds to C3b on the SPR chip surface with approximately the same affinity as CFH (wt) (Table 2). As expected, CFH (D1119G) did not have significant affinity for iC3b or C3d.

We made the PspCN:CFH (D1119G) complex and tested its binding to C3b and C3d. The complex showed some improvement, compared to CFH (D1119G) alone, in C3b binding (Table 2) but—unlike the CFH (wt):PspCN complex—it showed no enhancement of C3d binding. Thus PspCN binding has revealed a striking difference between CFH (wt) and CFH (D1119G) that was not evident from a C3b/C3d-binding study performed in the absence of PspCN on an SPR chip. This reaffirms our hypothesis that PspCN can disinter the partially or completely buried C-terminal C3d/C3b-binding site of CFH.

Figure 8B:
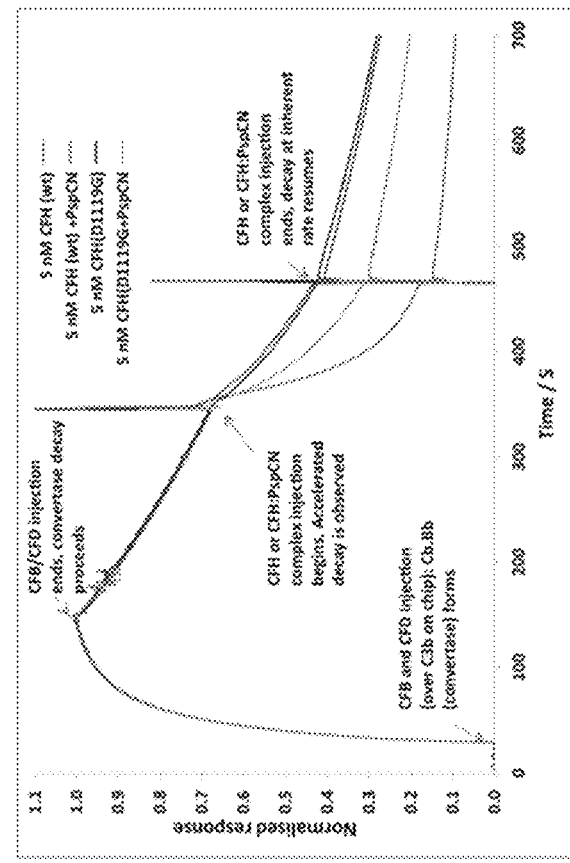

We next asked whether the latent deficit in the ability of CFH (D1119G) to bind to the TED domain of C3b, which can be unmasked by PspCN, has consequences for the ability of this mutant to accelerate the decay of C3b.Bb. We found that CFH (D1119G), by itself, accelerates the disassociation of C3b.Bb about as well as does CFH (wt) (FIG. 8B). This result is consistent with the retention, in the mutated CFH, of near-wild-type C3b-binding affinity (on an SPR chip). The CFH mutant, however, behaved strikingly differently from CFH (wt) when in complex with PspCN; only a small improvement in the rate of decay acceleration was recorded, as opposed to the approximately tenfold improvement observed in the case of wild-type CFH upon binding PspCN.

Next we investigated the extent to which the D1119G mutation perturbs CFH from acting on a surrogate host-cell surface. Plasma-purified human CFH, when added to CFH-deficient human serum, protects sheep erythrocytes (FIG. 8C) (that, like human erythrocytes, have sialic acid-rich surfaces) but not rabbit erythrocytes (with sialic acid-poor surfaces) (FIG. 7D) from complement-mediated haemolysis; this is consistent with what has been shown previously [40]. On the other hand, CFH (D1119G) (alone) was unable to protect either rabbit or sheep erythrocytes, consistent with a causal role in atypical haemolytic uraemic syndrome. This shows that despite CPH (D1119G) binding like CFH (wt) to C3b on a SPR sensor chip surface, this disease-linked mutant does not work as well as CFH (wt) on a self surface. Addition of PspCN improved slightly the ability of CFH (D1119G) to protect sheep erythrocytes (FIG. 8C) consistent with the above-noted small improvement in C3b binding of PspCN:CFH (D1119G) compared to CFH (D1119G). The CFH:PspCN complex shows only a modest increase in the protection of (sialic-acid poor) rabbit erythrocytes (FIG. 8D) when compared to plasma-purified CFH alone. Thus, despite the PspCN-induced availability of the C-terminal C3d/TED-binding site in the CFH, control of C3b amplification on the rabbit erythrocyte remains inadequate. Clearly, adoption by CFH of an activated conformation in the PspCN CFH complex is not sufficient—anchoring to the cell surface via the cholesterol-binding domain of intact PspC, or—on a host surface-binding of CFH to sialic acids (for example) is also a requirement.

Figure 8C:
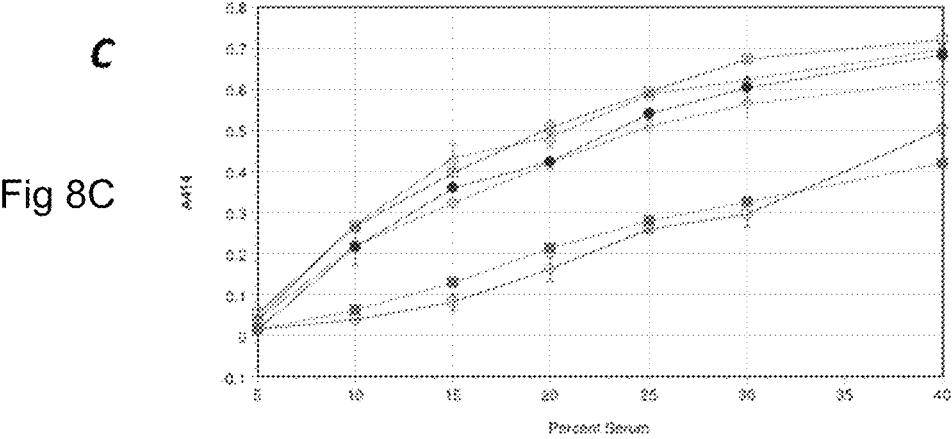
(FIG. 8C) Neither CFH nor rCFH (D1119G) (nor a mixture of the two) protects (non sialic-acid bearing) rabbit erythrocytes; PspCN induces some protective capacity for CFH and the 1:1 CFH:rCFH (D1119G) mixture.
Figure 8D:
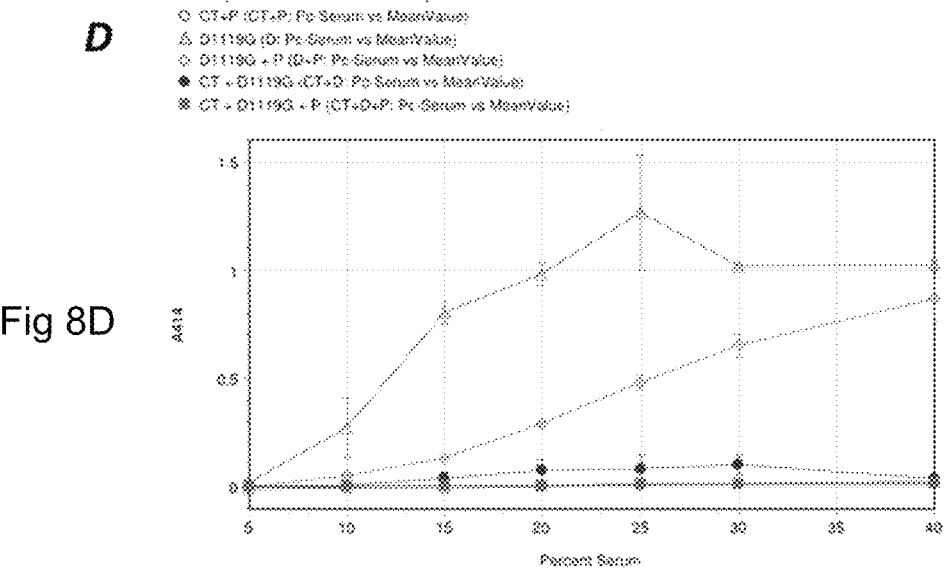
(FIG. 8D) rCFH (D1119G) is poor at protecting sheep erythrocytes (that are sialylated and therefore surrogates for human erythrocytes) from haemolysis (indicated by absorbance reading proportional to released haemoglobin on y-ordinate) by diluted human plasma (x-ordinate) compared to CFH. Addition of PspCN improves protective power of CFH (D1119G). A mixture of 1 µM:1 µM CFH and rCFH (D1119G) does not provide full protection unless PspCN is added.

Finally we attempted to partially recreate the scenario of a heterozygous individual with the CFH (D1119G) mutation by performing the same haemolysis assays using a mixture of 1 µM CFH (wt) and 1 µM CFH (D1119G) (FIGS. 8C and D). In this 1:1 case, similar high levels of haemolysis were, unsurprisingly, obtained for rabbit erythrocytes as were observed for 2 µM CFH (wt); in the presence of PspCN, similar modest decreases in rabbit erythrocyte haemolysis were observed for both the 1:1 mixture and CFH (wt). Interestingly, however, the 1:1 "heterozygous" mixture was unable to completely protect sheep erythrocytes from complement-mediated lysis until PspCN was also included in the reaction. The PspCN therefore, was able to activate CFH in the 1:1 mixture (equating to a heterozygous individual) sufficiently for lysis to be inhibited.

Discussion

CFH is key to the control of C3b amplification that is the pivotal event in the operation of the complement system. It is essential that CFH distinguishes between C3b on host cells and on foreign ones. This is unlikely to be solely a matter of selective enrichment of CFH at those surfaces requiring protection; that would allow CFH to be very easily hijacked by microbes, rendering the complement system virtually useless as a first line of defence against infection. Thus CFH may have evolved to "hide" some of its complement-regulatory sites and reveal them only in the presence of certain molecular markers. We speculated that such a hypothetical strategy could explain why CFH has so many CCP modules that do not appear to bind directly to ligands. They could allow CFH to adopt different conformations—exposing different ligand-binding sites—in response to surface-specific molecular signatures. Our results presented here, based on an investigation of the complex formed between PspCN and CFH, strongly back such a model.

We showed, using SPR, that the N-terminal 104-amino acid residues of PspC from *S. pneumoniae* (D39) (residues 37-140 of the pre-processed protein) are sufficient to bind irreversibly, on the biological timescale, to recombinant human CFH as well as human CFH purified from blood. This observation is in agreement with the previously reported binding of plasma-purified CFH (Lu L, Ma Y, Zhang J R. *Streptococcus pneumoniae* recruits complement factor H through the amino terminus of CbpA. J Biol Chem. 2006 June 2; 281 (22):15484-74), to a similar-length N-terminal construct of PspCN, which was assessed in solution using isothermal titration calorimetry and found to be too tight to measure (<1 nM). Our complex of PspCN:CFH is significantly more stable than the complex observed in a previously conducted SPR-based experiment using a slightly extended PspC construct (residues 39-152) (Hammerschmidt S, Agarwal V, Kunert A, Haelbich S, Skerka C, Zipfel P F. The host immune regulator factor H interacts via two contact sites with the PspC protein of *Streptococcus pneumoniae* and mediates adhesion to host epithelial cells. J Immunol. 2007 May 1; 178(9):5848-58). On the other hand, we did not observe any loss or gain of affinity for a significantly longer construct (residues 39-259) and it is likely that PspCN encompasses the entirety of the CFH-binding site within full-length PspC.

Plasma-derived CFH has eight out of nine potential N-glycosylation sites, mainly in central CCPs, occupied by bi-sialylated bi-antennary glycans (Fenaille F, Le Mignon M, Groseil C, Ramon C, Riandé S, Siret L, Bihoreau N. Site-specific N-glycan characterization of human complement factor H. Glycobiology, 2007 September; 17(9):932-44). The recombinant CFH used in this study (both wild-type and D1119G) had been enzymatically deglycosylated. That all these versions of CFH have comparable affinities for PspCN shows that the N-glycans of plasma CFH do not play a significant role in PspCN binding. They also appeared to be non-essential for binding to C3b or for participation in a range of assays carried out in vitro (Jouvin M H, Kazatchkine M D, Cahour A, Bernard N. Lysine residues, but not carbohydrates, are required for the regulatory function of H on the amplification C3 convertase of complement. J Immunol. 1984 December; 133(8):3250-4).

Assuming that PspC on the bacterial surface has a similar affinity as PspCN for CFH, then the bacterium will acquire and retain—presumably for the duration of its time spent in the bloodstream—a CFH molecule attached to each of its surface-displayed PspC molecules. It has been suggested (Agarwal V, Asmat T M, Luo S, Jensch I, Zipfel P F, Hammerschmidt S. Complement regulator Factor H mediates a two-step uptake of *Streptococcus pneumoniae* by human cells. J Biol Chem. 2010 July 23; 285(30):23486-95; Quin L R, Onwubiko C, Moore Q C, Mills M F, McDaniel L S, Carmicle S. Factor H binding to PspC of *Streptococcus pneumoniae* increases adherence to human cell lines in vitro and enhances invasion of mouse lungs in vivo. Infect Immun. 2007 August; 75(8):4082-7) that *S. pneumoniae* utilizes this molecule not only for avoiding C3b-amplification but also, preparatory to invasion, for localization at the surfaces of host cells bearing ligands for CFH. It was therefore intriguing to learn more about the structural and functional properties of this remarkably tight complex.

Based on three orthogonal approaches—binding affinities of truncation mutants, NMR chemical-shift perturbations and chemical cross-linking—we found that PspCN binds very tightly towards the middle region of CFH at a site within CCPs 8-10. We obtained no evidence for significant direct participation of other CCPs. Nonetheless full-length CFH binds to PspCN far more tightly than FH 8-15 so it is clear that other CCPs play a role, albeit an indirect one, in complex formation as discussed further below. Our results concur with a flow-cytometry study (Dave S, et al. 2004) that implied some or all of CCPs 8-10 were crucial for binding of CFH, to *Pneumococcal* isolates of 14 different strains, via the N-terminal 225 amino acids of PspCN. Our results are also largely in agreement with Hammerschmidt et al (Hammerschmidt S, et al. 2007) who used a 250-residue segment of PspC from strain ATCC 33400 (serotype 1) that they called SH2. They showed by dot blot and by SPR (although no $K_D$ values were reported) that CCPs 8-11 binds to SH2 while FH 1-7, FH 11-15 and FH 16-20 showed no or very little binding to SH2. These authors demonstrated that heparin (that interacts with CCPs 7 and 20 of CFH, but also binds PspCN according to our observations) inhibits the SH2-CFH interaction, while a monoclonal antibody to CCPs 19-20 inhibits binding of SH2 to FH 8-20. This suggested to the authors a second direct PspCN-binding site must be located on the C-terminal modules. Our studies (although they do demonstrate a very weak FH 19-20:PspCN interaction) suggest these inhibitors are more likely to work indirectly by blocking an intramolecular component of the binary complex, as discussed further below. Another study (Duthy T G, et al. 2002) also reported binding (by ELISA) of FH 8-15 as well as FH 8-13, but not FH 1-7, FH 10-12 or FH 16-20, to PspC, which concurs with our data. They were, however, unable to detect binding for FH 8-12, and only weak binding to FH 8-14, and they thus assigned the binding site to FH 13-15. All their constructs were produced as recombinant truncation mutants in *P. pastoris*, like the ones in the current study, but yields were very low, so authentication would have been difficult. In sum, there are now multiple lines of evidence supporting direct engagement by PspC of modules 8-10 in CFH that are free of binding sites for C3b, GAGs or other known ligands. This would be consistent with the notion that it benefits the bacterium to leave these sites available.

The negligible off-rate and hence remarkably high affinity of the CFH:PspCN complex may derive from the adoption of stable, mutually dependent, new conformations by both protein partners upon complex formation. Thus, although its MW is just 11 kD, and hence if could only contact a few CCPs simultaneously. PspCN binds extremely tightly to CFH (155 kD) and this domain becomes a folded protein in the process (we have not investigated whether this domain is folded when if is part of the intact PspC protein).

Full-length CFH binds to PspCN approximately four orders-of-magnitude more tightly than does CFH 8-9, and three orders-of-magnitude more tightly than does CFH 8-15. This is despite the lack of evidence from our studies that CCPs other than 8, 9 and 10 participate directly in PspCN binding. Cross-linking tells us that PspCN binding causes major changes in the structure of the bigger protein. Due to its extended and flexible architecture, and the consequent potential for interactions between non-neighbouring CCP modules, free CFH has multiple conformational possibilities; our result suggest that some of these are more stable than others but are separated from one another by relatively high activation energy barriers. PspcN binding could induce the formation of a stable conformer not kinetically accessible to CFH in the absence of PspCN. The existence of such a conformation is suggestive that self-surface specific molecular markers (such as GAGs and sialic acid) might also act to facilitate transitions between CFH conformers through a similar strategy. The interesting observation that other bacterial proteins (unlike PspC) bind directly to the same regions of CFH (CCPs 7 and 20) (Ferreira V P, Pangburn M K, Cortés C. Complement control protein factor H: the good, the bad, and the inadequate. Mol Immunol. 2010 August; 47(13):2187-97) as do host-surface molecular markers (Schmidt C Q, Herbert A P, Kavanagh D, Gaudy C, Fenton C J, Blaum B S, Lyon M, Uhrin D, Barlow F N. A new map of glycosaminoglycan and C3b binding sites on factor H. J Immunol. 2008 August 15; 181(4):2610-9) indicates that they too might act in this way.

The results discussed so far relate to cross-links observed in a 1:1 PspCN:CFH complex. This is the dominant species in a mixture of CFH and PspCN according to analysis by SEC-MALS (loaded onto the size-exclusion column at 500 mg mL$^{-1}$ or ~3 mM). Yet the cross-linking data indicated that PspCN increased the tendency of CFH to form dimers in which CCPs 5 and 7 (presumably from different monomers) are brought close together and there is also a dimer-specific cross-link between CCPs 18 and 20. While two molecules of CFH could interact directly with the same PspCN molecule, this seems unlikely given the small size of PspCN, and its large interaction surface with CCPs 8-9 in what appeared to be the 1:1 complex observed in the NMR samples. On the other hand it is feasible that the altered CFH conformation stabilized by PspCN results in exposure of previously buried regions of CFH that participate in a weak self-association that can be captured by cross-linking: based on the observed dimer-specific cross-links these are likely to involve CCPs 5-7 and possibly CCPs 18-20. This effect may be a product of encounters (captured by cross-linking) between two soluble PspCN:CFH complexes. This result parallels a previous report that soluble GAG-surrogates, such as heparin, induced oligomerisation of soluble CFH that could not be explained by multiple CFH molecules binding to the same GAG, and that might also have arisen from soluble CFH:GAG complexes self-associating via nascent exposed sites. It is not known whether CFH/PspC dimers form on the bacterial surface.

In this study we used SPR to measure the affinity of FH and FH:PspCN for C3b chemically immobilized on a carboxymethylated surface of a sensorchip. This experimental setup is probably a very poor model of a self-surface, and hence the affinities observed in the case of SPR may be similar to those that would be observed on a "random" complement-activating surface (such as a microbe). In the current study, both recombinant and plasma-purified CFH interacted with C3b, immobilized on the surface of a SPR sensorchip, with a $K_D$ (0.6 mM) that is in line with other reported values. This is 15-times tighter and four-times tighter, respectively, compared to either FH 1-4 ($K_D$=~10 mM) or FH 19-20 ($K_D$=2-3 mM) (Schmidt C G, Herbert A P, Kavanagh D, Gandy C, Fenton C J, Blaum B S, Lyon M, Uhrin D, Barlow P N. A new map of glycosaminoglycan and C3b binding sites on factor H. J Immunol. 2008 August 15; 181(4):2610-9). We also were in agreement with authors of previous studies[38 and 22] in our observation that full-length CFH binds poorly to C3d immobilized on the SPR sensorchip when compared to either CFH or CFH 19-20 binding to C3b, or CFH 19-20 binding to C3d. It is noteworthy that in previous studies, C3b was deposited on the chip in various ways, including via its thioester, and similar results were obtained[39]. Thus the C3b/TED-binding site at the C-terminus of intact CFH is not fully available when CFH is presented with C3d on the SPR chip surface.

This begs the important question as to whether the C-terminal C3b/d-binding site of CFH, which is unavailable to bind C3d, is nonetheless deployed following an encounter between CFH and C3b. Interestingly, in the current study, CFH (D1119G) binds to C3b on the SPR sensorchip almost as well as does CFH (wt), despite the fact that the fragment CFH 19-20 (D1119G) has virtually no affinity for C3b or C3d[39]. This suggests that in SPR-based assays of CFH binding to C3b (as well as those measuring binding to C3d), the C-terminal site effectively makes no contribution. On the other hand, CFH (D1119G) (like CFH (wt)) binds fifteen-fold more tightly than does CFH 1-4. It may be that additional CCPs (i.e. between CCPs 5 and 18) contribute to the intermolecular interaction and indeed it was shown previously that recombinant CFH 6-8 binds very weakly to C3b[15] and Jokiranta T S, Hellwage J, Koistinen V, Zipfel P F, Meri S. Each of the three binding sites on complement factor H interacts with a distinct site on C3b. J Biol Chem. 2000 September 8; 275(36):27657-62). Alternatively, the CFH:C3b complex could be favoured by intramolecular interactions that are absent in free CFH (by analogy with the CFH:PspCN complex). In either case, we may conclude that the C-terminal C3b/C3d binding site in full-length CFH is, by default, masked or occluded.

In contrast it is clear that the C3b/C3d binding site is available in the CFH:PspCN complex, since this is the only coherent explanation for its >50-fold better C3d binding, compared to intact CFH, which equates with the C3d-binding affinity of FH 19-20. Moreover, two-site binding of CFH:PspCN to C3b also helps to explain its relatively high affinity for C3b (60-fold higher than for FH 1-4 alone and 18-fold higher than FH 19-20 alone). Although the difference in affinities (for C3b) between CFH and CFH:PspCN is "only" four fold, this could be highly significant for the bacterium. Were CFH captured in its "latent" conformation, a $K_D$ of 0.6 µM (for the C3b:CFH complex) might be inadequate for control of C3b amplification that is a binary on-off process able to overwhelm regulators once a C3b population threshold is breached; on the other hand a $K_D$ of 0.15 µM for the CFH:PspCN-C3b complex may be sufficient to maintain the numbers of tethered C3b molecules on the surface below the threshold for run-away activation. Such a notion, together with the ten-fold improvement in decay-acceleration activity, is consistent with the significantly improved haemolysis-prevention properties of PspCN-bound CFH observed in the present study. The ability of PspCN to restore haemolysis protection in CFH-depleted serum supplemented with a 1:1 mixture of CFH (wild-type) and CFH (D1119G) is suggestive of its therapeutic potential.

These observations suggest strongly that other bacterial proteins induce the same or a similar activated conformation of CFH to that induced by binding of PspCN. The great majority of bacterial proteins bind elsewhere to CFH but they could nonetheless stabilize a similar conformation. Cross-linking shows that CCPs 7 and 20 are close together in the PspCN complex and many bacterial proteins engage both these sites, potentially bringing them together. It will therefore be important to explore the structures of other bacterial protein:CFH complexes using similar methods to those we have deployed in the current study. A tantalizing further possibility is that molecular markers on self-surfaces stabilize the same activated conformation of CFH. It is noteworthy that polyanionic markers (modelled experimentally by heparin) bind to CCPs 7 and 20[15] while more recently, oxidation-specific epitopes (thought to be important for recruiting CFH to damaged cells) also interact with these two CCPs.[34] This possibility highlights the importance of using biomimetic surfaces for assessing the functional repercussions of disease-linked SNPs and mutations in CFH because otherwise some will be missed—as exemplified herein with our C3b-binding study of CFH (D1119G).

In conclusion, there is now strong evidence to suggest that CFH circulates in a latent form wherein some of its C3b-binding capability is locked away, preventing if being a highly effective regulator of C3b amplification and therefore spontaneously shutting down complement activation altogether. Factor H can also exist in an "active" form in which its C3b-binding sites are available and juxtaposed in such a way as to bind bivalently and therefore avidly to its C3b (or C3b.Bb) target. The bacterial protein PspC can induce this active conformation and it is feasible that other bacterial proteins use the same trick (although via a different form of engagement with CFH). That such a conformation exists, and is exploited by bacteria, is highly suggestive of it also being the active conformation on self surfaces. Further studies are now needed to test whether this is indeed the molecular basis for self versus non-self discrimination by the key soluble regulator of the vertebrate complement system.

REFERENCES FOR EXAMPLE 1

1. Ricklin, D., and Lambris, J. D. (2013) Complement in immune and inflammatory disorders: pathophysiological mechanisms, *Journal of immunology* 190, 3831-3838.
2. Ricklin, D., and Lambris, J. D. (2013) Complement in immune and inflammatory disorders: therapeutic interventions, *Journal of immunology* 190, 3839-3847.
3. Lachmann, P. J. (2009) The amplification loop of the complement pathways, *Adv Immunol* 104, 115-149.
4. Gadjeva, M., Dodds, A. W., Taniguchi-Sidle, A., Willis, A. C., Isenman, D. E., and Law, S. K. (1998) The covalent binding reaction of complement component C3, *Journal of immunology* 161, 985-990.
5. Schmidt, C. Q., Herbert, A. P., Hocking, H. G., Uhrin, D., and Barlow, P. N. (2008) Translational Mini-Review Series on Complement Factor H: Structural and functional correlations for factor H, *Clin Exp Immunol.* 151, 14-24.
6. Ferreira, V. P., Pangburn, M. K., and Cortes, C. (2010) Complement control protein factor H: the good, the bad, and the inadequate, *Mol Immunol* 47, 2187-2197.
7. Perkins, S. J., Nan, R., Li, K., Khan, S., and Miller, A. (2011) Complement Factor H-ligand interactions: Self-association, multivalency and dissociation constants, *Immunobiology*.
8. Makou, E., Herbert, A. P., and Barlow, P. N. (2013) Functional Anatomy of Complement Factor H, *Biochemistry*.
9. Ripoche, J., Day, A. J., Harris, T. J., and Sim, R. B. (1988) The complete amino acid sequence of human complement factor H, *Biochem J.* 249, 593-602.
10. Soares, D. C., and Barlow, P. N. (2005) Complement Control Protein Modules in the Regulators of Complement Activation, In *Structural Biology of the Complement System* (Morikis, D., and Lambris, J. D., Eds.), pp 19-62, CRC Press, Taylor & Francis Group, Boca Raton.
11. Matsumoto, A. K., Kopicky-Burd, J., Carter, R. H., Tuveson, D. A., Tedder, T. F., and Fearon, D. T. (1991) intersection of the complement and immune systems: a signal transduction complex of the B lymphocyte-containing complement receptor type 2 and CD19, *The Journal of experimental medicine* 173, 55-64.
12. de Cordoba, S. R., and de Jorge, E. G. (2008) Translational mini-review series on complement factor H: genetics and disease associations of human complement factor H, *Clin Exp Immunol.* 151, 1-13.
13. Hageman, G. S., Anderson, D. H., Johnson, L. V., Hancox, L. S., Taiber, A. J., Hardisty, L. I., Hageman, J. L., Stockman, H. A., Borchardt, J. D., Gehrs, K. M., Smith, R. J., Silvestri, G., Russell, S. R., Klaver, C. C., Barbazetto, I., Chang, S., Yannuzzi, L. A., Barlie, G. R., Merriam, J. C., Smith, R, T., Olsh, A. K., Bergeron, J., Zernant, J., Merriam, J. E., Gold, B., Dean, M., and Allikmets, R. (2005) A common haplotype in the complement regulatory gene factor H (HF1/CFH) predisposes individuals to age-related macular degeneration, *Proceedings of the National Academy of Sciences of the United States of America* 102, 7227-7232. Epub 2005 May 7223.
14. Blackmore, T. K., Sadion, T. A., Ward, H. M., Lublin, D. M., and Gordon, D. L. (1996) Identification of a heparin binding domain in the seventh short consensus repeat of complement factor H, *Journal of immunology* 157, 5422-5427.
15. Schmidt, C. Q., Herbert, A. P., Kavanagh, D., Gandy, C., Fenton, C. J., Blaum, B. S., Lyon, M., Uhrin, D., and Barlow, P. N. (2008) A new map of glycosaminoglycan and C3b binding sites on factor H, *Journal of immunology* 181, 2610-2619.
16. Clark, S. J., Bishop, P. N., and Day, A. J. (2010) Complement factor H and age-related macular degeneration: the role of glycosaminoglycan recognition in disease pathology, *Biochem Soc Trans* 38, 1342-1348.
17. Clark, S. J., Ridge, L. A., Herbert, A. P., Hakobyan, S., Mulloy, B., Lennon, R., Wurzner, R., Morgan, B. P., Uhrin, D., Bishop, P. N., and Day, A. J. (2013) Tissue-specific host recognition by complement factor h is mediated by differential activities of its glycosaminoglycan-binding regions, *Journal of immunology* 190, 2049-2057.
18. Richards, A., Buddles, M. R., Donne, R. L., Kaplan, B. S., Kirk, E., Venning, M. C., Tielemans, C. L., Goodship, J. A., and Goodship, T. H., (2001) Factor H mutations in hemolytic uremic syndrome cluster in axons 18-20, a domain important for host cell recognition, *Am J Hum Genel* 68, 485-490.
19. Gordon, D. L., Kaufman, R. M., Blackmore, T. K., Kwong, J., and Lublin, D. M. (1995) identification of complement regulatory domains in human factor H, *J Immunol.* 155, 348-356.
20. Appel, G. B., Cook, H. T., Hageman, G., Jennette, J. C., Kashgarian, M., Kirschfink, M., Lambris, J. D., Lanning, L., Lutz, H. U., Meri, S., Rose, N. R., Salant, D. J., Sethi, S., Smith, R. J., Smoyer, W., Tully, H. F., Tully, S. P., Walker, P., Welsh, M. Wurzner, R., and Zipfel, P. F. (2005) Membranoproliferative glomerulonephritis type II (dense deposit disease): an update, *J Am Soc Nephrol* 16, 1392-1403.
21. Fridkis-Hareli, M., Storek, M., Mazsaroff, I., Risitano, A. M., Lundberg, A. S., Horvath, C. J., and Holers, V. M. (2011) Design and development of TT30, a novel C3d-targeted C3/C5 convertase inhibitor for treatment of human complement alternative pathway-mediated diseases, *Blood* 118, 4705-4713.
22. Schmidt, C. Q., Bai, H., Lin, Z., Risitano, A. M., Barlow, P. N., Ricklin, D., and Lambris, J. D. (2013) Rational Engineering of a Minimized Immune Inhibitor with Unique Triple-Targeting Properties, *Journal of immunology June* 1; 190(11):5712-21.
23. Hebecker, M., Alba-Dominguez, M., Roumenina, L. T., Reuter, S., Hyvarinen, S., Dragon-Durey, M. A., Jokiranta, T. S., Sanchez-Corral, P., and Jozsi, M. (2013) An Engineered Construct Combining Complement Regulatory and Surface-Recognition Domains Represents a Minimal-Size Functional Factor H, *Journal of immunology*.
24. Blom, A. M., Hallstrom, T., and Riesbeck, K. (2009) Complement evasion strategies of pathogens-acquisition of inhibitors and beyond, *Mol Immunol* 46, 2808-2817.
25. Zipfel, P. F., Skerka, C. Hellwage, J., Jokiranta, S. T., Meri, S., Brade, V., Kraiczy, P., Noris, M., and Remuzzi, G. (2002) Factor H family proteins: on complement, microbes and human diseases, *Biochem Soc Trans* 30, 971-978.
26. Janulczyk, R., Iannelli, F., Sjoholm, A. G., Pozzi, G., and Bjorck, L. (2000) Hic, a novel surface protein of *Streptococcus pneumoniae* that interferes with complement function, *The Journal of biological chemistry* 275, 37257-37263.
27. Dave, S., Brooks-Walter, A., Pangburn, M. K., and McDaniel, L. S. (2001) PspC, a pneumococcal surface protein, binds human factor H, *Infection and immunity* 69, 3435-3437.
28. Jarva, H., Janulczyk, R., Hellwage, J., Zipfel, P. F., Bjorck, L., and Meri, S. (2002) *Streptococcus pneumoniae* evades complement attack and opsonophagocytosis by expressing the pspC locus-encoded Hic protein that binds to short consensus repeats 8-11 of factor H, *Journal of immunology* 168, 1885-1894.
29. Hyams, C., Trzcinski, K., Camberlein, E., Weinberger, D. M., Chimalapati, S., Noursadeghi, M., Lipsitch, M., and Brown, J. S. (2012) *Streptococcus pneumoniae* capsular serotype invasiveness correlates with the degree of factor H binding and opsonisation with C3b/iC3b, *Infection and immunity*.
30. Bexborn, F., Andersson, P. O., Chen, H., Nilsson, B., and Ekdahl, K. H. (2008) The tick-over theory revisited: formation and regulation of the soluble alternative complement C3 convertase (C3(H2O)Bb), *Mol Immunol* 45, 2370-2379.
31. Kirkitadze, M. D., and Barlow, P. N. (2001) Structure and flexibility of the multiple domain proteins that regulate complement activation, *Immunol Rev* 180, 146-161.
32. Trouw, L. A., Bengtsson, A. A., Gelderman, K. A., Dahlback, B., Sturfelt, G., and Blom, A. M. (2007) C4b-binding protein and factor H compensate for the loss of membrane-bound complement inhibitors to protect apoptotic cells against excessive complement attack, *The Journal of biological chemistry* 282, 28540-28548.
33. Leffler, J., Herbert, A. P., Norstrom, E., Schmidt, C. Q., Barlow, P. N., Blom, A. M., and Martin, M. (2010) Annexin-II, DNA, and histones serve as factor H ligands on the surface of apoptotic cells, *The Journal of biological chemistry* 285, 3766-3776.
34. Weismann, D., Hartvigsen, K., Lauer, N., Bennett, K. L., Scholl, H. P., Charbel Issa, P., Cano, M., Brandstatter, H., Tsimikas, S., Skerka, C., Superti-Furga, G., Handa, J. T., Zipfel, P. F., Witztum, J. L., and Binder, C. J. (2011) Complement factor H binds malondialdehyde epitopes and protects from oxidative stress, *Nature* 478, 76-81.
35. Schmidt, C. Q., Slingsby, F. C., Richards, A., and Barlow, P. N. (2011) Production of biologically active complement factor H in therapeutically useful quantities, *Protein Expr Purif* 76, 254-263.
36. Pangburn, M. K. (2002) Cutting edge: localization of the host recognition functions of complement factor H at the carboxyl-terminal: implications for hemolytic uremic syndrome, *Journal of immunology* 169, 4702-4706.
37. Blaum, B. S., Deakin, J. A., Johansson, C. M., Herbert, A. P., Barlow, P. N., Lyon, M., and Uhrin, D. (2010) Lysine and arginine side chains in glycosaminoglycan-protein complexes investigated by NMR, cross-linking, and mass spectrometry: a case study of the factor H-heparin interaction, *Journal of the American Chemical Society* 132, 6374-6381.
38. Goicoechea de Jorge, E., Caesar, J. J., Malik, T. H., Patel, M., Colledge, M., Johnson, S., Hakobyan, S., Morgan, B. P., Harris, C. L., Pickering, M. C., and Lea, S. M. (2013) Dimerization of complement factor H-related proteins modulates complement activation in vivo, *Proceedings of the National Academy of Sciences of the United States of America* 110, 4685-4690.
39. Morgan, H. P., Schmidt, C. Q., Guariento, M., Blaum, B. S., Gillespie, D., Herbert, A. P., Kavanagh, D., Mertens, H. D., Svergun, D. I., Johansson, C. M., Uhrin, D., Barlow, P. N., and Hannan, J. P. (2011) Structural basis for engagement by complement factor H of C3b on a self surface, *Nat Struct Mol Biol* 18, 463-470.
40. Kazatchkine, M. D., Fearon, D. T., and Austen, K. F. (1979) Human alternative complement pathway: membrane-associated sialic acid regulates the competition between B and beta 1 H for cell-bound C3b, *Journal of immunology* 122, 75-81.

Example 2—Further Investigation of PspCN and Related Proteins

Further work was conducted to investigate the properties of PspCN, variants of PspCN and therapeutic uses of such proteins.

Methods

Protection Against Haemolysis of PNH-Like Erythrocyte

PNH-like human erythrocytes were prepared according to a modified version of Ezzell et al. (1991). Briefly, whole human blood was obtained from donors by phlebotomy and stored in Alsever's solution at 4° C. Calls were washed three times with RBC Wash Buffer (20 mM HEPES; 145 mM NaCl; 10 mM EDTA; 0.1% w/v gelatine, pH 7.3) and re-suspended after the final wash in PBS. After each wash step the top 10% of the cell pellet was aspirated to remove the white cell-containing buffy coat. A 1-ml aliquot of packed cells was added to an 8% w/v solution of 2-amino-ethylisothiouronium bromide (AET. Sigma-Aldrich) solution that had been titrated to pH 8.0 using HCl. The cell suspension was incubated for nine minutes at 37° C. with constant agitation, after which time the cells were washed three times with RBC Wash Buffer containing no EDTA.

PNH-like cells were then washed once with 20 mM HEPES; 145 mM NaCl; 0.1% w/v gelatine, pH 6.4. These cells were then incubated at 37° C. with acidified normal human serum, 5 mM magnesium EGTA, and the appropriate concentration of either plasma-purified CFH (Complement Technology) or purified recombinant PspCN in a total reaction volume of 50 µl. After 30 minutes the reaction was quenched by the addition of 200 µl of ice-cold quench buffer (20 mM HEPES; 145 mM NaCl; 10 mM EDTA; 0.1% w/v gelatine; pH 7.3). The cells and cell debris were removed by centrifugation at 3,000×g for 10 minutes at 4° C., after which a 100-µl aliquot was removed and its absorbance at 410 nm recorded.

Determination of the Minimum PspC Sequence Necessary for Factor H Binding

Constructs containing the coding sequence for PspC (52-140), PspC (62-140), PspC (72-140), PspC (37-130), PspC (37-120) and PspC (37-110) were produced according to the method used to make the PspCN (37-140) sequence, CFH binding was then assessed using the same SPR assay that had been developed to determine the CFH-binding affinity of the PspCN (37-140) protein.

Modification of PspCN

The N and C termini of PspCN were modified to contain a cysteine and flexible peptide linker segment. In the case of the N-terminally Cys modified PspCN (Cys-PspCN) the extra residues included were: CGSGSGSGSGG-PspCN (SEQ ID NO 7), and in the case of the C-terminally Cys modified PspCN (PspCN-Cys) the extra residues included were: PspCN-GSGSGSGSGGC' (SEQ ID NO 8). These modified versions of PspCN were cloned and expressed as SUMO-fusion proteins in *E. coli* using the same methods as had been developed for PspCN. The purification of these proteins was also similar to that used for PspCN with the exception that tris(2-carboxyethyl)phosphine (TCEP) was included during all steps of purification in order to preserve the thiol groups of the cysteine residues.

SPR Experiments to Determine Whether the Cys-Mutated Proteins Retain FH Binding Ability SPR was performed using His-SUMO-Cys-PspCN and His-SUMO-PspCN-Cys as the ligand in SPR experiments and commercially available plasma-purified CFH (Complement Technology, Tyler Tex.), using the same method as that used to assess the CFH-binding ability of sPspCN.

PEGylation of Cys-PspCN

Cys-PspCN was mixed with a 20-fold molar excess of methoxy-PEG-maleimide (Sigma Aldrich) and incubated for 2.5 h at room temperature with stirring in PBS supplemented with 1 mM TCEP. Aliquots of the putatively PEGylated Cys-PspCN were subjected to SDS-PAGE under reducing conditions. Successfully PEGylated protein was judged to be that which displayed a band shift relative to the untreated protein.

Quantification of CFH Levels in Normal Human Serum

ELISA style assays to quantify CFH levels in normal human serum were carried out in standard flat-bottomed 96-well plates. Wells were coated with sPspCN (100 µl; 8 µg/ml) overnight at 4° C. and were subsequently blocked using phosphate buffered saline (PBS) supplemented with 5% w/v fat-free dried milk powder. Wells were washed three times with PBS supplemented with 0.05% v/v Tween 20. Wells were then incubated with for one hour at room temperature with a 1:800 dilution of the primary antibody (OX24-Biotin (Lifespan Biosciences LS-C62878)). Wells were then washed three times with PBS supplemented with 0.05% v/v Tween 20. Wells were then incubated with for one hour at room temperature with a 1:250 dilution of streptavidin-peroxidase polymer ultrasensitive (Sigma-Aldrich S-2438). Wells were then washed three times with PBS supplemented with 0.05% v/v Tween 20. Wells were then incubated for 20 minutes with o-phenylenediamine dihydrochloride (OPD) substrate followed by the addition of an equal volume of 2.5 M $H_2SO_4$. The absorbance of the wells was read at 490 nm.

Results

Figure 9A:
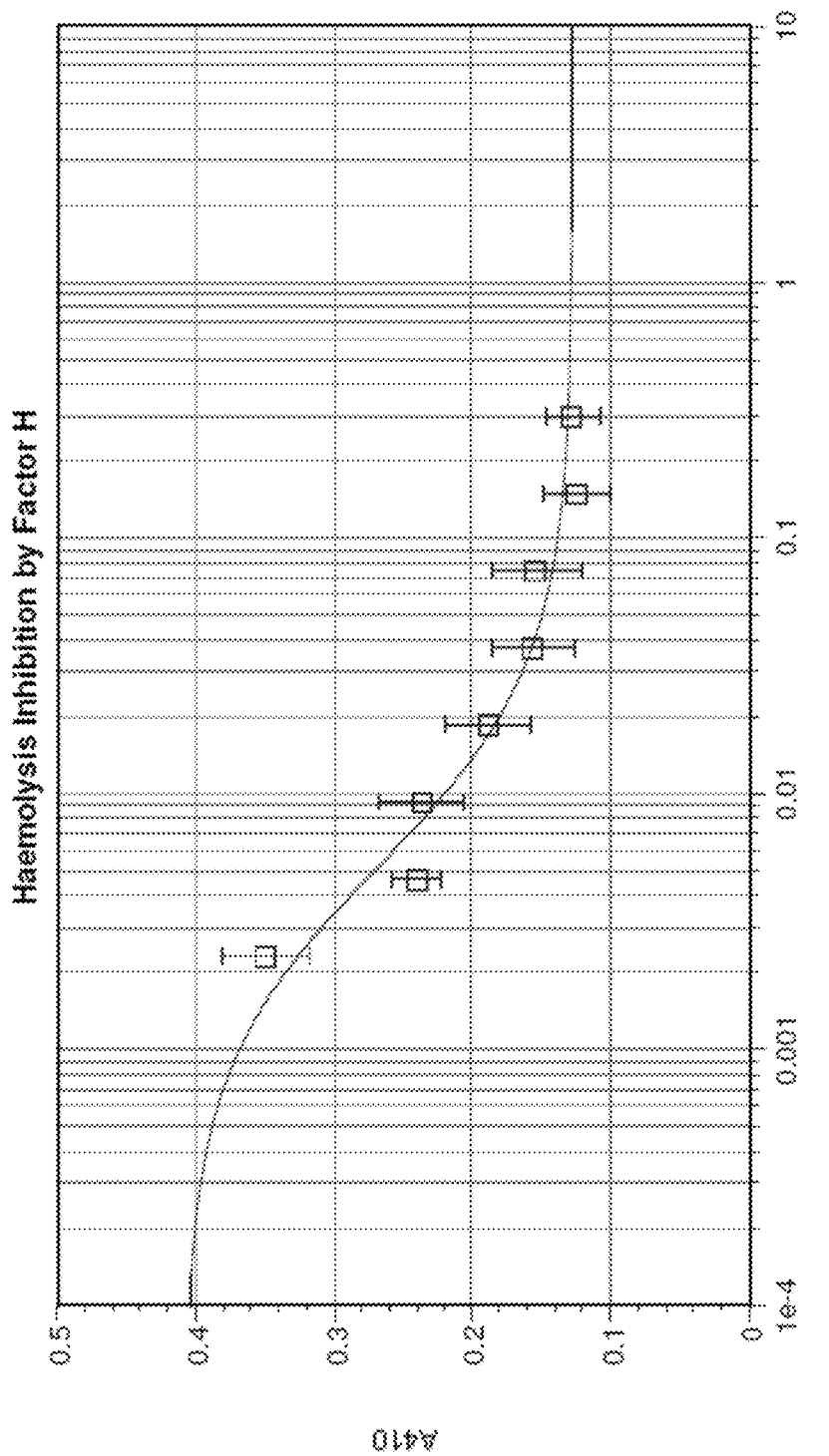
FIG. 9A: Adding increasing concentrations of Factor H inhibits lysis of the PNH-like erythrocytes.
Figure 9B:
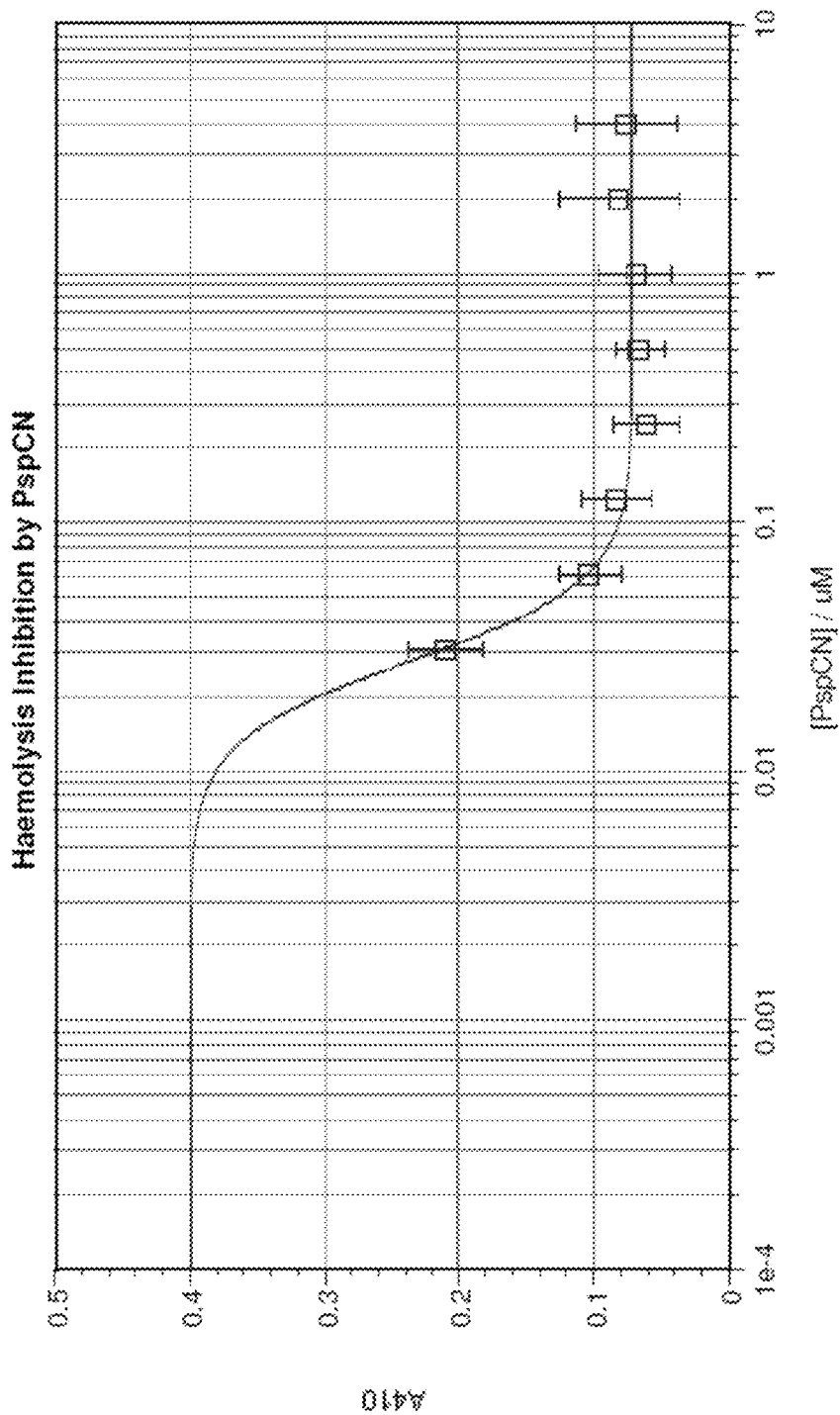
FIG. 9B: Adding increasing concentrations of PspCN inhibits lysis of the PNH-like erythrocytes with an $IC_{50}$ of 28 nM. PspCN activates the CFH already present in the serum and effectively prevents lysis.

PspCN is able to inhibit haemolysis of 'PNH-like' erythrocytes by acidified serum. The results of the haemolysis assay in FIG. 9A and FIG. 9B show that haemolysis can be effectively inhibited by the addition of CFH. Moreover, the addition of PspCN to the reaction inhibited the haemolysis even more efficiently (with an $IC_{50}$ value calculated to be 28 nM). The most likely explanation for this observation, when combined with the results of the results of the assays of binding of CFH to C3b and C3d, is that the addition of PspCN activates the endogenous CFH in the serum.

The Minimum Sequence Necessary for Wild-Type Factor H Binding is 62-140

The sensorgrams shown in FIGS. 10 A-F show that truncating PspCN (residues 37-140) from the C-terminus causes a decrease in binding affinity of at least three orders of magnitude, whereas it is possible to remove at least 24 residues from the N terminus and still retain very high CFH binding affinity. On the other hand, the PspC (71-140) protein shows a decrease in binding of at least three orders of magnitude. It remains to be confirmed that the 62-140 construct also retains the ability to stabilise CFH in the activated conformation.

Figures 11A, 11B:
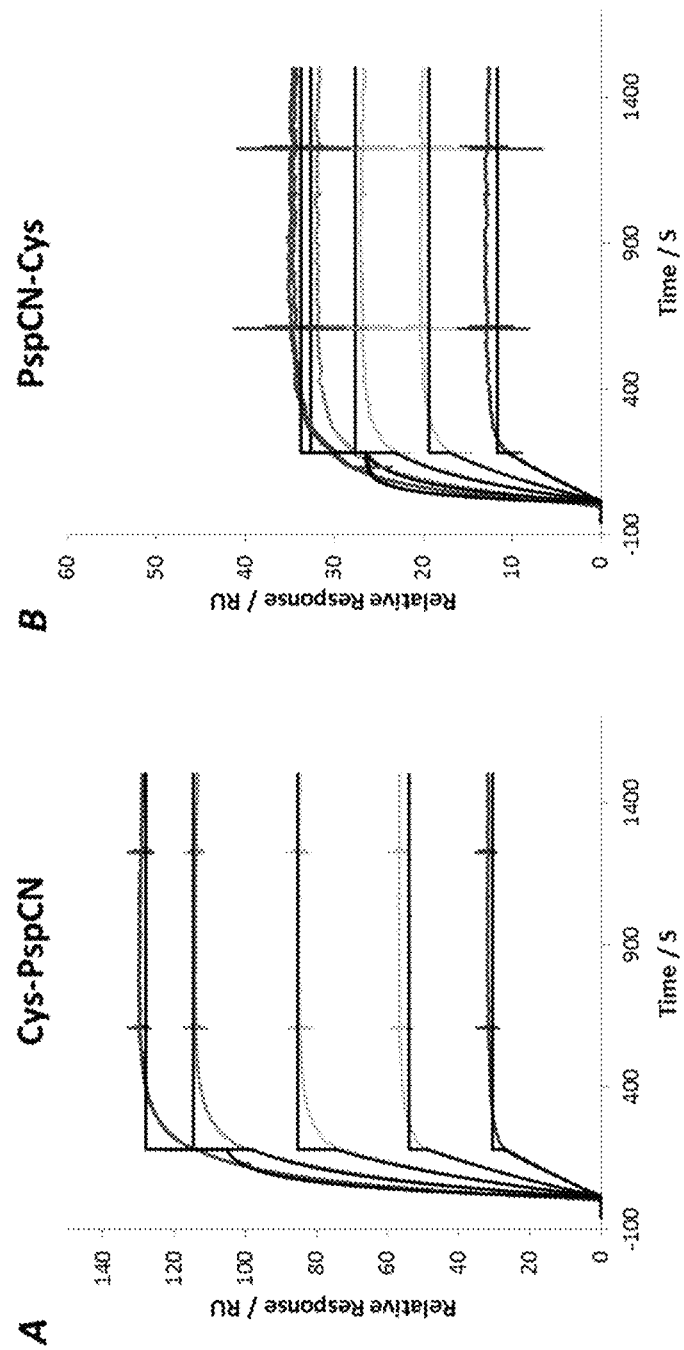
FIGS. 11A-11B show sensorgrams indicating that, as is the case for wild-type PspCN, both Cys-PspCN (FIG. 11A) and PspCN-Cys (FIG. 11B) have the ability to bind almost irreversibly to CFH, showing no detectable off rate.

Cys-Modified PspCN Binds to Factor H with a Similar Affinity to Native-Sequence PspCN The shape of the curves shown in FIGS. 11A-11B indicate that, as is the case for wild-type PspCN, both Cys-PspCN (FIG. 11A) and PspCN-Cys (FIG. 11B) have the ability to bind effectively irreversibly to CFH, showing no detectable off rate. Kinetic analysis of the interactions of Cys-PspCN and PspCN-Cys performed using Biacore evaluation software, suggested the $K_D$ for the interaction to be approximately $10^{-13}$ M (although the interaction was too tight for an accurate $K_D$ to be calculated using SPR). This calculated $K_D$ is the same order of magnitude as that calculated for unmodified PspCN.

Figure 15:
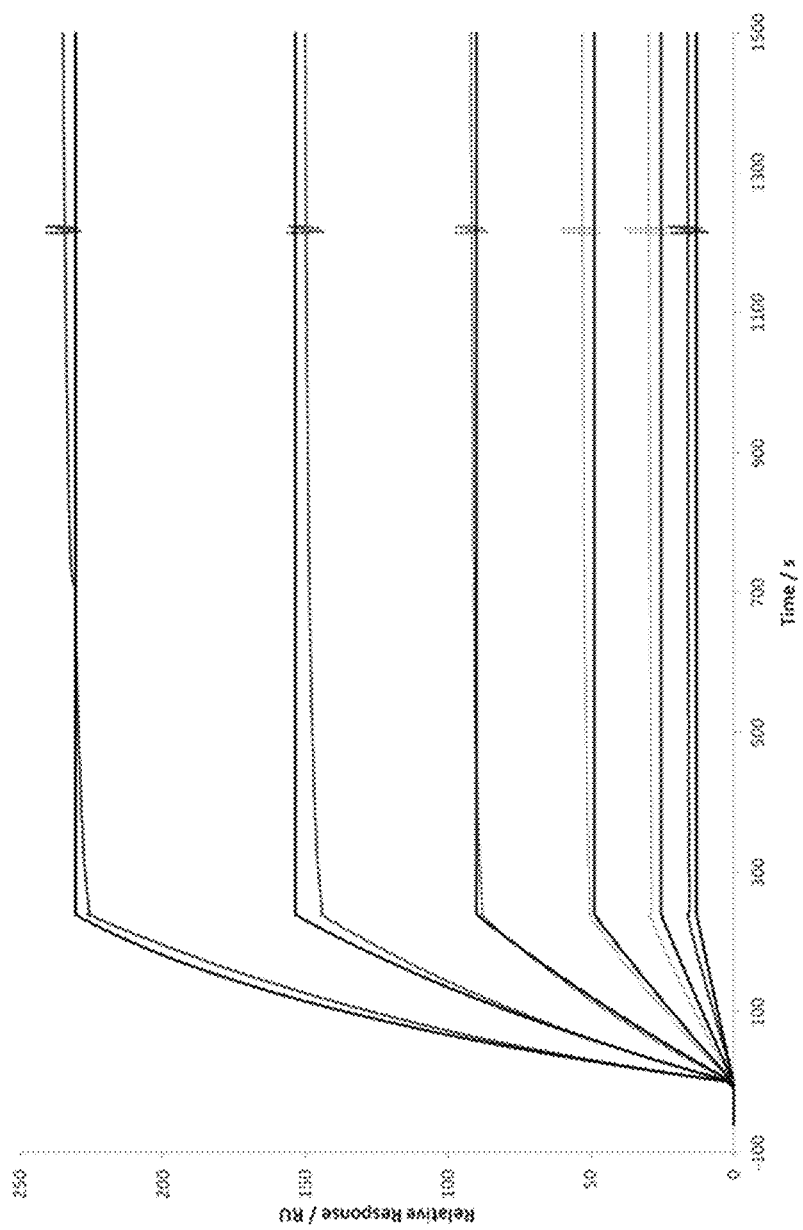
FIG. 15 shows cysteine tagged PspCN retain their CFH binding ability when coupled through their thiols.

Furthermore, FIG. 15 shows that coupling the cysteine tagged PspCN to a surface through the thiol group does not impair their CFH binding affinity.

Figure 16:
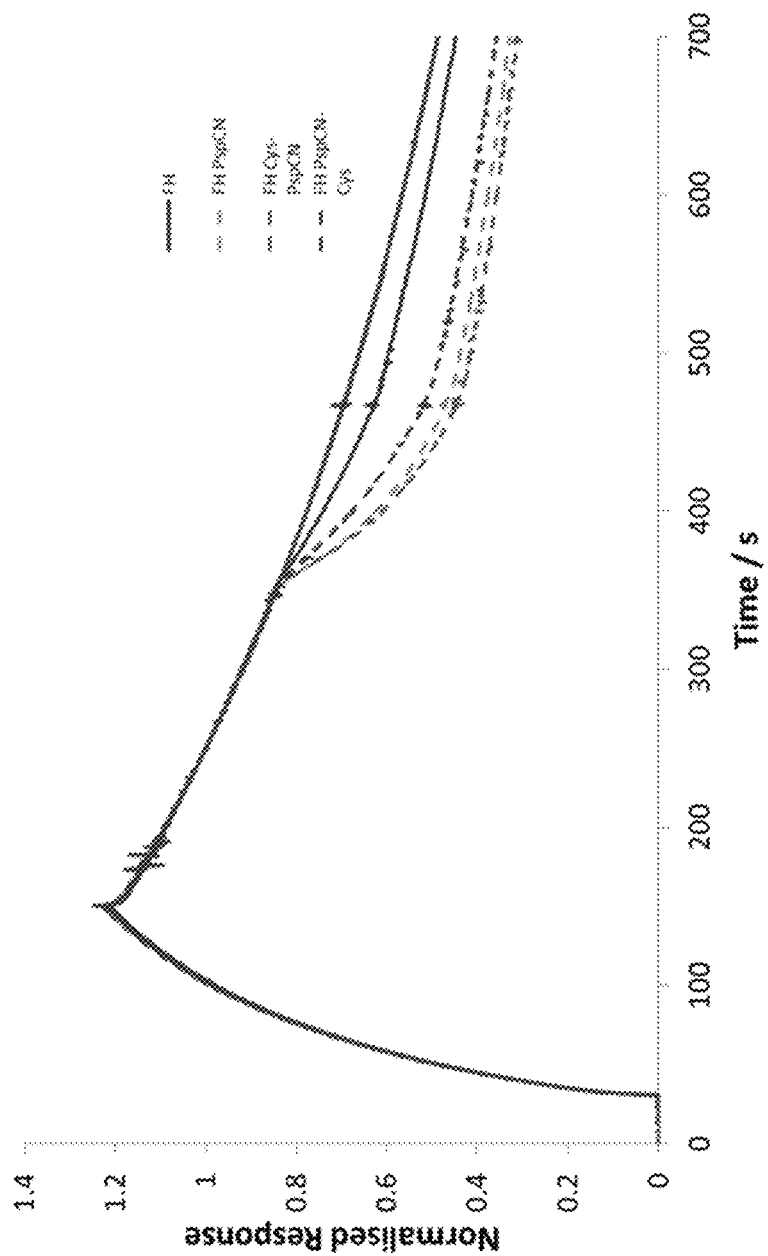
FIG. 16 shows that cysteine tagged PspCN shows a similar decay acceleration activity of CFH as PspCN without a cysteine tag.

In addition, with reference to FIG. 16, the cysteine tagged PspCN protein shows similar decay acceleration activity as PspCN without a cysteine tag. Therefore, the presence of a cysteine tag on PspCN has been shown to have minimal effect on the interaction between PspCN and CFH.

Cys-PspCN can be Effectively PEGylated with Methoxy-PEG-Maleimide

Figure 12:
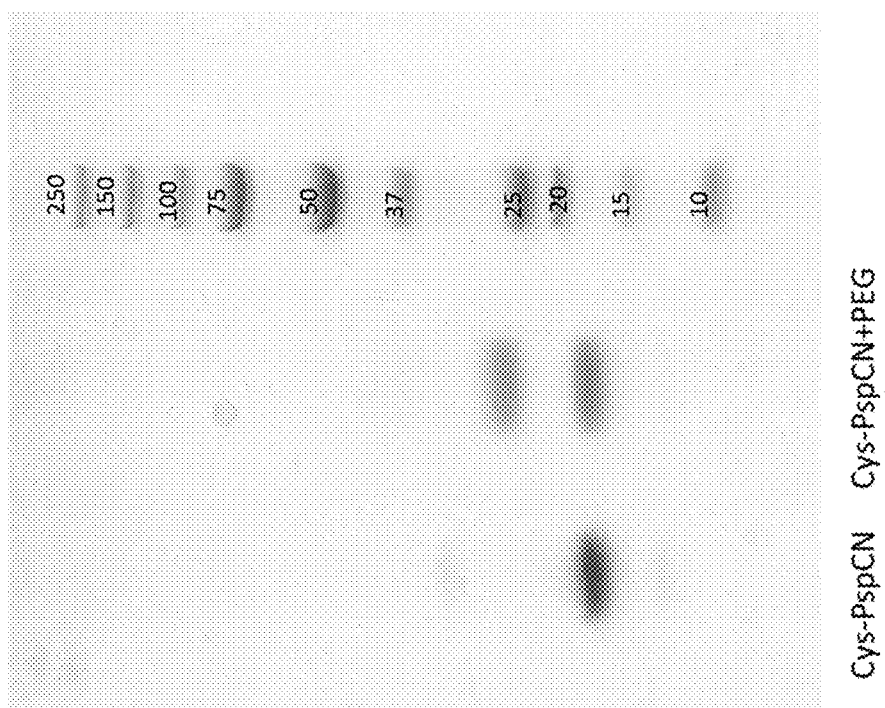
FIG. 12 shows a gel indicating that methoxy-PEG-maleimide efficiently couples to Cys-PspCN under mild conditions as can be seen by a shift in mobility under SDS-PAGE.

Methoxy-PEG-maleimide efficiently couples to Cys-PspCN under mild conditions as can be seen in FIG. 12 by a shift in mobility under SDS-PAGE. The lower band, migrating between the 15-kDa and 20-kDa markers represents unmodified PspCN. Following the PEGylation reaction there is still a significant amount of PspCN that remains not PEGylated. The upper band, migrating just above the 25-kDa marker, on the other hand represents PspCN that has been successfully PEGylated. There is little evidence of the formation of PspCN disulfide-linked dimers, or PspCN species with multiple PEG moieties. Overall this method of PEGylation of PspCN gave an approximate 50% yield of PEGylated PspCN; more quantitative studies would be required to determine the percentage yield more accurately.

CFH can Effectively be Quantified Using PspCN in an 'ELISA Style' Assay

Figure 13:
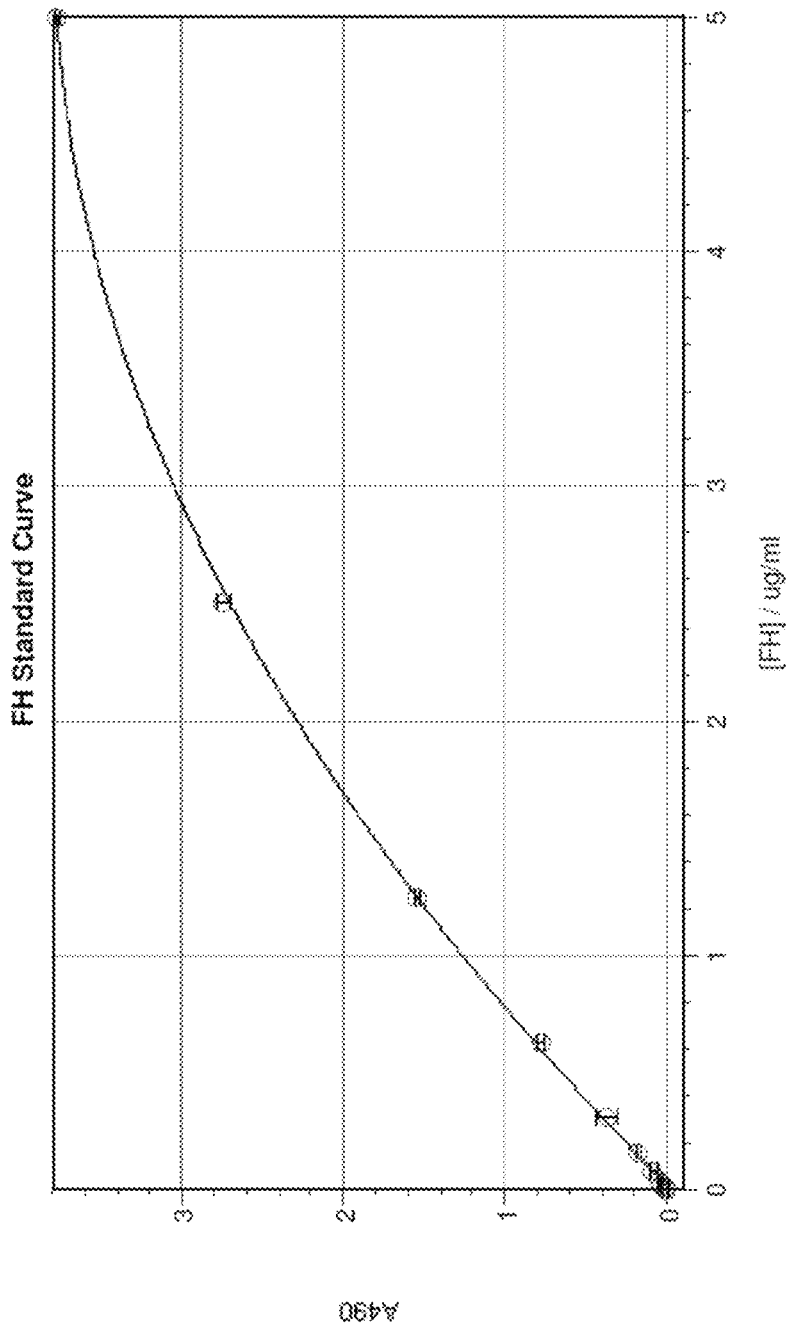
FIGS. 13A-13B shows the use of a PspCN-based sandwich ELISA to quantify purified CFH in PBS as used to make a standard curve (FIG. 13A) and to quantify the CFH present in dilutions of normal human serum (FIG. 13B).
Figure 13:
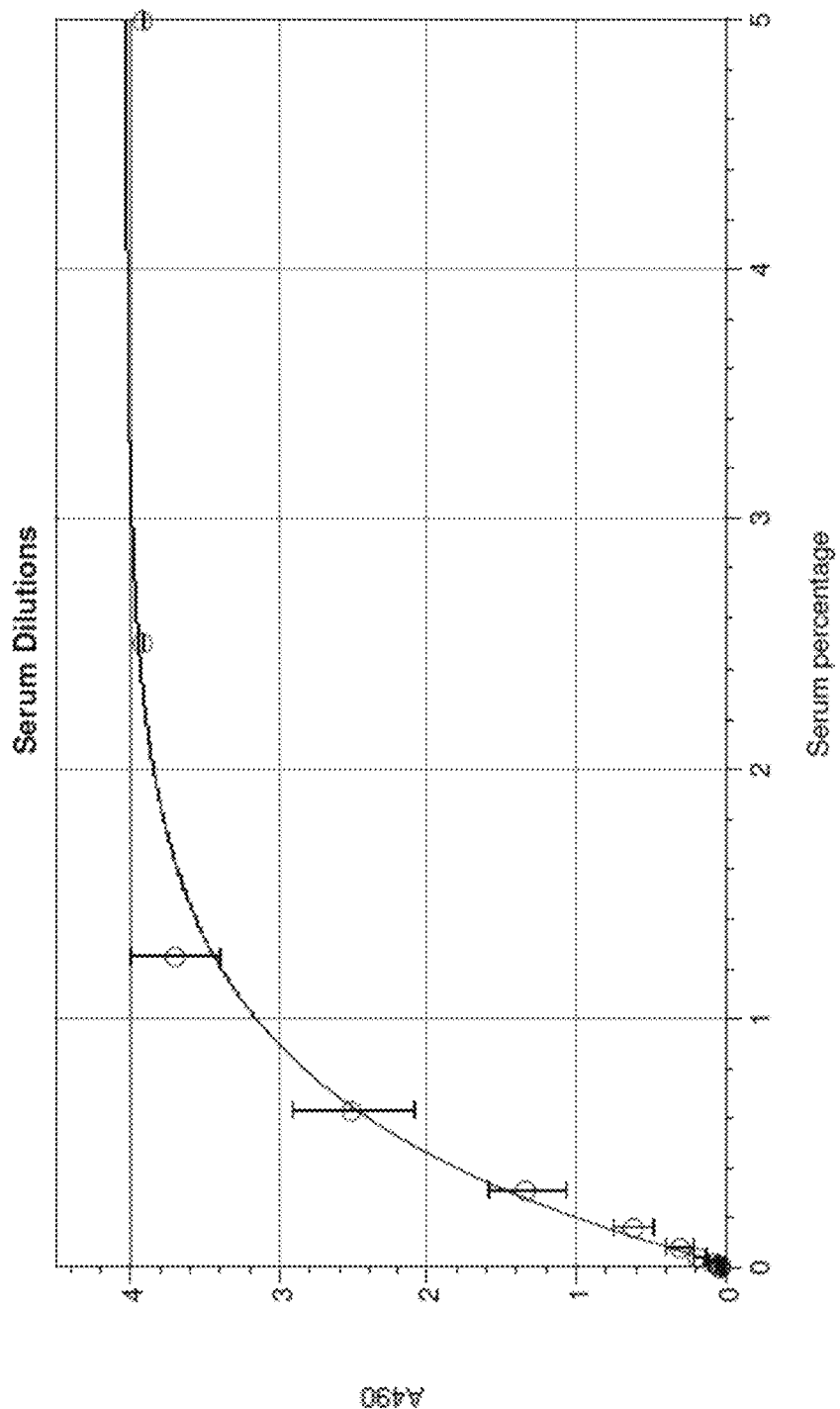

Plasma-purified CFH (Complement Technology), at known concentrations, was used to build up a standard curve (FIG. 13A), which gave good linear detection over at least two orders of magnitude. When compared to the standard curve, CFH levels in normal human serum could be determined and were found to lie within the currently accepted reference range (FIG. 13B).

Preparing the PspCN Affinity Chromatography Resin

PspCN (37-140) modified to contain an N-terminal Cys residue and a linker comprised of the residues GSGSGSGSGG (Cys-PspCN) was coupled to Ultralink iodoacetyl chromatography resin (Thermo Scientific) via its N-terminal Cys residue. The coupling was performed based on the manufacturer's instructions. Ultralink iodoacetyl resin (10 ml) was washed with 50 ml of coupling buffer (50 mM Tris, 5 mM EDTA, pH 8.5) using a gravity fed chromatography column. A solution of Cys-PspCN (20 ml at 2 mg/ml) in coupling buffer supplemented with 2.5 mM TCEP was mixed with the Ultralink iodoacetyl resin for 15 minutes at room temperature in a gravity fed chromatography column. The column was then stood upright and incubated for a further 30 minutes at room temperature. Unbound Cys-PspCN was then removed by draining off the fluid phase and washing the column with 30 ml of coupling buffer. To block unreacted iodoacetyl groups on the resin, the resin was then mixed with 20 ml of 50 mM L-cysteine.HCl in coupling buffer for 15 minutes at room temperature. The column was then stood upright and incubated for a further 30 minutes at room temperature. The resin was then washed with 60 ml of 1 M NaCl followed by 60 ml of phosphate buffered saline (PBS) supplemented with 0.05% $NaN_3$. Using this method approximately 1-1.5 mg of Cys-PspCN was coupled to each ml of resin.

Purification of FH from Human Plasma

Human plasma (normal mixed pool) in Alsever's solution was purchased from ICS Biosciences. The PspCN resin (5 ml) was incubated with 100 ml of the human plasma at 4° C. for 1 hour. Following the incubation the mixture was applied to an empty gravity fed chromatography column and the plasma drained off. The resin was then washed with 3×50 ml of HBS (20 mM HEPES; 150 mM NaCl; pH 7.5), followed by a further wash with 2×50 ml of 4 M NaCl. Highly purified FH was eluted from the column using 0.1 M glycine buffer, pH 2.5.

The successful isolation of FH from human plasma is shown in the gels of FIG. 17, where clear CFH bands can be seen for each stage of the above purification process.

Use of PspCN to Protect Surfaces

Figure 18:
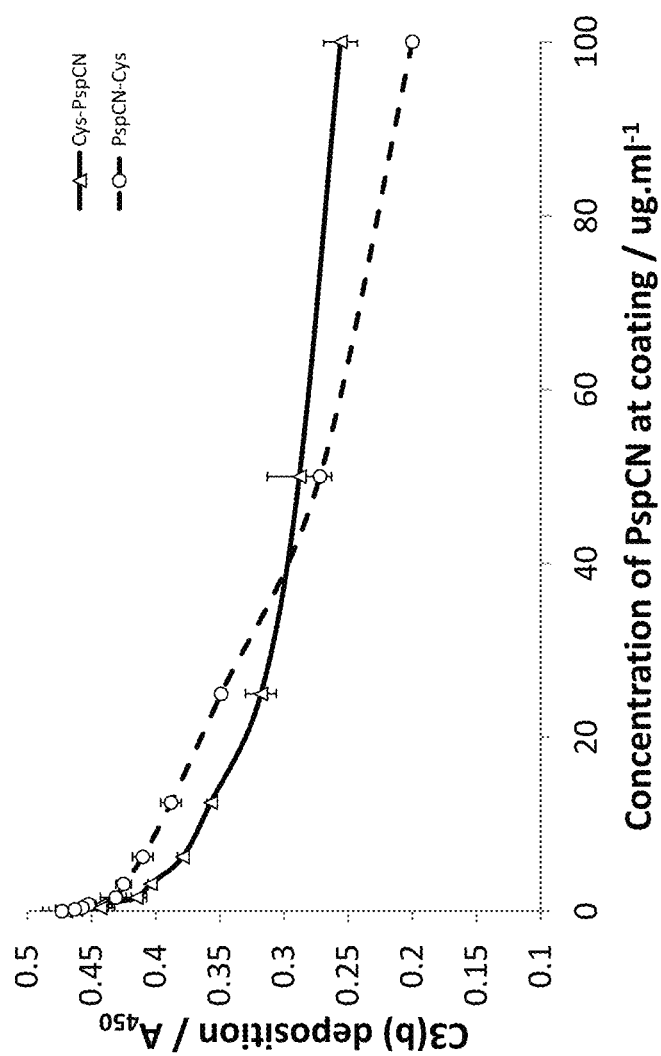
FIG. 18 shows that cysteine lagged PspCN immobilised on maleimide activated polystyrene protects the surface from complement to an extent dependent on coupling density upon exposure to normal human serum.

With reference to FIG. 18, cysteine tagged PspCN was immobilised onto a maleimide activated polystyrene 96 well plates (Pierce) according to the manufacturer's instructions using different concentrations of Cys-PspCN in the coupling buffer as shown. The wells were subsequently incubated with fresh normal human serum at room temperature to allow complement deposition to occur. Deposition of C3b to the surface was detected using an anti C3 antibody in a method analogous to a conventional ELISA protocol. Deposited C3b was measured as a function of the concentration of PspCN in the coupling buffer. For both N-terminally and C-terminally cysteine tagged PspCN, the deposition of C3b was decreased by approximately 50% on surfaces that had been coated with 100 µg/ml PspCN.

Accordingly, the presence of a PspCN coating at a surface can significantly reduce the deposition of C3b on that surface, and therefore, reduce the immunoresponse to that surface.

Use of PspCN as a Diagnostic to Detect the Presence of Anti-FH Autoantibodies

Figure 19:
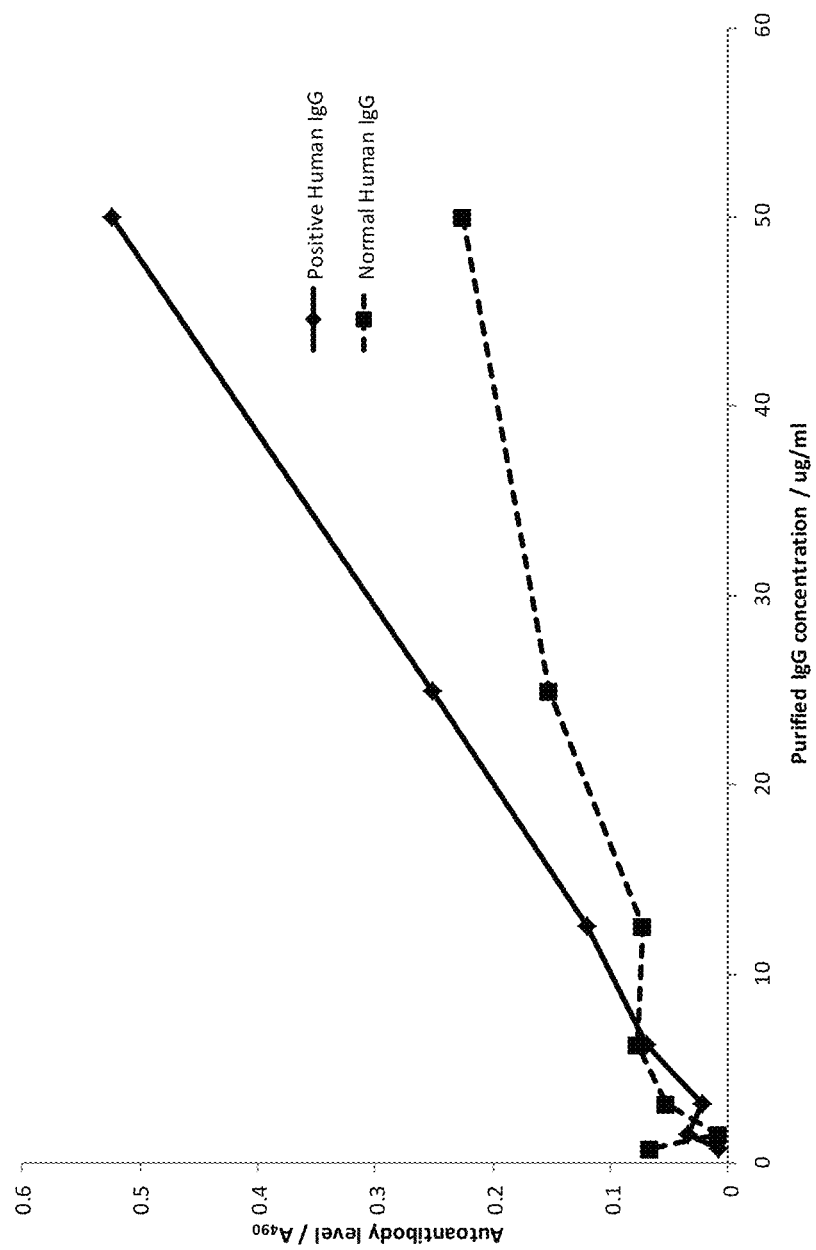
FIG. 19 Shows the detection of anti-FH autoantibodies using PspCN to couple FH to a polystyrene plate in an ELISA type assay. Purified IgG was used from a patient previously shown to be positive for anti-FH autoantibodies alongside purified IgG from normal human serum. The graph clearly shows significantly more signal is detected in the positive sample than in the control at a level that is dependent on the concentration of purified IgG used in the assay.

With reference to FIG. 19 Cys-PspCN was immobilised onto maleimide activated 96 well plates (Pierce) according to the manufacturer's instructions using a concentration of PspCN in the coupling buffer of 50 µg/ml. The plates were subsequently incubated with purified human factor H, before being incubated with purified IgG derived either from a patient known to be positive for anti-FH autoantibodies or a normal control. Anti-FH autoantibodies were subsequently defected using an anti-human IgG specific antibody conjugated to biotin, followed by streptavidin peroxidase in a mannor analogous to a standard ELISA. The wells were washed thrice with phosphate buffered saline between subsequent incubations.

TIGR4 Strain

Fragments of the PspC protein of the TIGR4 strain of *Streptococcus pneumonia*, referred to here as TIGR4 PspC, was shown to bind tightly to CFH. TIGR4 PspC (37-179) binds CFH with a $K_D$ of $10^{-16}$ M and TIGR4 PspC (68-148) binds CFH with a $K_D$ pf $10^{-15}$ M.

Figures 20A, 20B:
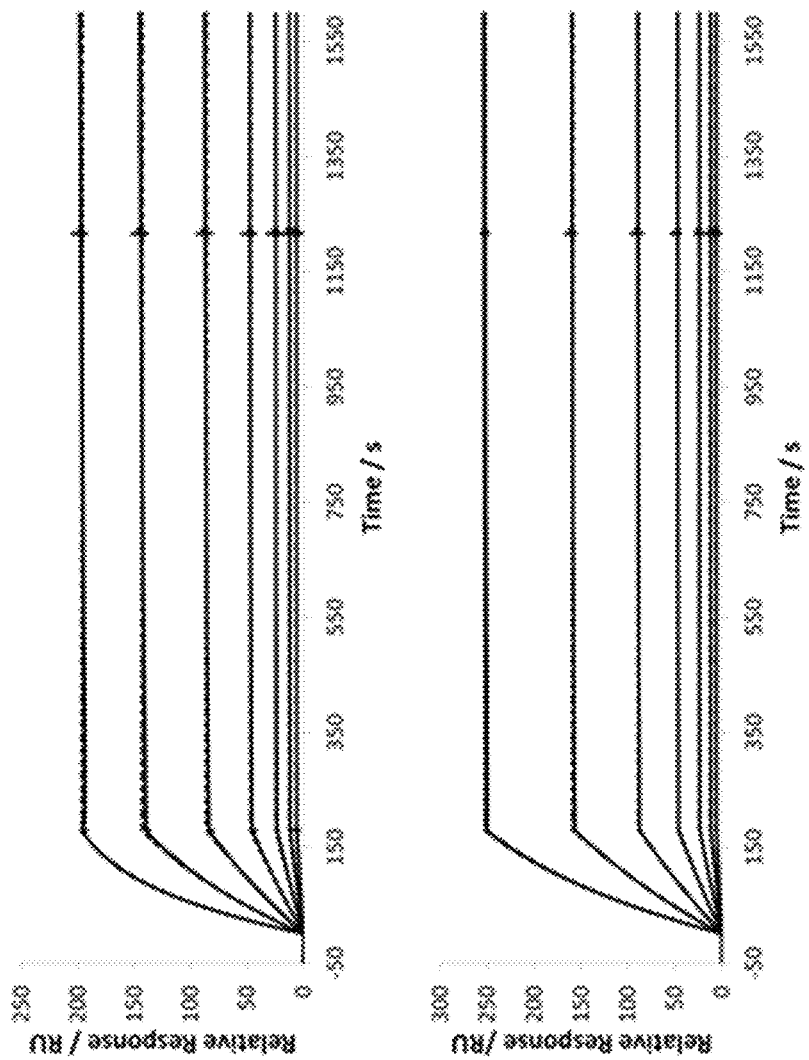
FIGS. 20A-20B show SPR sensorgrams showing immobilised PspCN from strain TIGR4 binding to FH.

Ability of PspCN (CbpN) from *S. Pneumoniae* Strain TIGR4 to Bind to and Activate CFH With reference to FIGS. 20A-20B from strain TIGR4 of *S. pneumoniae* was coupled to a Biacore NTA chip in an identical manner to that used to test PspCN from strain D39. Sensorgrams were acquired showing the binding to a fragment of PspCN from strain TIGR4 comprising either residues 37-179 or residues 68-148. In each case binding of FH to the TIGR4 derived PspCN sequences resulted in a similarly tight binding to that observed for the D39 strain with KDs in the $10^{-16}$ M range calculated in each case.

Figure 21:
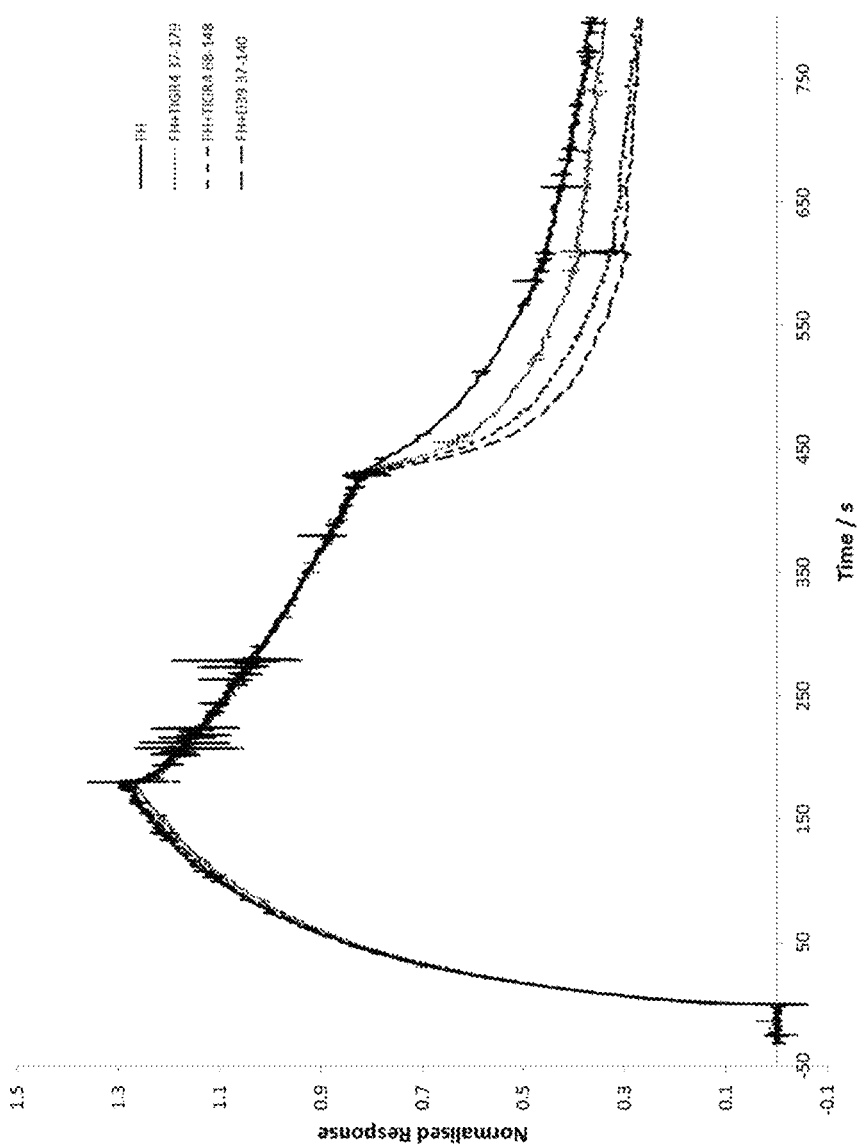
FIG. 21 Shows the increase in decay acceleration activity of FH in complex with PspCN from TIGR4 residues 37-179 or residues 68-148. It is also clear that TIGR4, like D39, contains no intrinsic decay acceleration activity.
Figures 22A, 22B:
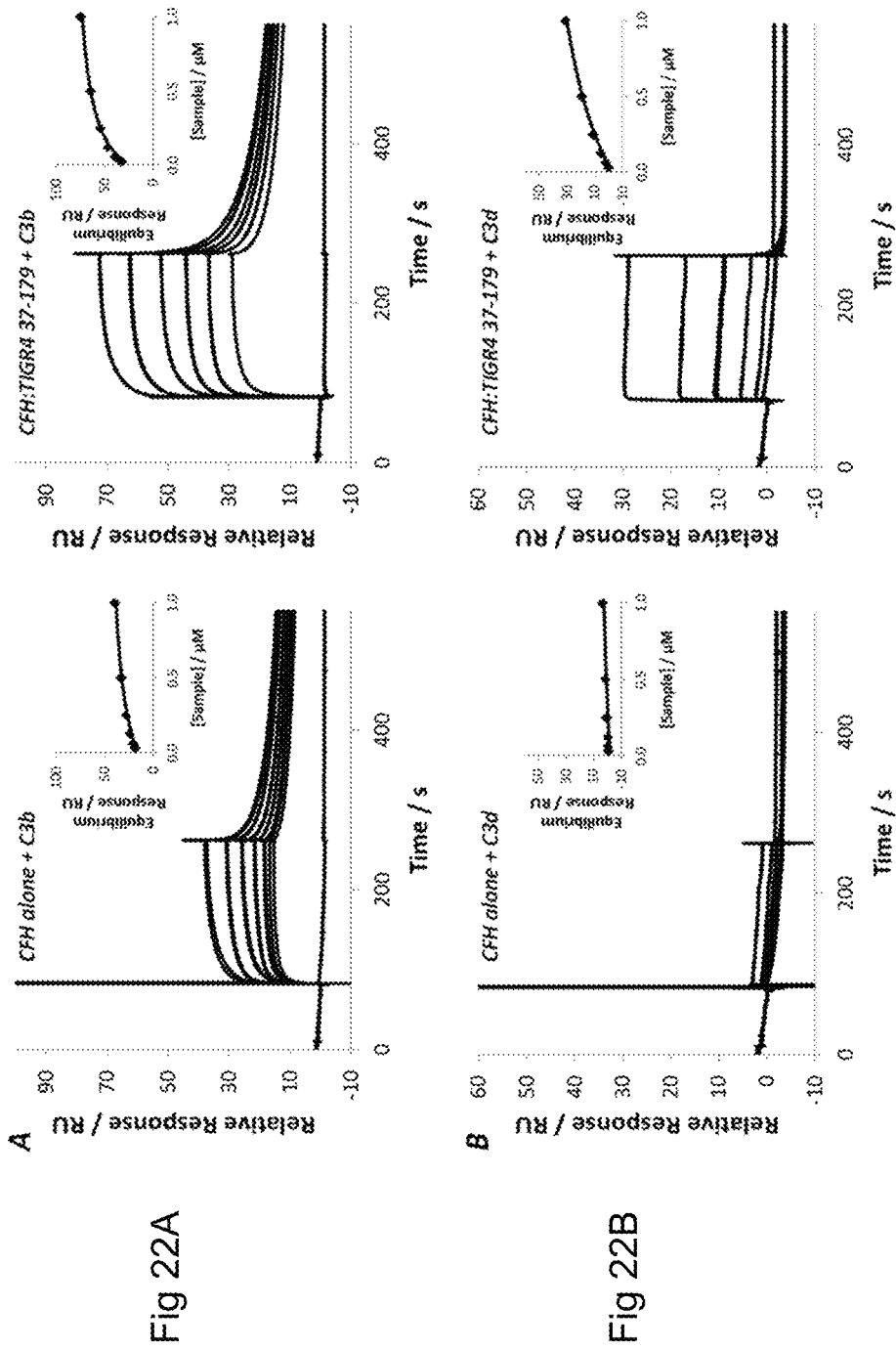
FIGS. 22A-22D Sensorgrams showing that PspCN (CbpA) from *S. pneumoniae* has the ability to activate CFH by increasing the affinity of the FH:PspCN complex for C3b and C3d.
Figures 22C, 22D:
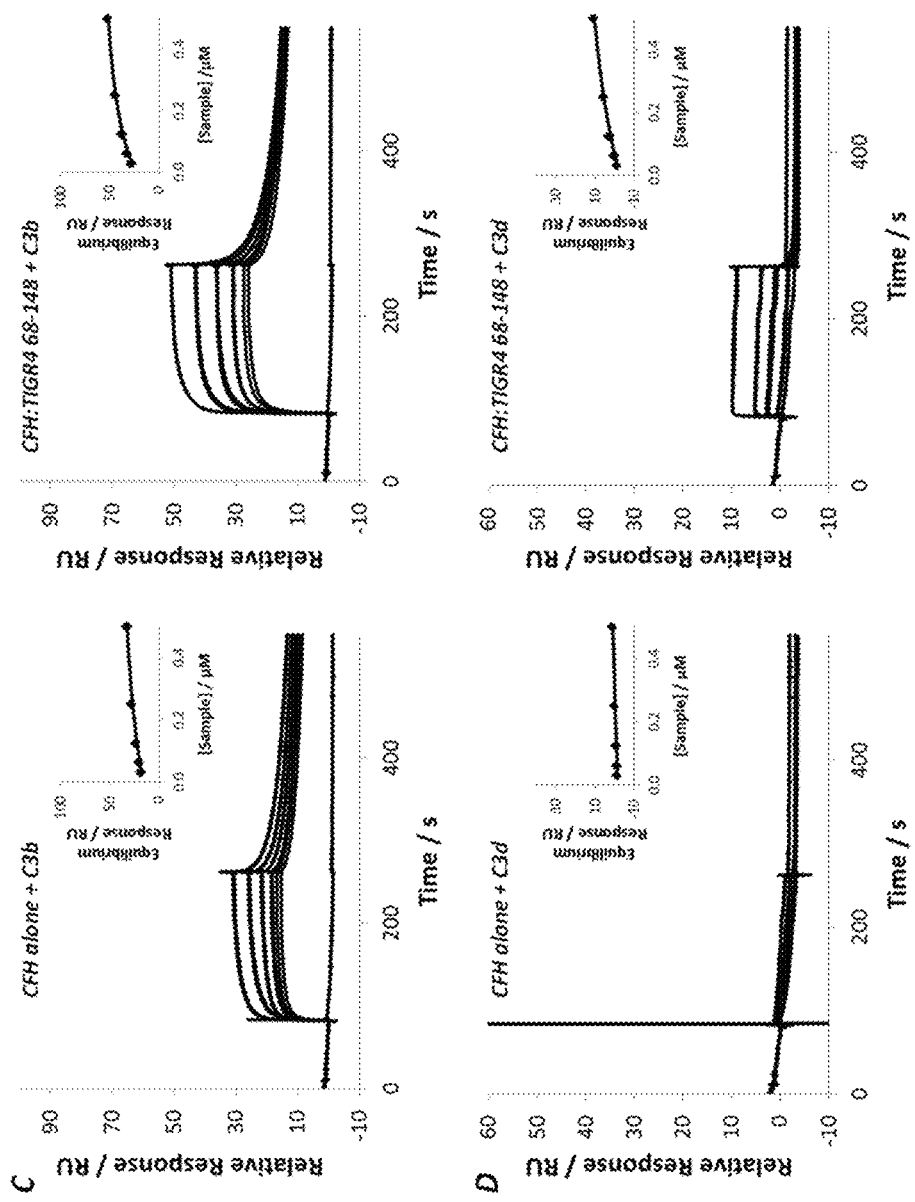

With reference to FIG. 21, Biacore based decay acceleration assays were performed to test the effect on decay acceleration activity of PspCN (TIGR4) binding to FH in an identical manner as those used to test the PspCN fragments derived from the D39 strain. In the case of both PspCN (TIGR4 residues 37-179) and PspCN (TIGR4 residues 68-148) binding of the PspCN fragment to FH caused an increase in the ability of FH to accelerate the decay of the C3 convertase (C3bBb). The PspCN fragments alone showed no intrinsic decay acceleration activity.

With reference to FIGS. 22A-22D and Table 3, Biacore based binding assays were performed to test the effect that PspCN (TIGR4) binding to FH had on the affinity of FH for C3b and C3d in an identical manner as those used to test the D39 derived PspCN fragments. In each case the binding of either PspCN (TIGR4 residues 37-179) or PspCN (TIGR4 residues 68-148) to CFH caused a significant increase in C3b binding and a large increase in the otherwise undetectable C3b binding affinity of CFH.

TABLE 3

| Construct | C3b | | | C3d | | |
|---|---|---|---|---|---|---|
| | $K_D$/M | $SE(K_D)$ | $Chi^2/RU^2$ | $K_D$/M | $SE(K_D)$ | $Chi^2/RU^2$ |
| CFH | 5.5e−7 | 7.8e−8 | 0.35 | N/A | N/A | N/A |
| CFH:TIGR4 (37-179) | 2.8e−7 | 3.3e−8 | 1.15 | 1.2e−6 | 8.4e−8 | 0.10 |

REFERENCES FOR EXAMPLE 2

Brooks-Walter et al. (1989) Infect Immun. 1999 December; 67(12): 6533-6542.

Ezzell, J L et al. (1991) Blood 77:2764-2773

```
Relevant Sequences
D39 PspC gene sequence - complete CDS (SEQ ID NO 3)
    1 atgcttgtca ataatcacaa atatgtagat catatcttgt ttaggacagt aaaacatcct 61 aattactttt taaatattct tcctgagttg attggcttga ccttgttgag tcatgcttat 121 gtgacttttg ttttagtttt tccagtttat gcagttattt tgtatcgacg aatagctgaa 181 gaggaaaagc tattacatga agttataatc ccaaatggaa gcataaagag ataaatacaa 241 aattcgattt atatacagtt catattgaag taatatagta aggttaaaga aaaaatatag 301 aaggaaataa acatgtttgc atcaaaaagc gaaagaaaag tacattattc aattcgtaaa 361 tttagtattg gagtagctag tgtagctgtt gccagtcttg ttatgggaag tgtggttcat 421 gcgacagaga acgagggaag tacccaagca gccacttctt ctaatatggc aaagacagaa 481 cataggaaag ctgctaaaca agtcgtcgat gaatatatag aaaaaatgtt gagggagatt 541 caactagata gaagaaaaca tacccaaaat gtcgccttaa acataaagtt gagcgcaatt 601 aaaacgaagt atttgcgtga attaaatgtt ttagaagaga agtcgaaaga tgagttgccg 661 tcagaaataa aagcaaagtt agacgcagct tttgagaagt ttaaaaaaga tacattgaaa 721 ccaggagaaa aggtagcaga agctaagaag aaggttgaag aagctaagaa aaaagccgag 781 gatcaaaaag aagaagatcg tcgtaactac ccaaccaata cttacaaaac gcttgaactt 841 gaaattgctg agttcgatgt gaaagttaaa gaagcggagc ttgaactagt aaaagaggaa 901 gctaaagaat ctcgaaacga gggcacaatt aagcaagcaa aagagaaagt tgagagtaaa 961 aaagctgagg ctacaaggtt agaaaacatc aagacagatc gtaaaaaagc agaagaagaa 1021 gctaaacgaa aagcagatgg taagttgaag gaagctaatg tagcgacttc agatcaaggt 1081 aaaccaaagg ggcgggcaaa acgaggagtt cctggagagc tagcaacacc tgataaaaaa 1141 gaaaatgatg cgaagtcttc agattctagc gtaggtgaag aaactcttcc aagctcatcc 1201 ctgaaatcag gaaaaaaggt agcagaagct gagaagaagg ttgaagaagc tgagaaaaaa 1261 gccaaggatc aaaaagaaga agatcgccgt aactacccaa ccaatactta caaaacgctt 1321 gaccttgaaa ttgctgagtc cgatgtgaaa gttaaagaag cggagcttga actagtaaaa 1381 gaggaagcta aggaacctcg agacgaggaa aaaattaagc aagcaaaagc gaaagttgag 1441 agtaaaaaag ctgaggctac aaggttagaa aacatcaaga cagatcgtaa aaaagcagaa 1501 gaagaagcta acgaaaagc agcagaagaa gataaagtta agaaaaaacc agctgaacaa 1561 ccacaaccag cgccggctac tcaaccagaa aaaccagctc aaaaccaga gaagccagct 1621 gaacaaccaa aagcagaaaa aacagatgat caacaagctg aagaagacta tgctcgaaga 1681 tcagaagaag aatataatcg cttgactcaa cagcaaccgc caaaaactga aaaaccagca
```

-continued

```
1741 caaccatcta ctccaaaaac aggctggaaa caagaaaacg gtatgtggta cttctacaat 1801 actgatggtt caatggcaac aggatggctc caaaacaacg ttcatggta ctatctaaac 1861 gctaatggtc ctatggcgac aggatggctc caaaacaatg ttcatggta ctatctaaac 1921 gctaatggtt caatggcaac aggatggctc caaaacaatg ttcatggta ctacctaaac 1981 gctaatggtc ctatggcgac aggatggctc caatacaatg ttcatggta ctacctaaac 2041 agcaatggcg ctatggcgac aggatggctc caatacaatg gctcatggta ctacctcaac 2101 gctaatggtg atatggcgac aggatggctc caaaacaacg ttcatggta ctacctcaac 2161 gctaatggtg atatggcgac aggatggctc caatacaacg ttcatggta ttacctcaac 2221 gctaatggtg atatggcgac aggttgggtg aaagatggan atacctggta ctatcttaaa 2281 gcatcaggtg ctatgaaagc aagccaatgg ttcaaagtat cagataaatg gtactatgtc 2341 aatggctcag gtgcccttgc agtcaacaca actgtagatg gctatggagt caatgccaat 2401 ggtgaatggg taaactaaac ctaatataac tagttaatac tgacttcctg taagaacttt 2461 ttaaagtatt ccctacaaat accatatcct ttcagtagat aatatacccct tgtaggaagt 2521 ttagattaaa aaataactct gtaatctcta gccggattta tagcgctaga gactacggag 2581 ttttttttgat gaggaaagaa tggcggcatt caagagactc tttaagagag ttacgggttt 2641 taaactatta agccttctcc aattgcaaga gggcttcaat ctctgctagg gtgctagctt 2701 gcgaaatggc tccacggagt ttngc
```

Amino acid sequence transcribed from SEQ ID NO 3 (SEQ ID NO 4) - the PspCN sequence (amino acids 37 to 140) is shown in bold:
MFASKSERKVHYSIRKFSIGVASVAVASLVMGSVV**HATENEGSTQAATSSNMAKTEHRKAAKQVVDEY
IEKMLREIQLDRRKHTQNVALNIKLSAIKTKYLRELNVLEEKSKDELPSEIKAKLDAAFEKFKKDTLK
PGE**KVAEAKKKVEEAKKKAEDQKEEDRRNYPTNTYKTLELEIAEFDVKVKEAELELVKEEAKESRNEG
TIKQAKEKVESKKAEATRLENIKTDRKKAEEEAKRKADGKLKEANVATSDQGKPKGRAKRGVPGELAT
PDKKENDAKSSDSSVGEETLPSSSLKSGKKVAEAEKKVEEAEKKAKDQKEEDRRNYPTNTYKTLDLEI
AESDVKVKEAELELVKEEAKEPRDEEKIKQAKAKVESKKAEATRLENIKTDRKKAEEEAKRKAAEEDK
VKEKPAEQPQPAPATQPEKPAPKPEKPAEQPKAEKTDDQQAEEDYARRSEEEYNRLTQQQPPKTEKPA
QPSTPKTGWKQENGMWYFYNTDGSMATGWLQNNGSWYYLNANGAMATGWLQNNGSWYYLNANGSMATG
WLQNNGSWYYLNANGAMATGWLQYNGSWYYLNSNGAMATGWLQYNGSWYYLNANGDMATGWLQNNGSW
YYLNANGDMATGWLQYNGSWYYLNANGDMATGWVKDGXTWYYLKASGAMKASQWFKVSDKWYYVNGSG
ALAVNTTVDGYGVNANGEWVN The synthetic, codon-optimised DNA sequence that was used for the expression of PspCN is shown below (SEQ ID NO 5):
GCAACCGAAAATGAAGGTAGCACCCAGGCAGCAACCAGCAGCAATATGGCAAAAACCGAACATCGTAA

AGCAGCCAAACAGGTTGTGGATGAGTATATCGAAAAAATGCTGCGTGAAATTCAGCTGGATCGTCGTA

AACATACCCAGAATGTTGCACTGAACATTAAACTGAGCGCCATCAAAACCAAATATCTGCGTGAACTG

AATGTGCTGGAAGAGAAAAGCAAAGATGAACTGCCGAGCGAAATTAAAGCAAAACTGGATGCAGCCTT

TGAAAAATTCAAAAAAGATACCCTGAAACCGGGTGAGAAATAA

Human CFH amino acid sequence - signal peptide underline - un-procesed from (SEQ ID NO 6):
```
          10         20         30         40         50         60
MRLLAKIICL MLWAICVAED CNELPPRRNT EILTGSWSDQ TYPEGTQAIY KCRPGYRSLG 70         80         90        100        110        120
NVIMVCRKGE WVALNPLRKC QKRPCGHPGD TPFGTFTLTG GNVFEYGVKA VYTCNEGYQL 130        140        150        160        170        180
LGEINYRECD TDGWTNDIPI CEVVKCLPVT APENGRIVSS AMEPDREYHF GQAVRFVCNS
```

-continued

```
           190        200        210        220        230        240
    GYKIEGDKEM HCSDDGEWSK EKPKCVEISC KSPDVINGSP ISQKIIYKEN ERFQYEGNMG 250        260        270        280        290        300
    YEYSERGDAV CTESGWRPLP SCEEKSCDNP YIPNGDYSPL RIKHRTGDEI TYQCRNGFYP 310        320        330        340        350        360
    ATRGNTAKCT STGWIPAPRC TLKPCDYPDI KHGGLYHENM RRPYFPVAVG KYYSYYCDEH 370        380        390        400        410        420
    FETPSGSYND HIHCTQDGWS PAVPCLRKCY FPYLENGYNQ NYGRKFVQGK SIDVACHPGY 430        440        450        460        470        480
    ALPKAQTTVT CMENGWSPTP RCIRVKTCSK SSIDIENGFI SESQYTYALK EKAKYQCKLG 490        500        510        520        530        540
    YVTADGETSG SITCGKDGWS AQPTCIKSCD IPVFMNARTK NDFTWFKLND TLDYECHDGY 550        560        570        580        590        600
    ESNTGSTTGS IVCGYNGWSD LPICYERECE LPKIDVHLVP DRKKDQYKVG EVLKFSCKPG 610        620        630        640        650        660
    FTIVGPNSVQ CYHFGLSPDL PICKEQVQSC GPPPELLNGN VKEKTKEEYG HSEVVEYYCN 670        680        690        700        710        720
    PRFLMKGPNK IQCVDGEWTT LPVCIVEEST CGDIPELEHG WAQLSSPPYY YGDSVEFNCS 730        740        750        760        770        780
    ESFTMIGHRS ITCIHGVWTQ LPQCVAIDKL KKCKSSNLII LEEHLKNKKE FDHNSNIRYR 790        800        810        820        830        840
    CRGKEGWIHT VCINGRWDPE VNCSMAQIQL CPPPPQIPHS HNMTTTLNYR DGEKVSVLCQ 850        860        870        880        890        900
    ENYLIQEGEE ITCKDGRWQS IPLCVEKIPC SQPPQIEHGT INSSRSSQES YANGTKLSYT 910        920        930        940        950        960
    CEGGFRISEE NETTCYMGKW SSPPQCEGLP CKSPPEISHG VVAHMSDSYQ YGEEVTYKCF 970        980        990       1000       1010       1020
    EGFGIDGPAI AKCLGEKWSH PPSCIKTDCL SLPSFENAIP MGEKKDVYKA GEQVTYTCAT 1030       1040       1050       1060       1070       1080
    YYKMDGASNV TCINSRWTGR PTCRDTSCVN PPTVQNAYIV SRQMSKYPSG ERVRYQCRSP 1090       1100       1110       1120       1130       1140
    YEMFGDEEVM CLNGNWTEPP QCKDSTGKCG PPPPIDNGDI TSFPLSVYAP ASSVEYQCQN 1150       1160       1170       1180       1190       1200
    LYQLEGNKRI TCRNGQWSEP PKCLHPCVIS REIMENYNIA LRWTAKQKLY SRTGESVEFV 1210       1220       1230
    CKRGYRLSSR SHTLRTTCWD GKLEYPTCAK R
```

---

The invention claimed is:

1. A method of treating a disease in a subject by administering to a subject an effective amount of a pharmaceutical composition comprising a recombinant protein capable of binding to complement factor H (CFH), and thereby inducing increased binding of C3d and C3b by bound CFH compared to unbound CFH, wherein the recombinant protein binds to CFH within complement control proteins (CCPs) 8-10 of CFH and the recombinant protein is capable of binding to wild type CFH to form a complex with a $K_D$ of $1\times10^{-10}$ M or lower, or a nucleic acid encoding said recombinant protein, wherein the disease is selected from the group consisting of: Paroxysmal Nocturnal Hemoglobinuria (PNH), Atypical Haemolytic Uremic Syndrome (aHUS), Dense Deposit Disease (DDD), Age-related Macular Degeneration (AMD), Systemic lupus erythematosus (SLE), Sepsis, and Alzheimer's Disease.

2. The method of claim 1, wherein the disease is Age-related Macular Degeneration (AMD).

* * * * *

SEQUENCE LISTING

<160> NUMBER OF SEQ ID NOS: 9

<210> SEQ ID NO 1
<211> LENGTH: 104
<212> TYPE: PRT
<213> ORGANISM: Streptococcus pneumoniae

<400> SEQUENCE: 1

```
Ala Thr Glu Asn Glu Gly Ser Thr Gln Ala Ala Thr Ser Ser Asn Met
1               5                   10                  15

Ala Lys Thr Glu His Arg Lys Ala Lys Gln Val Val Asp Glu Tyr
                20                  25                  30

Ile Glu Lys Met Leu Arg Glu Ile Gln Leu Asp Arg Lys His Thr
            35                  40                  45

Gln Asn Val Ala Leu Asn Ile Lys Leu Ser Ala Ile Lys Thr Lys Tyr
    50                  55                  60
```

Leu Arg Glu Leu Asn Val Leu Glu Glu Lys Ser Lys Asp Glu Leu Pro
65                  70                  75                  80

Ser Glu Ile Lys Ala Lys Leu Asp Ala Ala Phe Glu Lys Phe Lys Lys
                85                  90                  95

Asp Thr Leu Lys Pro Gly Glu Lys
            100

<210> SEQ ID NO 2
<211> LENGTH: 79
<212> TYPE: PRT
<213> ORGANISM: Streptococcus pneumoniae

<400> SEQUENCE: 2

Lys Gln Val Val Asp Glu Tyr Ile Glu Lys Met Leu Arg Glu Ile Gln
1               5                   10                  15

Leu Asp Arg Arg Lys His Thr Gln Asn Val Ala Leu Asn Ile Lys Leu
                20                  25                  30

Ser Ala Ile Lys Thr Lys Tyr Leu Arg Glu Leu Asn Val Leu Glu Glu
            35                  40                  45

Lys Ser Lys Asp Glu Leu Pro Ser Glu Ile Lys Ala Lys Leu Asp Ala
        50                  55                  60

Ala Phe Glu Lys Phe Lys Lys Asp Thr Leu Lys Pro Gly Glu Lys
65                  70                  75

<210> SEQ ID NO 3
<211> LENGTH: 2725
<212> TYPE: DNA
<213> ORGANISM: Streptococcus pneumoniae
<220> FEATURE:
<221> NAME/KEY: misc_feature
<222> LOCATION: (2260)..(2260)
<223> OTHER INFORMATION: n is a, c, g, or t
<220> FEATURE:
<221> NAME/KEY: misc_feature
<222> LOCATION: (2723)..(2723)
<223> OTHER INFORMATION: n is a, c, g, or t

<400> SEQUENCE: 3
atgcttgtca ataatcacaa atatgtagat catatcttgt ttaggacagt aaaacatcct      60
aattactttt taaatattct tcctgagttg attggcttga ccttgttgag tcatgcttat     120
gtgacttttg ttttagtttt tccagtttat gcagttattt tgtatcgacg aatagctgaa     180
gaggaaaagc tattacatga agttataatc ccaaatggaa gcataaagag ataaatacaa     240
aattcgattt atacagtt catattgaag taatatagta aggttaaaga aaaaatatag      300
aaggaaataa acatgtttgc atcaaaaagc gaaagaaaag tacattattc aattcgtaaa     360
tttagtattg gagtagctag tgtagctgtt gccagtcttg ttatgggaag tgtggttcat     420
gcgacagaga acgagggaag tacccaagca gccacttctt ctaatatggc aaagacagaa     480
cataggaaag ctgctaaaca agtcgtcgat gaatatatag aaaaaatgtt gagggagatt     540
caactagata gaagaaaaca tacccaaaat gtcgccttaa acataaagtt gagcgcaatt     600
aaaacgaagt atttgcgtga attaaatgtt ttagaagaga gtcgaaaga tgagttgccg     660 tcagaaataa aagcaaagtt agacgcagct tttgagaagt ttaaaaaaga tacattgaaa     720
ccaggagaaa aggtagcaga agctaagaag aaggttgaag aagctaagaa aaaagccgag     780
gatcaaaaag aagaagatcg tcgtaactac ccaaccaata cttacaaaac gcttgaactt     840
gaaattgctg agttcgatgt gaagttaaa gaagcggagc ttgaactagt aaaagaggaa    900
gctaaagaat ctcgaaacga gggcacaatt aagcaagcaa aagagaaagt tgagagtaaa    960

```
aaagctgagg ctacaaggtt agaaaacatc aagacagatc gtaaaaaagc agaagaagaa   1020
gctaaacgaa aagcagatgg taagttgaag gaagctaatg tagcgacttc agatcaaggt   1080
aaaccaaagg ggcgggcaaa acgaggagtt cctggagagc tagcaacacc tgataaaaaa   1140
gaaaatgatg cgaagtcttc agattctagc gtaggtgaag aaactcttcc aagctcatcc   1200
ctgaaatcag gaaaaaggt agcagaagct gagaagaagg ttgaagaagc tgagaaaaaa   1260
gccaaggatc aaaagaaga agatcgccgt aactacccaa ccaatactta caaaacgctt   1320
gaccttgaaa ttgctgagtc cgatgtgaaa gttaagaag cggagcttga actagtaaaa   1380
gaggaagcta aggaacctcg agacgaggaa aaaattaagc aagcaaaagc gaaagttgag   1440
agtaaaaaag ctgaggctac aaggttagaa acatcaaga cagatcgtaa aaagcagaa   1500 gaagaagcta acgaaaagc agcagaagaa gataaagtta aagaaaaacc agctgaacaa   1560
ccacaaccag cgccggctac tcaaccagaa aaaccagctc aaaaccaga gaagccagct   1620 gaacaaccaa aagcagaaaa aacagatgat caacaagctg aagaagacta tgctcgtaga   1680
tcagaagaag aatataatcg cttgactcaa cagcaaccgc caaaaactga aaaaccagca   1740
caaccatcta ctccaaaaac aggctggaaa caagaaaacg gtatgtggta cttctacaat   1800
actgatggtt caatggcaac aggatggctc caaaacaacg gttcatggta ctatctaaac   1860
gctaatggtg ctatggcgac aggatggctc caaaacaatg gttcatggta ctatctaaac   1920
gctaatggtt caatggcaac aggatggctc caaaacaatg gttcatggta ctacctaaac   1980
gctaatggtg ctatggcgac aggatggctc caatacaatg gttcatggta ctacctaaac   2040
agcaatggcg ctatggcgac aggatggctc caatacaatg gctcatggta ctacctcaac   2100
gctaatggtg atatggcgac aggatggctc caaaacaacg gttcatggta ctacctcaac   2160
gctaatggtg atatggcgac aggatggctc caatacaacg gttcatggta ttacctcaac   2220
gctaatggtg atatggcgac aggttgggtg aaagatggan atacctggta ctatcttaaa   2280
gcatcaggtg ctatgaaagc aagccaatgg ttcaaagtat cagataaatg gtactatgtc   2340
aatggctcag gtgcccttgc agtcaacaca actgtagatg gctatggagt caatgccaat   2400
ggtgaatggg taaactaaac ctaatataac tagttaatac tgacttcctg taagaacttt   2460
ttaaagtatt ccctacaaat accatatcct ttcagtagat aatatacccct tgtaggaagt   2520 ttagattaaa aaataactct gtaatctcta gccggattta tagcgctaga gactacggag   2580
tttttttgat gaggaaagaa tggcggcatt caagagactc tttaagagag ttacgggttt   2640
taaactatta agccttctcc aattgcaaga gggcttcaat ctctgctagg gtgctagctt   2700
gcgaaatggc tccacggagt ttngc                                        2725
```

<210> SEQ ID NO 4
<211> LENGTH: 701
<212> TYPE: PRT
<213> ORGANISM: Streptococcus pneumoniae
<220> FEATURE:
<221> NAME/KEY: misc_feature
<222> LOCATION: (650)..(650)
<223> OTHER INFORMATION: Xaa can be any naturally occurring amino acid

<400> SEQUENCE: 4

Met Phe Ala Ser Lys Ser Glu Arg Lys Val His Tyr Ser Ile Arg Lys
1               5                   10                  15

Phe Ser Ile Gly Val Ala Ser Val Ala Val Ala Ser Leu Val Met Gly
            20                  25                  30

-continued

Ser Val Val His Ala Thr Glu Asn Glu Gly Ser Thr Gln Ala Ala Thr
         35                  40                  45

Ser Ser Asn Met Ala Lys Thr Glu His Arg Lys Ala Ala Lys Gln Val
 50                  55                  60

Val Asp Glu Tyr Ile Glu Lys Met Leu Arg Glu Ile Gln Leu Asp Arg
 65                  70                  75                  80

Arg Lys His Thr Gln Asn Val Ala Leu Asn Ile Lys Leu Ser Ala Ile
                 85                  90                  95

Lys Thr Lys Tyr Leu Arg Glu Leu Asn Val Leu Glu Glu Lys Ser Lys
                100                 105                 110

Asp Glu Leu Pro Ser Glu Ile Lys Ala Lys Leu Asp Ala Ala Phe Glu
            115                 120                 125

Lys Phe Lys Lys Asp Thr Leu Lys Pro Gly Glu Lys Val Ala Glu Ala
    130                 135                 140

Lys Lys Lys Val Glu Glu Ala Lys Lys Ala Glu Asp Gln Lys Glu
145                 150                 155                 160

Glu Asp Arg Arg Asn Tyr Pro Thr Asn Thr Tyr Lys Thr Leu Glu Leu
                165                 170                 175

Glu Ile Ala Glu Phe Asp Val Lys Val Lys Glu Ala Glu Leu Glu Leu
            180                 185                 190

Val Lys Glu Glu Ala Lys Glu Ser Arg Asn Glu Gly Thr Ile Lys Gln
    195                 200                 205

Ala Lys Glu Lys Val Glu Ser Lys Lys Ala Glu Ala Thr Arg Leu Glu
    210                 215                 220

Asn Ile Lys Thr Asp Arg Lys Lys Ala Glu Glu Ala Lys Arg Lys
225                 230                 235                 240

Ala Asp Gly Lys Leu Lys Glu Ala Asn Val Ala Thr Ser Asp Gln Gly
                245                 250                 255

Lys Pro Lys Gly Arg Ala Lys Arg Gly Val Pro Gly Glu Leu Ala Thr
            260                 265                 270

Pro Asp Lys Lys Glu Asn Asp Ala Lys Ser Ser Asp Ser Ser Val Gly
    275                 280                 285

Glu Glu Thr Leu Pro Ser Ser Ser Leu Lys Ser Gly Lys Lys Val Ala
290                 295                 300

Glu Ala Glu Lys Lys Val Glu Ala Glu Lys Lys Ala Lys Asp Gln
305                 310                 315                 320

Lys Glu Glu Asp Arg Arg Asn Tyr Pro Thr Asn Thr Tyr Lys Thr Leu
                325                 330                 335

Asp Leu Glu Ile Ala Glu Ser Asp Val Lys Val Lys Glu Ala Glu Leu
            340                 345                 350

Glu Leu Val Lys Glu Glu Ala Lys Glu Pro Arg Asp Glu Glu Lys Ile
    355                 360                 365

Lys Gln Ala Lys Ala Lys Val Glu Ser Lys Lys Ala Glu Ala Thr Arg
    370                 375                 380

Leu Glu Asn Ile Lys Thr Asp Arg Lys Lys Ala Glu Glu Glu Ala Lys
385                 390                 395                 400

Arg Lys Ala Ala Glu Glu Asp Lys Val Lys Glu Lys Pro Ala Glu Gln
                405                 410                 415

Pro Gln Pro Ala Pro Ala Thr Gln Glu Lys Pro Ala Pro Lys Pro
            420                 425                 430

Glu Lys Pro Ala Glu Gln Pro Lys Ala Glu Lys Thr Asp Asp Gln Gln
    435                 440                 445

Ala Glu Glu Asp Tyr Ala Arg Arg Ser Glu Glu Glu Tyr Asn Arg Leu

```
                450             455             460
Thr Gln Gln Gln Pro Pro Lys Thr Glu Lys Pro Ala Gln Pro Ser Thr
465                 470                 475                 480

Pro Lys Thr Gly Trp Lys Gln Glu Asn Gly Met Trp Tyr Phe Tyr Asn
                485                 490                 495

Thr Asp Gly Ser Met Ala Thr Gly Trp Leu Gln Asn Asn Gly Ser Trp
            500                 505                 510

Tyr Tyr Leu Asn Ala Asn Gly Ala Met Ala Thr Gly Trp Leu Gln Asn
        515                 520                 525

Asn Gly Ser Trp Tyr Tyr Leu Asn Ala Asn Gly Ser Met Ala Thr Gly
    530                 535                 540

Trp Leu Gln Asn Asn Gly Ser Trp Tyr Tyr Leu Asn Ala Asn Gly Ala
545                 550                 555                 560

Met Ala Thr Gly Trp Leu Gln Tyr Asn Gly Ser Trp Tyr Tyr Leu Asn
                565                 570                 575

Ser Asn Gly Ala Met Ala Thr Gly Trp Leu Gln Tyr Asn Gly Ser Trp
            580                 585                 590

Tyr Tyr Leu Asn Ala Asn Gly Asp Met Ala Thr Gly Trp Leu Gln Asn
        595                 600                 605

Asn Gly Ser Trp Tyr Tyr Leu Asn Ala Asn Gly Asp Met Ala Thr Gly
    610                 615                 620

Trp Leu Gln Tyr Asn Gly Ser Trp Tyr Tyr Leu Asn Ala Asn Gly Asp
625                 630                 635                 640

Met Ala Thr Gly Trp Val Lys Asp Gly Xaa Thr Trp Tyr Tyr Leu Lys
                645                 650                 655

Ala Ser Gly Ala Met Lys Ala Ser Gln Trp Phe Lys Val Ser Asp Lys
            660                 665                 670

Trp Tyr Tyr Val Asn Gly Ser Gly Ala Leu Ala Val Asn Thr Thr Val
        675                 680                 685

Asp Gly Tyr Gly Val Asn Ala Asn Gly Glu Trp Val Asn
    690                 695                 700

<210> SEQ ID NO 5
<211> LENGTH: 315
<212> TYPE: DNA
<213> ORGANISM: Artificial Sequence
<220> FEATURE:
<223> OTHER INFORMATION: codon-optimised DNA sequence used to express
      PspCN

<400> SEQUENCE: 5
gcaaccgaaa atgaaggtag cacccaggca gcaaccagca gcaatatggc aaaaaccgaa      60
catcgtaaag cagccaaaca ggttgtggat gagtatatcg aaaaaatgct gcgtgaaatt     120
cagctggatc gtcgtaaaca tacccagaat gttgcactga acattaaact gagcgccatc     180
aaaaccaaat atctgcgtga actgaatgtg ctggaagaga aaagcaaaga tgaactgccg     240
agcgaaatta agcaaaaact ggatgcagcc tttgaaaaat tcaaaaaaga taccctgaaa     300
ccgggtgaga aataa                                                     315

<210> SEQ ID NO 6
<211> LENGTH: 1231
<212> TYPE: PRT
<213> ORGANISM: Homo sapiens

<400> SEQUENCE: 6

Met Arg Leu Leu Ala Lys Ile Ile Cys Leu Met Leu Trp Ala Ile Cys
```

-continued

```
1               5                   10                  15
Val Ala Glu Asp Cys Asn Glu Leu Pro Pro Arg Arg Asn Thr Glu Ile
                20                  25                  30

Leu Thr Gly Ser Trp Ser Asp Gln Thr Tyr Pro Glu Gly Thr Gln Ala
                35                  40                  45

Ile Tyr Lys Cys Arg Pro Gly Tyr Arg Ser Leu Gly Asn Val Ile Met
            50                  55                  60

Val Cys Arg Lys Gly Glu Trp Val Ala Leu Asn Pro Leu Arg Lys Cys
65                  70                  75                  80

Gln Lys Arg Pro Cys Gly His Pro Gly Asp Thr Pro Phe Gly Thr Phe
                85                  90                  95

Thr Leu Thr Gly Gly Asn Val Phe Glu Tyr Gly Val Lys Ala Val Tyr
                100                 105                 110

Thr Cys Asn Glu Gly Tyr Gln Leu Leu Gly Glu Ile Asn Tyr Arg Glu
                115                 120                 125

Cys Asp Thr Asp Gly Trp Thr Asn Asp Ile Pro Ile Cys Glu Val Val
                130                 135                 140

Lys Cys Leu Pro Val Thr Ala Pro Glu Asn Gly Lys Ile Val Ser Ser
145                 150                 155                 160

Ala Met Glu Pro Asp Arg Glu Tyr His Phe Gly Gln Ala Val Arg Phe
                165                 170                 175

Val Cys Asn Ser Gly Tyr Lys Ile Glu Gly Asp Glu Glu Met His Cys
                180                 185                 190

Ser Asp Asp Gly Phe Trp Ser Lys Glu Lys Pro Lys Cys Val Glu Ile
                195                 200                 205

Ser Cys Lys Ser Pro Asp Val Ile Asn Gly Ser Pro Ile Ser Gln Lys
        210                 215                 220

Ile Ile Tyr Lys Glu Asn Glu Arg Phe Gln Tyr Lys Cys Asn Met Gly
225                 230                 235                 240

Tyr Glu Tyr Ser Glu Arg Gly Asp Ala Val Cys Thr Glu Ser Gly Trp
                245                 250                 255

Arg Pro Leu Pro Ser Cys Glu Glu Lys Ser Cys Asp Asn Pro Tyr Ile
                260                 265                 270

Pro Asn Gly Asp Tyr Ser Pro Leu Arg Ile Lys His Arg Thr Gly Asp
                275                 280                 285

Glu Ile Thr Tyr Gln Cys Arg Asn Gly Phe Tyr Pro Ala Thr Arg Gly
                290                 295                 300

Asn Thr Ala Lys Cys Thr Ser Thr Gly Trp Ile Pro Ala Pro Arg Cys
305                 310                 315                 320

Thr Leu Lys Pro Cys Asp Tyr Pro Asp Ile Lys His Gly Gly Leu Tyr
                325                 330                 335

His Glu Asn Met Arg Arg Pro Tyr Phe Pro Val Ala Val Gly Lys Tyr
                340                 345                 350

Tyr Ser Tyr Tyr Cys Asp Glu His Phe Glu Thr Pro Ser Gly Ser Tyr
                355                 360                 365

Trp Asp His Ile His Cys Thr Gln Asp Gly Trp Ser Pro Ala Val Pro
                370                 375                 380

Cys Leu Arg Lys Cys Tyr Phe Pro Tyr Leu Glu Asn Gly Tyr Asn Gln
385                 390                 395                 400

Asn Tyr Gly Arg Lys Phe Val Gln Gly Lys Ser Ile Asp Val Ala Cys
                405                 410                 415

His Pro Gly Tyr Ala Leu Pro Lys Ala Gln Thr Thr Val Thr Cys Met
                420                 425                 430
```

```
Glu Asn Gly Trp Ser Pro Thr Pro Arg Cys Ile Arg Val Lys Thr Cys
        435                 440                 445

Ser Lys Ser Ser Ile Asp Ile Glu Asn Gly Phe Ile Ser Glu Ser Gln
    450                 455                 460

Tyr Thr Tyr Ala Leu Lys Glu Lys Ala Lys Tyr Gln Cys Lys Leu Gly
465                 470                 475                 480

Tyr Val Thr Ala Asp Gly Glu Thr Ser Gly Ser Ile Thr Cys Gly Lys
                485                 490                 495

Asp Gly Trp Ser Ala Gln Pro Thr Cys Ile Lys Ser Cys Asp Ile Pro
            500                 505                 510

Val Phe Met Asn Ala Arg Thr Lys Asn Asp Phe Thr Trp Phe Lys Leu
        515                 520                 525

Asn Asp Thr Leu Asp Tyr Glu Cys His Asp Gly Tyr Glu Ser Asn Thr
    530                 535                 540

Gly Ser Thr Thr Gly Ser Ile Val Cys Gly Tyr Asn Gly Trp Ser Asp
545                 550                 555                 560

Leu Pro Ile Cys Tyr Glu Arg Glu Cys Glu Leu Pro Lys Ile Asp Val
                565                 570                 575

His Leu Val Pro Asp Arg Lys Lys Asp Gln Tyr Lys Val Gly Glu Val
            580                 585                 590

Leu Lys Phe Ser Cys Lys Pro Gly Phe Thr Ile Val Gly Pro Asn Ser
        595                 600                 605

Val Gln Cys Tyr His Phe Gly Leu Ser Pro Asp Leu Pro Ile Cys Lys
    610                 615                 620

Glu Gln Val Gln Ser Cys Gly Pro Pro Pro Glu Leu Leu Asn Gly Asn
625                 630                 635                 640

Val Lys Glu Lys Thr Lys Glu Glu Tyr Gly His Ser Glu Val Val Glu
                645                 650                 655

Tyr Tyr Cys Asn Pro Arg Phe Leu Met Lys Gly Pro Asn Lys Ile Gln
            660                 665                 670

Cys Val Asp Gly Glu Trp Thr Thr Leu Pro Val Cys Ile Val Glu Glu
        675                 680                 685

Ser Thr Cys Gly Asp Ile Pro Glu Leu Glu His Gly Trp Ala Gln Leu
    690                 695                 700

Ser Ser Pro Pro Tyr Tyr Tyr Gly Asp Ser Val Glu Phe Asn Cys Ser
705                 710                 715                 720

Glu Ser Phe Thr Met Ile Gly His Arg Ser Ile Thr Cys Ile His Gly
                725                 730                 735

Val Trp Thr Gln Leu Pro Gln Cys Val Ala Ile Asp Lys Leu Lys Lys
            740                 745                 750

Cys Lys Ser Ser Asn Leu Ile Ile Leu Glu Glu His Leu Lys Asn Lys
        755                 760                 765

Lys Glu Phe Asp His Asn Ser Asn Ile Arg Tyr Arg Cys Arg Gly Lys
    770                 775                 780

Glu Gly Trp Ile His Thr Val Cys Ile Asn Gly Arg Trp Asp Pro Glu
785                 790                 795                 800

Val Asn Cys Ser Met Ala Gln Ile Gln Leu Cys Pro Pro Pro Pro Gln
                805                 810                 815

Ile Pro Asn Ser His Asn Met Thr Thr Thr Leu Asn Tyr Arg Asp Gly
            820                 825                 830

Glu Lys Val Ser Val Leu Cys Gln Glu Asn Tyr Leu Ile Gln Glu Gly
        835                 840                 845
```

Glu Glu Ile Thr Cys Lys Asp Gly Arg Trp Gln Ser Ile Pro Leu Cys
850                 855                 860

Val Glu Lys Ile Pro Cys Ser Gln Pro Gln Ile Glu His Gly Thr
865                 870                 875                 880

Ile Asn Ser Ser Arg Ser Ser Gln Glu Ser Tyr Ala His Gly Thr Lys
                885                 890                 895

Leu Ser Tyr Thr Cys Glu Gly Gly Phe Arg Ile Ser Glu Glu Asn Glu
                900                 905                 910

Thr Thr Cys Tyr Met Gly Lys Trp Ser Ser Pro Pro Gln Cys Glu Gly
                915                 920                 925

Leu Pro Cys Lys Ser Pro Pro Glu Ile Ser His Gly Val Val Ala His
                930                 935                 940

Met Ser Asp Ser Tyr Gln Tyr Gly Glu Glu Val Thr Tyr Lys Cys Phe
945                 950                 955                 960

Glu Gly Phe Gly Ile Asp Gly Pro Ala Ile Ala Lys Cys Leu Gly Glu
                965                 970                 975

Lys Trp Ser His Pro Pro Ser Cys Ile Lys Thr Asp Cys Leu Ser Leu
                980                 985                 990

Pro Ser Phe Glu Asn Ala Ile Pro Met Gly Glu Lys Lys Asp Val Tyr
                995                 1000                1005

Lys Ala Gly Glu Gln Val Thr Tyr Thr Cys Ala Thr Tyr Tyr Lys
1010                1015                1020

Met Asp Gly Ala Ser Asn Val Thr Cys Ile Asn Ser Arg Trp Thr
1025                1030                1035

Gly Arg Pro Thr Cys Arg Asp Thr Ser Cys Val Asn Pro Pro Thr
1040                1045                1050

Val Gln Asn Ala Tyr Ile Val Ser Arg Gln Met Ser Lys Tyr Pro
1055                1060                1065

Ser Gly Glu Arg Val Arg Tyr Gln Cys Arg Ser Pro Tyr Glu Met
1070                1075                1080

Phe Gly Asp Glu Glu Val Met Cys Leu Asn Gly Asn Trp Thr Glu
1085                1090                1095

Pro Pro Gln Cys Lys Asp Ser Thr Gly Lys Cys Gly Pro Pro Pro
1100                1105                1110

Pro Ile Asp Asn Gly Asp Ile Thr Ser Phe Pro Leu Ser Val Tyr
1115                1120                1125

Ala Pro Ala Ser Ser Val Glu Tyr Gln Cys Gln Asn Leu Tyr Gln
1130                1135                1140

Leu Glu Gly Asn Lys Arg Ile Thr Cys Arg Asn Gly Gln Trp Ser
1145                1150                1155

Glu Pro Pro Lys Cys Leu His Pro Cys Val Ile Ser Arg Glu Ile
1160                1165                1170

Met Glu Asn Tyr Asn Ile Ala Leu Arg Trp Thr Ala Lys Gln Lys
1175                1180                1185

Leu Tyr Ser Arg Thr Gly Glu Ser Val Glu Phe Val Cys Lys Arg
1190                1195                1200

Gly Tyr Arg Leu Ser Ser Arg Ser His Thr Leu Arg Thr Thr Cys
1205                1210                1215

Trp Asp Gly Lys Leu Glu Tyr Pro Thr Cys Ala Lys Arg
1220                1225                1230

<210> SEQ ID NO 7
<211> LENGTH: 115
<212> TYPE: PRT

<213> ORGANISM: Artificial Sequence
<220> FEATURE:
<223> OTHER INFORMATION: N-terminally Cys modified PspCN

<400> SEQUENCE: 7

Cys Gly Ser Gly Ser Gly Ser Gly Ser Gly Gly Ala Thr Glu Asn Glu
1               5                   10                  15

Gly Ser Thr Gln Ala Ala Thr Ser Ser Asn Met Ala Lys Thr Glu His
            20                  25                  30

Arg Lys Ala Ala Lys Gln Val Val Asp Glu Tyr Ile Glu Lys Met Leu
        35                  40                  45

Arg Glu Ile Gln Leu Asp Arg Arg Lys His Thr Gln Asn Val Ala Leu
    50                  55                  60

Asn Ile Lys Leu Ser Ala Ile Lys Thr Lys Tyr Leu Arg Glu Leu Asn
65                  70                  75                  80

Val Leu Glu Glu Lys Ser Lys Asp Glu Leu Pro Ser Glu Ile Lys Ala
                85                  90                  95

Lys Leu Asp Ala Ala Phe Glu Lys Phe Lys Lys Asp Thr Leu Lys Pro
            100                 105                 110

Gly Glu Lys
        115

<210> SEQ ID NO 8
<211> LENGTH: 115
<212> TYPE: PRT
<213> ORGANISM: Artificial Sequence
<220> FEATURE:
<223> OTHER INFORMATION: C-terminally Cys modified PspCN

<400> SEQUENCE: 8

Ala Thr Glu Asn Glu Gly Ser Thr Gln Ala Ala Thr Ser Ser Asn Met
1               5                   10                  15

Ala Lys Thr Glu His Arg Lys Ala Ala Lys Gln Val Val Asp Glu Tyr
            20                  25                  30

Ile Glu Lys Met Leu Arg Glu Ile Gln Leu Asp Arg Arg Lys His Thr
        35                  40                  45

Gln Asn Val Ala Leu Asn Ile Lys Leu Ser Ala Ile Lys Thr Lys Tyr
    50                  55                  60

Leu Arg Glu Leu Asn Val Leu Glu Glu Lys Ser Lys Asp Glu Leu Pro
65                  70                  75                  80

Ser Glu Ile Lys Ala Lys Leu Asp Ala Ala Phe Glu Lys Phe Lys Lys
                85                  90                  95

Asp Thr Leu Lys Pro Gly Glu Lys Gly Ser Gly Ser Gly Ser Gly Ser
            100                 105                 110

Gly Gly Cys
        115

<210> SEQ ID NO 9
<211> LENGTH: 143
<212> TYPE: PRT
<213> ORGANISM: Streptococcus pneumoniae

<400> SEQUENCE: 9

Ala Thr Glu Asn Glu Gly Ala Thr Gln Val Pro Thr Ser Ser Asn Arg
1               5                   10                  15

Ala Asn Glu Ser Gln Ala Glu Gln Gly Glu Gln Pro Lys Lys Leu Asp
            20                  25                  30

Ser Glu Arg Asp Lys Ala Arg Lys Glu Val Glu Glu Tyr Val Lys Lys

-continued

```
        35                  40                  45

Ile Val Gly Glu Ser Tyr Ala Lys Ser Thr Lys Lys Arg His Thr Ile
    50                  55                  60

Thr Val Ala Leu Val Asn Glu Leu Asn Asn Ile Lys Asn Glu Tyr Leu
65                  70                  75                  80

Asn Lys Ile Val Glu Ser Thr Ser Glu Ser Gln Leu Gln Ile Leu Met
                85                  90                  95

Met Glu Ser Arg Ser Lys Val Asp Glu Ala Val Ser Lys Phe Glu Lys
            100                 105                 110

Asp Ser Ser Ser Ser Ser Ser Ser Asp Ser Ser Thr Lys Pro Glu Ala
        115                 120                 125

Ser Asp Thr Ala Lys Pro Asn Lys Pro Thr Glu Pro Gly Glu Lys
    130                 135                 140
```